(12) United States Patent
Dirckx et al.

(10) Patent No.: US 10,279,345 B2
(45) Date of Patent: May 7, 2019

(54) FLUIDIC SYSTEMS COMPRISING AN INCUBATION CHANNEL, INCLUDING FLUIDIC SYSTEMS FORMED BY MOLDING

(71) Applicant: OPKO Diagnostics, LLC, Woburn, MA (US)

(72) Inventors: Matthew Dirckx, Somerville, MA (US); Jason Taylor, Windham, NH (US); Vincent Linder, Tewksbury, MA (US)

(73) Assignee: OPKO Diagnostics, LLC, Woburn, MA (US)

( * ) Notice: Subject to any disclaimer, the term of this patent is extended or adjusted under 35 U.S.C. 154(b) by 475 days.

(21) Appl. No.: 14/966,937

(22) Filed: Dec. 11, 2015

(65) Prior Publication Data

US 2016/0207042 A1    Jul. 21, 2016

Related U.S. Application Data

(60) Provisional application No. 62/131,357, filed on Mar. 11, 2015, provisional application No. 62/091,187, filed on Dec. 12, 2014.

(51) Int. Cl.
*B01L 3/00*       (2006.01)
*G01N 33/543*   (2006.01)
(Continued)

(52) U.S. Cl.
CPC ... *B01L 3/502715* (2013.01); *B01L 3/502746* (2013.01); *B01L 3/502784* (2013.01);
(Continued)

(58) Field of Classification Search
CPC ......... B01L 2200/06; B01L 2200/0673; B01L 2200/16; B01L 2300/0627;
(Continued)

(56) References Cited

U.S. PATENT DOCUMENTS 3,735,640 A    5/1973    Chizhov et al.
4,318,994 A    3/1982    Meyer et al.
(Continued)

FOREIGN PATENT DOCUMENTS

CN    1254845 A         5/2000
DE    101 15 474 A1    10/2002
(Continued)

OTHER PUBLICATIONS

International Search Report and Written Opinion for Application No. PCT/US2015/065187 dated May 4, 2016.
(Continued)

*Primary Examiner* — Maureen Wallenhorst
(74) *Attorney, Agent, or Firm* — Wolf, Greenfield & Sacks, P.C.

(57) ABSTRACT

Fluidic devices and methods involving incubation and/or mixing of assay components are provided. In some embodiments, a biological and/or chemical assay may be performed in a fluidic device. The fluidic device may be designed to allow for controlled incubation and/or mixing of two or more assay components. In some such embodiments, the fluidic device may include an incubation channel having a relatively large cross-sectional dimension in fluid communication with a detection channel. The incubation channel may allow for adequate mixing and/or incubation of two or more assay components prior to analysis of the assay. In certain embodiments, the detection channel may be used to provide feedback on the extent of incubation and/or mixing. Based on the feedback, one or more component of the fluidic system may be regulated to allow the requisite degree of mixing and/or incubation to be achieved.

22 Claims, 19 Drawing Sheets

(51) Int. Cl.
  *G01N 35/00* (2006.01)
  *G01N 15/14* (2006.01)
  *G01N 15/10* (2006.01)
  *G01N 35/10* (2006.01)

(52) U.S. Cl.
  CPC ..... *G01N 15/1404* (2013.01); *G01N 15/1459* (2013.01); *G01N 15/1463* (2013.01); *G01N 15/1484* (2013.01); *G01N 33/54366* (2013.01); *G01N 35/00069* (2013.01); *B01L 2200/06* (2013.01); *B01L 2200/0673* (2013.01); *B01L 2200/16* (2013.01); *B01L 2300/0627* (2013.01); *B01L 2300/0816* (2013.01); *B01L 2300/0838* (2013.01); *B01L 2300/0858* (2013.01); *B01L 2300/0861* (2013.01); *B01L 2300/0867* (2013.01); *B01L 2300/12* (2013.01); *B01L 2300/1827* (2013.01); *B01L 2400/0406* (2013.01); *B01L 2400/0487* (2013.01); *B01L 2400/0694* (2013.01); *G01N 15/1475* (2013.01); *G01N 2015/1006* (2013.01); *G01N 2035/00158* (2013.01); *G01N 2035/00237* (2013.01); *G01N 2035/00356* (2013.01); *G01N 2035/1034* (2013.01); *Y10T 436/2575* (2015.01)

(58) Field of Classification Search
  CPC ..... B01L 2300/0816; B01L 2300/0838; B01L 2300/0858; B01L 2300/0861; B01L 2300/0867; B01L 2300/12; B01L 2300/1827; B01L 2400/0406; B01L 2400/0487; B01L 2400/0694; B01L 3/502715; B01L 3/502746; B01L 3/502784; G01N 15/1459; G01N 15/1463; G01N 15/1475; G01N 15/1484; G01N 2015/1006; G01N 2035/00158; G01N 2035/00356; G01N 2035/1034; G01N 33/54366; G01N 35/00069; Y10T 436/25; Y10T 436/2575
  USPC ......... 436/63, 174, 180; 422/68.1, 501–504; 435/287.3
  See application file for complete search history.

(56) References Cited

U.S. PATENT DOCUMENTS

| | | | |
|---|---|---|---|
| 4,387,183 | A | 6/1983 | Francis |
| 4,517,302 | A | 5/1985 | Saros |
| 4,963,498 | A | 10/1990 | Hillman et al. |
| 5,051,237 | A | 9/1991 | Grenner et al. |
| 5,219,762 | A | 6/1993 | Katamine et al. |
| 5,268,147 | A | 12/1993 | Zabetakis et al. |
| 5,286,454 | A | 2/1994 | Nilsson et al. |
| 5,376,252 | A | 12/1994 | Ekström et al. |
| 5,478,751 | A | 12/1995 | Oosta et al. |
| 5,486,335 | A | 1/1996 | Wilding et al. |
| 5,571,410 | A | 11/1996 | Swedberg et al. |
| 5,635,358 | A | 6/1997 | Wilding et al. |
| 5,637,469 | A | 6/1997 | Wilding et al. |
| 5,726,026 | A | 3/1998 | Wilding et al. |
| 5,731,212 | A | 3/1998 | Gavin et al. |
| 5,783,148 | A | 7/1998 | Cottingham et al. |
| 5,842,787 | A | 12/1998 | Kopf-Sill et al. |
| 5,866,345 | A | 2/1999 | Wilding et al. |
| 5,876,675 | A | 3/1999 | Kennedy |
| 5,942,443 | A | 8/1999 | Parce et al. |
| 5,955,028 | A | 9/1999 | Chow |
| 5,957,579 | A | 9/1999 | Kopf-Sill et al. |
| 6,019,944 | A | 2/2000 | Buechler |
| 6,042,709 | A | 3/2000 | Parce et al. |
| 6,046,056 | A | 4/2000 | Parce et al. |
| 6,103,199 | A | 8/2000 | Bjornson et al. |
| 6,136,272 | A | 10/2000 | Weigl et al. |
| 6,146,489 | A | 11/2000 | Wirth |
| 6,146,589 | A | 11/2000 | Chandler |
| 6,168,948 | B1 | 1/2001 | Anderson et al. |
| 6,176,962 | B1 | 1/2001 | Soane et al. |
| 6,184,029 | B1 | 2/2001 | Wilding et al. |
| 6,186,660 | B1 | 2/2001 | Kopf-Sill et al. |
| 6,214,560 | B1 | 4/2001 | Yguerabide et al. |
| 6,238,538 | B1 | 5/2001 | Parce et al. |
| 6,241,560 | B1 | 6/2001 | Furusawa et al. |
| 6,251,343 | B1 | 6/2001 | Dubrow et al. |
| 6,274,337 | B1 | 8/2001 | Parce et al. |
| 6,296,020 | B1 | 10/2001 | McNeely et al. |
| 6,331,439 | B1 | 12/2001 | Cherukuri et al. |
| 6,333,200 | B1 | 12/2001 | Kaler et al. |
| 6,361,958 | B1 | 3/2002 | Shieh et al. |
| 6,413,782 | B1 | 7/2002 | Parce et al. |
| 6,416,642 | B1 | 7/2002 | Alajoki et al. |
| 6,429,025 | B1 | 8/2002 | Parce et al. |
| 6,432,720 | B2 | 8/2002 | Chow |
| 6,479,299 | B1 | 11/2002 | Parce et al. |
| 6,488,872 | B1 | 12/2002 | Beebe et al. |
| 6,488,894 | B1 | 12/2002 | Miethe et al. |
| 6,488,896 | B2 | 12/2002 | Weigl et al. |
| 6,517,234 | B1 | 2/2003 | Kopf-Sill et al. |
| 6,524,656 | B2 | 2/2003 | Even et al. |
| 6,551,841 | B1 | 4/2003 | Wilding et al. |
| 6,610,499 | B1 | 8/2003 | Fulwyler et al. |
| 6,613,512 | B1 | 9/2003 | Kopf-Sill et al. |
| 6,613,525 | B2 | 9/2003 | Nelson et al. |
| 6,620,625 | B2 | 9/2003 | Wolk et al. |
| 6,632,619 | B1 | 10/2003 | Harrison et al. |
| 6,638,482 | B1 | 10/2003 | Ackley et al. |
| 6,656,430 | B2 | 12/2003 | Sheppard, Jr. et al. |
| 6,669,831 | B2 | 12/2003 | Chow et al. |
| 6,705,357 | B2 | 3/2004 | Jeon et al. |
| 6,709,869 | B2 | 3/2004 | Mian et al. |
| 6,716,620 | B2 | 4/2004 | Bashir et al. |
| 6,742,661 | B1 | 6/2004 | Schulte et al. |
| 6,761,962 | B2 | 7/2004 | Bentsen et al. |
| 6,780,584 | B1 | 8/2004 | Edman et al. |
| 6,794,197 | B1 | 9/2004 | Indermuhle et al. |
| 6,818,184 | B2 | 11/2004 | Fulwyler et al. |
| 6,827,095 | B2 | 12/2004 | O'Connor et al. |
| 6,828,143 | B1 | 12/2004 | Bard |
| 6,830,936 | B2 | 12/2004 | Anderson et al. |
| 6,858,185 | B1 | 2/2005 | Kopf-Sill et al. |
| 6,878,271 | B2 | 4/2005 | Gilbert et al. |
| 6,878,755 | B2 | 4/2005 | Singh et al. |
| 6,949,377 | B2 | 9/2005 | Ho |
| 6,953,550 | B2 | 10/2005 | Sheppard, Jr. et al. |
| 6,982,787 | B1 | 1/2006 | Wapner et al. |
| 6,989,128 | B2 | 1/2006 | Alajoki et al. |
| 7,005,292 | B2 | 2/2006 | Wilding et al. |
| 7,015,046 | B2 | 3/2006 | Wohlstadter et al. |
| 7,018,830 | B2 | 3/2006 | Wilding et al. |
| 7,067,263 | B2 | 6/2006 | Parce et al. |
| 7,087,148 | B1 | 8/2006 | Blackburn et al. |
| 7,091,048 | B2 | 8/2006 | Parce et al. |
| 7,160,423 | B2 | 1/2007 | Chien et al. |
| 7,276,330 | B2 | 10/2007 | Chow et al. |
| 7,332,328 | B2 | 2/2008 | Webb et al. |
| 7,540,475 | B2 | 6/2009 | Stenkamp et al. |
| 7,816,411 | B2 | 3/2010 | Tonkovich et al. |
| 7,749,723 | B2 | 7/2010 | Fang |
| 7,999,937 | B1 | 8/2011 | Srivastava et al. |
| 8,030,057 | B2 | 10/2011 | Linder et al. |
| 8,075,778 | B2 | 12/2011 | Guenther et al. |
| 8,202,492 | B2 | 6/2012 | Linder et al. |
| 8,221,700 | B2 | 7/2012 | Steinmiller et al. |
| 8,222,049 | B2 | 7/2012 | Linder et al. |
| 8,389,272 | B2 | 3/2013 | Linder et al. |
| 8,409,527 | B2 | 4/2013 | Linder et al. |
| 8,475,737 | B2 | 7/2013 | Linder et al. |
| 8,480,975 | B2 | 7/2013 | Steinmiller et al. |
| 8,481,303 | B2 | 7/2013 | Faris et al. |
| 8,501,416 | B2 | 8/2013 | Linder et al. |
| 8,567,425 | B2 | 10/2013 | Tan et al. |

(56) References Cited

U.S. PATENT DOCUMENTS

| | | |
|---|---|---|
| 8,580,569 B2 | 11/2013 | Linder et al. |
| 8,591,829 B2 | 11/2013 | Taylor et al. |
| 8,679,843 B2 | 3/2014 | Faris et al. |
| 8,765,062 B2 | 7/2014 | Linder et al. |
| 9,255,866 B2 | 2/2016 | Dirckx et al. |
| 2002/0001818 A1 | 1/2002 | Brock |
| 2002/0019059 A1 | 2/2002 | Chow et al. |
| 2002/0071788 A1 | 6/2002 | Fujii et al. |
| 2002/0092767 A1 | 7/2002 | Bjornson et al. |
| 2002/0142618 A1 | 10/2002 | Parce et al. |
| 2002/0199094 A1 | 12/2002 | Strand et al. |
| 2003/0012697 A1 | 1/2003 | Hahn et al. |
| 2003/0040105 A1 | 2/2003 | Sklar et al. |
| 2003/0082081 A1 | 5/2003 | Fouillet et al. |
| 2003/0118486 A1 | 6/2003 | Zhou et al. |
| 2003/0124623 A1 | 7/2003 | Yager et al. |
| 2003/0138969 A1 | 7/2003 | Jakobsen et al. |
| 2003/0185713 A1 | 10/2003 | Leonard et al. |
| 2003/0207328 A1 | 11/2003 | Yguerabide et al. |
| 2004/0077074 A1 | 4/2004 | Ackley et al. |
| 2004/0115094 A1 | 6/2004 | Gumbrecht et al. |
| 2004/0115731 A1 | 6/2004 | Hansen et al. |
| 2004/0195728 A1 | 10/2004 | Slomski et al. |
| 2004/0228771 A1 | 11/2004 | Zhou et al. |
| 2004/0259268 A1 | 12/2004 | Jacobs et al. |
| 2005/0118073 A1 | 6/2005 | Facer et al. |
| 2005/0161669 A1 | 7/2005 | Jovanovich et al. |
| 2005/0221281 A1 | 10/2005 | Ho |
| 2005/0238545 A1 | 10/2005 | Parce et al. |
| 2005/0255003 A1 | 11/2005 | Summersgill et al. |
| 2005/0272159 A1 | 12/2005 | Ismagilov et al. |
| 2006/0002827 A1 | 1/2006 | Curcio et al. |
| 2006/0094119 A1 | 5/2006 | Ismagilov et al. |
| 2006/0147909 A1 | 7/2006 | Rarbach et al. |
| 2006/0254916 A1 | 11/2006 | Hernandez et al. |
| 2006/0257991 A1 | 11/2006 | McDevitt et al. |
| 2006/0257992 A1 | 11/2006 | McDevitt et al. |
| 2006/0275852 A1 | 12/2006 | Montagu |
| 2007/0048189 A1 | 3/2007 | Cox et al. |
| 2007/0195127 A1 | 8/2007 | Ahn et al. |
| 2007/0298433 A1 | 12/2007 | Sia et al. |
| 2008/0038839 A1 | 2/2008 | Linder et al. |
| 2008/0085219 A1 | 4/2008 | Beebe et al. |
| 2008/0248590 A1 | 10/2008 | Gulliksen et al. |
| 2008/0280365 A1 | 11/2008 | Grumann et al. |
| 2009/0075390 A1 | 3/2009 | Linder et al. |
| 2009/0282978 A1 | 11/2009 | Jensen et al. |
| 2010/0009430 A1 | 1/2010 | Wan et al. |
| 2010/0122899 A1 | 5/2010 | Hartman et al. |
| 2010/0158756 A1 | 6/2010 | Taylor et al. |
| 2010/0208543 A1 | 8/2010 | Takahashi et al. |
| 2010/0209916 A1 | 8/2010 | Zon |
| 2010/0216964 A1 | 8/2010 | Zech et al. |
| 2011/0103176 A1 | 5/2011 | Van Dam et al. |
| 2011/0120562 A1 | 5/2011 | Enqing et al. |
| 2011/0171748 A1 | 7/2011 | Cox et al. |
| 2011/0253224 A1 | 10/2011 | Linder et al. |
| 2011/0256551 A1 | 10/2011 | Linder et al. |
| 2012/0241013 A1 | 9/2012 | Linder et al. |
| 2013/0157286 A1 | 6/2013 | Linder et al. |
| 2013/0236375 A1 | 9/2013 | Tan et al. |
| 2013/0252321 A1 | 9/2013 | Steinmiller et al. |
| 2013/0330748 A1 | 12/2013 | Linder et al. |
| 2014/0023565 A1 | 1/2014 | Taylor et al. |
| 2014/0038166 A1 | 2/2014 | Linder et al. |
| 2014/0038167 A1 | 2/2014 | Linder et al. |
| 2014/0093866 A1 | 4/2014 | Tan et al. |
| 2014/0272935 A1 | 9/2014 | Linder et al. |

FOREIGN PATENT DOCUMENTS

| | | |
|---|---|---|
| EP | 0 110 771 B1 | 3/1988 |
| EP | 0 281 201 A1 | 9/1988 |
| EP | 0 430 248 A2 | 6/1991 |
| EP | 0 643 307 A1 | 3/1995 |
| EP | 0 481 020 B1 | 3/1996 |
| EP | 1 054 259 A1 | 11/2000 |
| EP | 1 946 830 A1 | 7/2008 |
| EP | 1 992 404 A2 | 11/2008 |
| EP | 2 071 026 A1 | 6/2009 |
| JP | 2000-019175 A | 1/2000 |
| JP | 2001-000197 A | 1/2001 |
| JP | 2001-004628 A | 1/2001 |
| JP | 2002-236131 A | 8/2002 |
| JP | 2002-340897 A | 11/2002 |
| JP | 2003-075444 A | 3/2003 |
| JP | 2003-223674 A | 8/2003 |
| JP | 2008-139296 A | 6/2008 |
| WO | WO 91/01003 A | 1/1991 |
| WO | WO 00/22434 A1 | 4/2000 |
| WO | WO 00/46595 A1 | 8/2000 |
| WO | WO 01/14865 A1 | 3/2001 |
| WO | WO 2002/022250 A2 | 3/2002 |
| WO | WO 2003/054513 A2 | 7/2003 |
| WO | WO 2003/062826 A2 | 7/2003 |
| WO | WO 2004/042341 A2 | 5/2004 |
| WO | WO 2004/087951 A2 | 10/2004 |
| WO | WO 2004/087951 A3 | 10/2004 |
| WO | WO 2004/097419 A1 | 11/2004 |
| WO | WO 2005/056186 A1 | 6/2005 |
| WO | WO 2005/066613 A1 | 7/2005 |
| WO | WO 2005/072858 A1 | 8/2005 |
| WO | WO 2006/018044 A1 | 2/2006 |
| WO | WO 2006/042332 A2 | 4/2006 |
| WO | WO 2006/056787 A1 | 6/2006 |
| WO | WO 2006/113727 A2 | 10/2006 |
| WO | WO 2008/118098 A1 | 10/2008 |
| WO | WO 2008/123112 A1 | 10/2008 |
| WO | WO 2013/154946 A1 | 10/2013 |

OTHER PUBLICATIONS

Ahn et al., Disposable Smart Lab on a Chip for Point-of-Care Clinical Diagnostics, Proceedings of the IEEE. 2004; 92(1):154-173.

Andersson et al., Micromachined Flow-Through Filter—Chamber for Chemical Reactions on Beads. Sensors and Actuators. 2000; B67:203-208.

Atencia et al., Capillary inserts in microcirculatory systems. Lab Chip. Apr. 2006;6(4):575-7. Epub Jan. 20, 2006.

Atencia et al., Steady flow generation in microcirculatory systems. Lab Chip. Apr. 2006;6(4):567-74. Epub Jan. 20, 2006.

Dardion, et al., "Chemical Sensing Using an Integrated Microfluidic System Based on the Berthelot Reaction", *Sensors and Actuators B*, vol. 76, pp. 235-243 (2001).

Dodge et al., Electrokinetically driven microfluidic chips with surface-modified chambers for heterogeneous immunoassays. Anal Chem. Jul. 15, 2001;73(14):3400-9.

Fredrickson et al., Macro-to-micro interfaces for microfluidic devices. Lab Chip. Dec. 2004;4(6):526-33. Epub Nov. 10, 2004.

Grodzinski et al., A Modular Microfluidic System for Cell Pre-concentration and Genetic Sample Preparation. Biomedical Microdevices. 2003;5(4):303-310.

Guo et al, Valve-based microfluidic droplet micromixer and mercury (II) ion detection. Sensors and Actuators. 2011; 172: 546-51.

Harries et al, A numerical model for segmented flow in a microreactor. Int J Heat and Mass Transfer. 2003; 46: 3313-22.

Juncker et al., Autonomous microfluidic capillary system. Anal Chem. Dec. 15, 2002;74(24):6139-44.

Kumar et al. Segmented flow synthesis of Ag nanoparticles in spiral microreactor: Role of continuous and disperzsed phase. Chem Eng J. 2012; 192: 357-68. With Supporting Information.

Linder et al., Reagent-loaded cartridges for valveless and automated fluid delivery in microfluidic devices. Anal Chem. Jan. 1, 2005;77(1):64-71.

Moorthy et al., Microfluidic Tectonics Platform: A colorimetric, disposable botulinum toxin enzyme-linked immunosorbent assay system. Electrophoresis. Jun. 2004;25(10-11):1705-13.

Nguyen et al., An analytical model for mixing based on time-interleaved sequential segmentation. Microfluid Nanofluid. 2005; 1: 373-5.

(56) References Cited

OTHER PUBLICATIONS

Nguyen et al., Modelling, fabrication and characterization of a polymeric micromixer based on sequential segmentation. Biomed Microdevices. Jun. 2006;8(2):133-9.

Obeid et al., Microfabricated device for DNA and RNA amplification by continuous-flow polymerase chain reaction and reverse transcription-polymerase chain reaction with cycle number selection. Anal Chem. Jan. 15, 2003;75(2):288-95.

Proceedings of uTAS 2004, 8th International Conference on Miniaturized Systems in Chemistry and Life Sciences, Sep. 26-30, Malmo, Sweden, Edited by Thomas Laurell, Johan Nilsson, Klays Jensen, D. Jed Harrison, Jorg P. Kutter, The Royal Society of Chemistry, pp. 1-135 (2004).

Shui et al., Multiphase flow in microfluidic systems—control and applications of droplets and interfaces. Adv Colloid Interface Sci. May 31, 2007;133(1):35-49. Epub Mar. 16, 2007.

Sia et al., An integrated approach to a portable and low-cost immunoassay for resource-poor settings. Angew Chem Int Ed Engl. Jan. 16, 2004;43(4):498-502.

Sia et al., Microfluidic devices fabricated in poly(dimethylsiloxane) for biological studies. Electrophoresis. Nov. 2003;24(21):3563-76.

Song et al., A microfluidic system for controlling reaction networks in time. Angew Chem Int Ed. 2003;42(7):767-772.

Weigl et al., Lab-On-A-Chip for Drug Development. Adv Drug Deliv Rev. Feb. 24, 2003;55(3):349-77.

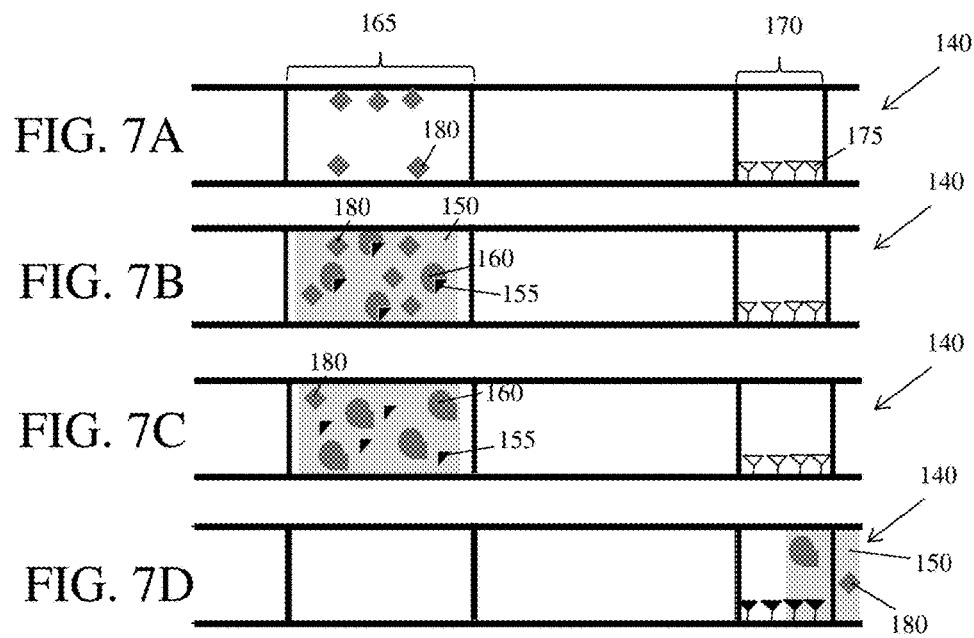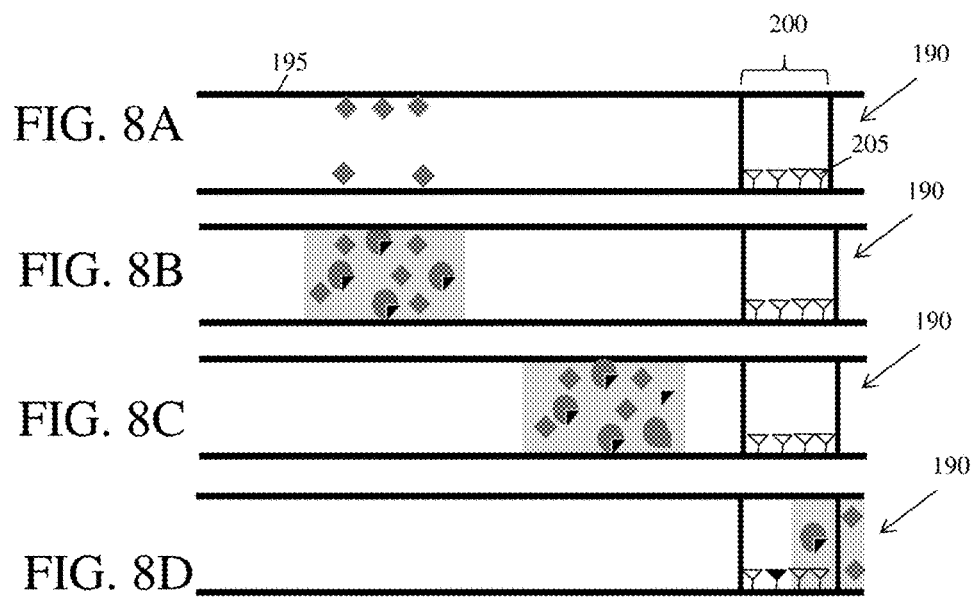

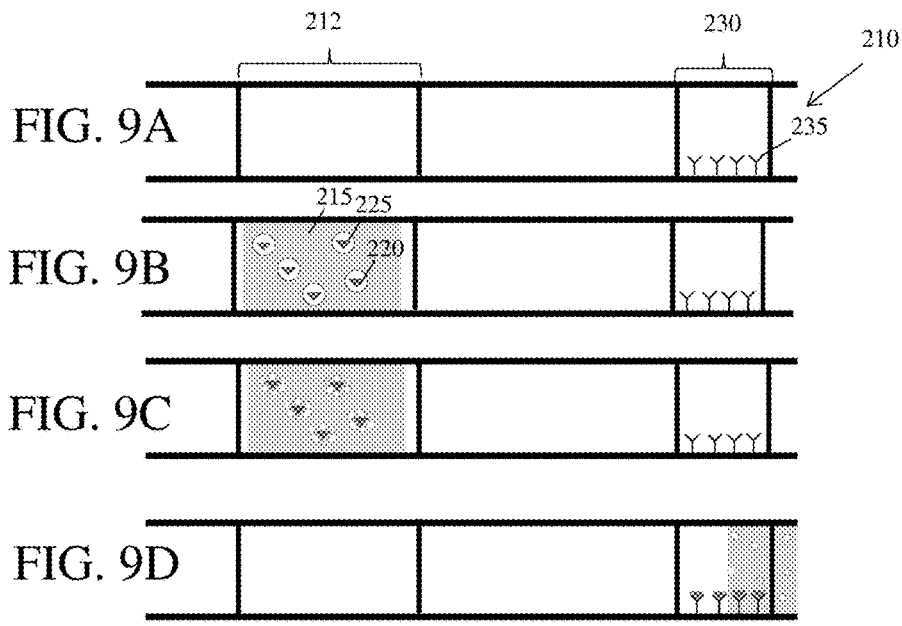
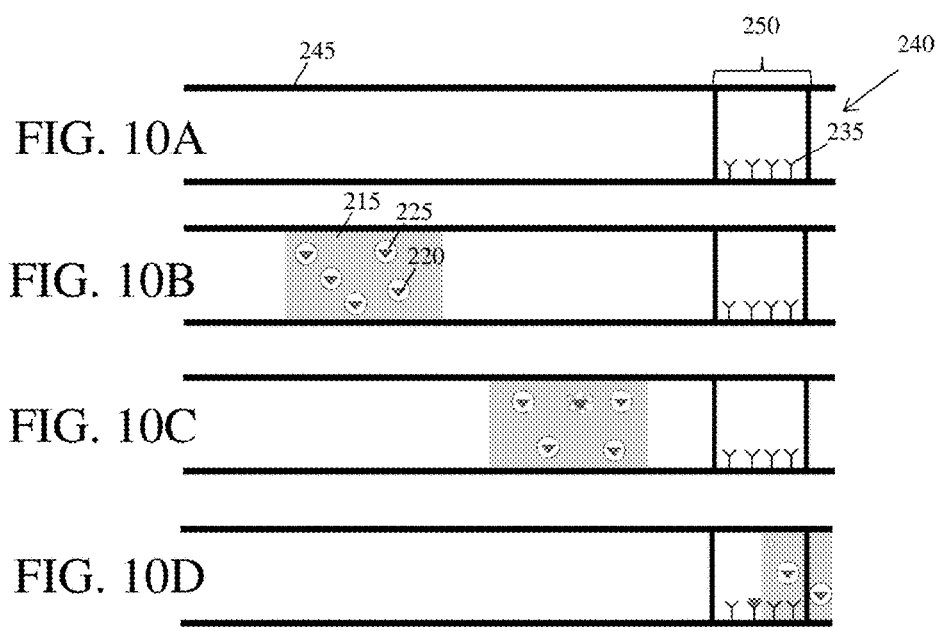

FLUIDIC SYSTEMS COMPRISING AN INCUBATION CHANNEL, INCLUDING FLUIDIC SYSTEMS FORMED BY MOLDING

RELATED APPLICATIONS

This application claims priority under 35 U.S.C. § 119(e) to U.S. Provisional Patent Application No. 62/131,357, filed Mar. 11, 2015, and entitled "Fluidic Systems Comprising an Incubation Channel, Including Fluidic Systems Formed by Molding", and U.S. Provisional Patent Application No. 62/091,187, filed Dec. 12, 2014, and entitled "Fluidic Systems Comprising an Incubation Channel", each of which is incorporated herein by reference.

FIELD OF INVENTION

The present embodiments relate generally to methods for flowing fluids in fluidic devices, and more specifically, to methods that involve the incubation and/or mixing of fluids.

BACKGROUND

The manipulation of fluids plays an important role in fields such as chemistry, microbiology, and biochemistry. These fluids may include liquids or gases and may provide reagents, solvents, reactants, or rinses to chemical or biological processes. While various fluidic (e.g., microfluidic) methods and devices, such as microfluidic assays, can provide inexpensive, sensitive and accurate analytical platforms, fluid manipulations—such as the mixture of multiple fluids, sample introduction, introduction of reagents, storage of reagents, separation of fluids, collection of waste, extraction of fluids for off-chip analysis, and transfer of fluids from one chip to the next—can add a level of cost and sophistication. Accordingly, advances in the field that could reduce costs, simplify use, and/or improve fluid manipulations in microfluidic systems would be beneficial.

SUMMARY OF THE INVENTION

Methods for flowing fluids in fluidic devices, and related components, devices and systems associated therewith are provided. The subject matter of this application involves, in some cases, interrelated methods, alternative solutions to a particular problem, and/or a plurality of different uses of fluids and devices.

In one set of embodiments, methods are provided. In some embodiments, a method, comprises introducing a sample comprising a sample component into a sample collector, and connecting the sample connector to a sample inlet port of an article, wherein the article comprises first and second sides, wherein the first side comprises an incubation channel, and wherein the first side and/or second side comprises a detection channel in fluid communication with the incubation channel, and wherein the sample inlet port is in fluid communication with the incubation channel. The method involves flowing, at a first flow rate, at least a portion of the sample from the sample collector to the incubation channel, flowing at least a portion of the sample into a part, but not all, of the detection channel, and reducing the flow rate of the sample to a second flow rate, wherein the second flow rate is less than the first flow rate and/or is zero. The method also involves modulating the flow rate of the sample to a third flow rate which is greater than or less than the second flow rate, and flowing the sample through remaining parts of the detection channel.

In another embodiment, a method comprises flowing, at a first flow rate, at least a portion of the sample from the sample collector to the incubation channel; flowing at least a portion of the sample into a part, but not all, of the detection channel, detecting at least a portion of the sample at the detection channel; reducing the flow rate of the sample to a second flow rate, wherein the second flow rate is less than the first flow rate and/or is zero; modulating the flow rate of the sample, wherein the third flow rate may be greater than or less than the first or second flow rate; and flowing the sample through remaining parts of the detection channel.

In some embodiments, a method comprises introducing a sample comprising a sample component into a sample collector and connecting the sample connector to a sample inlet port of an article, wherein the article comprises first and second sides, wherein the first side comprises an incubation channel, wherein the first side and/or second side comprises a detection channel in fluid communication with the incubation channel, and wherein the sample inlet port is in fluid communication with the incubation channel. The method may further comprise flowing, at a first flow rate, at least a portion of the sample from the sample collector to the incubation channel; flowing at least a portion of the sample into a part, but not all, of the detection channel, detecting at least a portion of the sample at the detection channel; reducing the flow rate of the sample to a second flow rate, wherein the second flow rate is less than the first flow rate and/or is zero; and flowing the sample through remaining parts of the detection channel.

In another embodiment, a method comprises introducing a sample comprising a sample component into a sample collector and connecting the sample connector to a sample inlet port of an article, wherein the article comprises first and second sides, wherein the first side comprises an incubation channel, and wherein the first side and/or second side comprises a detection channel in fluid communication with the incubation channel, and wherein the sample inlet port is in fluid communication with the incubation channel. The method may further comprise contacting a liquid with a reagent deposited on a surface of the sample collector or a surface of the article and removing at least a portion of the reagent from the surface such that the reagent is dissolved or suspended in the liquid; mixing the sample component with the reagent in at least a portion of the liquid in the incubation channel; and flowing the liquid comprising the sample component and the reagent through at least a portion of the detection channel.

In one embodiment, a method comprises introducing a sample comprising a sample component into a sample collector and connecting the sample connector to a sample inlet port of an article, wherein the article comprises first and second sides, wherein the first side comprises an incubation channel, and wherein the first side and/or second side comprises a detection channel in fluid communication with the incubation channel, and wherein the sample inlet port is in fluid communication with the incubation channel. In such cases, the incubation channel has a width of at least about 100 microns and less than or equal to about 2 mm, a height of at least about 50 microns and less than or equal to about 2 mm, and a volume of at least 5 µL. The detection channel has a width of at least about 50 microns and less than or equal to about 300 microns, and a height of at least about 10 microns and less than or equal to about 300 microns and the detection channel comprises a reagent deposited on a surface of the detection channel. The method may further comprise flowing at least a portion of the sample from the sample collector to the incubation channel; mixing the sample component with a reagent in a liquid in the incubation channel; and flowing the liquid comprising the sample component and the reagent through at least a portion of the detection channel.

In another set of embodiments, fluidic systems are provided. In one embodiment, a fluidic system comprises an article comprising first and second sides, wherein the first side comprises an incubation channel, wherein the first side and/or second side comprises a detection channel, and wherein a first intervening channel passes through the article and is positioned between the incubation channel and the detection channel. The incubation channel has a width of at least about 100 microns and less than or equal to about 2 mm, a height of at least about 50 microns and less than or equal to about 2 mm, and a volume of at least 5 µL. The detection channel has a width of at least about 50 microns and less than or equal to about 300 microns, and a height of at least about 10 microns and less than or equal to about 300 microns, and the detection channel comprising a reagent deposited on a surface of the detection channel. In such cases, a ratio of heights of the incubation channel to the detection channel is at least 2:1. The fluidic system may further comprise a sample inlet port in fluid communication with the incubation channel and an outlet port in fluid communication with the detection channel.

In another embodiment, a fluidic system comprises an article comprising first and second sides, wherein the first side comprises an incubation channel, and wherein the first side and/or second side comprises a detection channel in fluid communication with the incubation channel. The incubation channel has a width of at least about 100 microns and less than or equal to about 2 mm, a height of at least about 50 microns and less than or equal to about 2 mm, and a volume of at least 5 µL. The detection channel has a width of at least about 50 microns and less than or equal to about 300 microns, and a height of at least about 10 microns and less than or equal to about 300 microns, and the detection channel comprising a reagent deposited on a surface of the detection channel. In such cases, a ratio of heights of the incubation channel to the detection channel is at least 2:1. The fluidic system may further comprise a sample inlet port in fluid communication with the incubation channel; an outlet port in fluid communication with the detection channel; and a sample collector adapted and arranged to be connected to the sample inlet port of the article.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 7A-7D show schematic diagrams of an assay comprising an incubation step in a fluidic device comprising an incubation channel according to one set of embodiments;

FIGS. 8A-8D show schematic diagrams of an assay comprising an incubation step in a fluidic device lacking an incubation channel according to one set of embodiments;

FIGS. 9A-9D show schematic diagrams of an assay comprising an incubation step in a fluidic device comprising an incubation channel according to one set of embodiments;

FIGS. 10A-10D show schematic diagrams of an assay comprising an incubation step in a fluidic device lacking an incubation channel according to one set of embodiments;

DETAILED DESCRIPTION

Figure 1A:
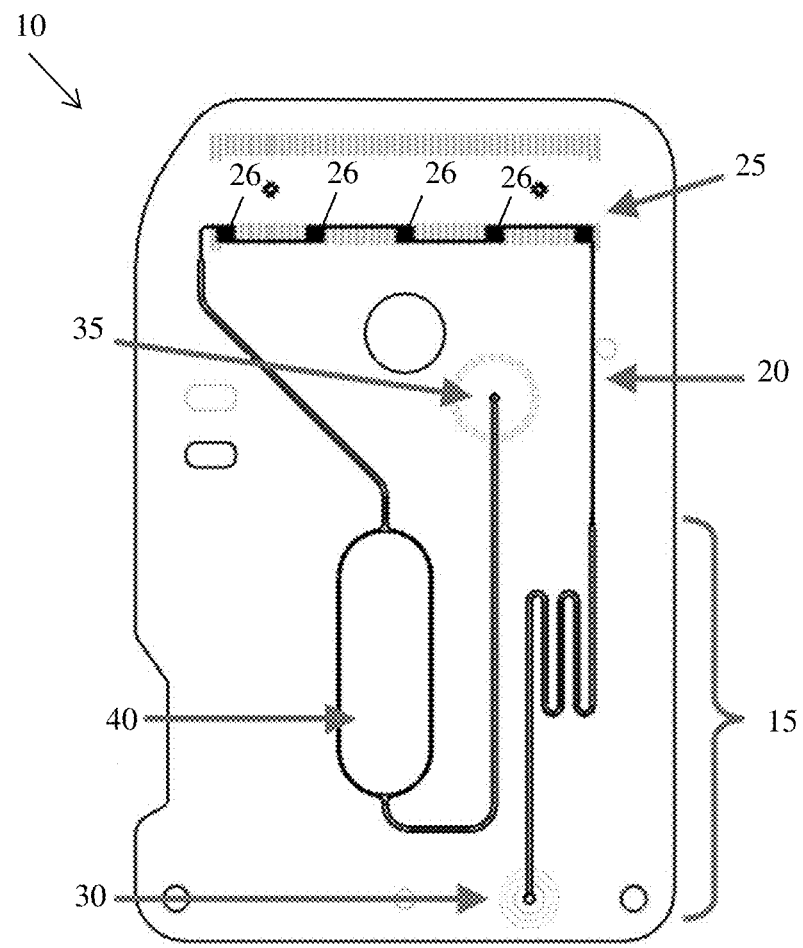
FIGS. 1A-1B show exemplary fluidic devices according to one set of embodiments.

Fluidic devices and methods involving incubation and/or mixing of assay components are provided. In some embodiments, a biological and/or chemical assay may be performed in a fluidic device. The fluidic device may be designed to allow for controlled incubation and/or mixing of two or more assay components (e.g., sample and reagent). In some such embodiments, the fluidic device may comprise an incubation channel having a relatively large cross-sectional dimension in fluid communication with a detection channel. The incubation channel may allow for adequate mixing and/or incubation of two or more assay components prior to analysis of the assay. In certain embodiments, the detection channel may be used to provide feedback, e.g., on the presence of a sample component in the incubation channel and/or the extent of incubation and/or mixing. Based on the feedback, one or more component of the fluidic system, such as fluid flow source, may be regulated to allow the requisite degree of mixing and/or incubation to be achieved. In some embodiments, the controlled incubation and/or mixing of assay components in an incubation channel, as described herein, may allow for improved assay performance (e.g., sensitivity, specificity, and/or reproducibility) and simplification in the design and operations of fluidic devices for assays that rely on incubation and/or mixing of assay components.

Though fluidic devices exist for performing biological and/or chemical assays, certain assays cannot be readily and/or accurately performed in conventional fluidic devices due to inadequate mixing and/or incubation of assay components. For example, sufficient incubation is an important part of assays that require the target analyte to be released from a natural binding partner in the sample in order for target analyte to be detected. In some such embodiments, the amount of target analyte released, and accordingly detected, is dependent on the incubation time and insufficient control over incubation results in inaccurate results and/or irreproducibility of the assay. In certain embodiments, assay sensitivity may depend on the length of and/or temperature of incubation. For example, the amount of analyte bound to a detector binding partner (e.g., antibody) may be increased by prolonged contact and/or incubation at elevated temperatures. Conventional fluidic devices have tried to address this problem by altering the design of the fluidic device and fluid handling in the fluidic device. However, many of these conventional devices suffer from problems such as clogging, rely on complex device constructions that may be difficult to fabricate, and/or rely on complex assay methods that may be difficult to implement, e.g., at a point of care setting. The fluidic devices, described herein, may allow for sufficient mixing and/or incubation without the shortcomings of many conventional fluidic devices and can be used to perform assays not readily and/or accurately implemented in conventional fluidic devices.

In some embodiments, a biological and/or chemical assay comprising an incubation step and/or mixing step may be performed in a fluidic device. As described herein, the fluidic device may be designed to allow for controlled incubation and/or mixing of two or more assay components (e.g., sample component and a reagent; reagent and a diluent; reagent and a buffer). In one exemplary embodiment, a fluidic device 10 comprises an incubation channel 15 as shown illustratively in FIG. 1A. The incubation channel may be in fluid communication with a detection channel 20. As shown in illustratively in FIG. 1A, the detection channel is positioned between the incubation channel and a detection zone 25. The detection zone may include several analysis regions 26. However, in other embodiments, the detection channel may be a part of the detection zone (e.g., the detection channel may be a channel of the detection zone, associated with one or more detectors).

In other embodiments, a portion of the incubation channel may be a part of the detection zone (e.g., an area associated with one or more detectors). Such a configuration may allow detection of the sample while in the incubation channel, e.g., to ensure that the leading edge of the sample (e.g., the sample/air interface) is positioned in the incubation channel during an incubation step. For example, as shown illustratively in FIG. 1B, a portion of the incubation channel 15 comprises a detection zone 27, while portions of detection channel 20 comprise other analysis regions 26. Upon detection of the sample at detection zone 27, the sample may be stopped or the flow rate reduced to incubate all or a portion of the sample in the incubation channel. In some embodiments, substantially no binding of the sample takes place in the incubation channel at detection zone 27.

In certain embodiments, the sample that resides in the incubation channel during incubation is in the form of a fluid plug. For example, a fluid sample may be flanked on both ends by air plugs so that a first air plug, a fluid sample, and a second air plug are positioned in the incubation channel during incubation.

In some embodiments, the dimensions (and/or cross-sectional area) of the channel at detection zone 27 are the same, or are similar to, dimensions (and/or cross-sectional area) of the incubation channel upstream of detection zone 27, e.g., as described herein. Accordingly, the dimensions and/or cross-sectional area) of the incubation channel at the detection zone may be larger than the dimensions (and/or cross-sectional area) of the channels at the detection zone 25 where binding of a sample component may take place.

One or more of the incubation channel, detection channel, and/or detection zone may be connected to a feedback system, which may be used to control one or more aspects of incubation step and/or mixing. For instance, in some embodiments, a detection zone may be used to detect a sample component prior to the arrival of at least a portion of the sample (e.g., at least about 80% of the sample) at a downstream reaction area. One or more signals or data may be generated corresponding to the sample component. Using this data, a control system may modulate subsequent fluid flow in the fluidic device. For instance, based on the data, the control system may reduce the flow rate of the sample to a flow rate less than the initial flow rate and/or to zero to allow for additional incubation or mixing. In some embodiments, a method of modulating fluid flow to control incubation and/or mixing in the fluidic device illustrated in FIG. 1A may comprise introducing a sample into a sample collector e.g., a blood collector). Suitable sample collectors are described below and in U.S. Pat. No. 8,202,492, issued Jun. 19, 2012 (filed May 1, 2008) and entitled "Fluidic Connectors and Microfluidic Systems" [C1256.70000US01], which is incorporated by reference in its entirety. The sample collector (e.g., blood collector) may comprise one or more channels. In some embodiments, the sample collector may comprise one or more reagents, e.g., deposited inside and/or on at least a portion of at least one channel surface of the sample collector. In some such cases, the sample may remove at least a portion of the reagent(s) and dissolve or suspend the reagent(s). In other embodiments, however, the sample collector does not contain a reagent.

Figure 1B:
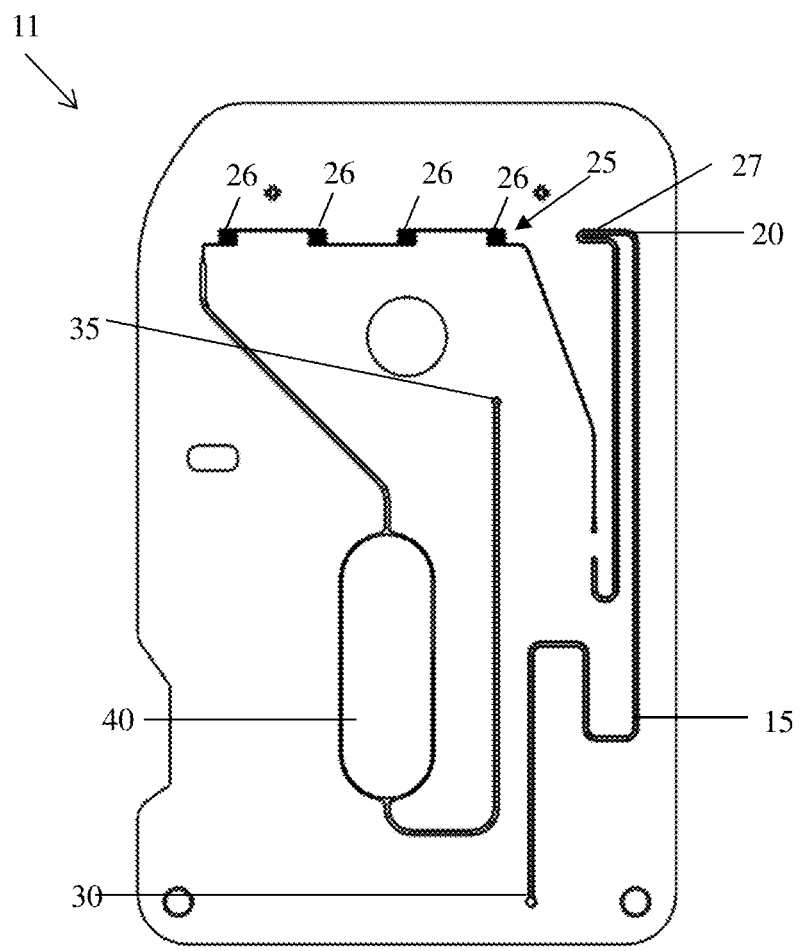

Referring to FIGS. 1A and 1B, the sample collector containing the sample may then be connected to a sample inlet port 30 of the fluidic device. The sample collector may be a fluidic connector in certain embodiments. In some embodiments, the sample collector may provide fluid communication between two channels on the fluidic device that prior to connection of the sample collector were not in fluid communication with each other. For instance, in some embodiments, a sample collector comprising a channel is used to connect two independent channels in a fluidic device so as to allow fluid communication between the two independent channels. One or both of the independent channels may optionally be pre-filled with reagents (e.g., antibody solutions, washing buffers and amplification reagents), which can be used to perform the analysis. These reagents may be stored (e.g., sealed) in the channels of the substrate for long periods of time (e.g., 1 year) prior to use. Prior to connection of the sample collector and the fluidic device, the channel of the sample collector may be filled with a sample (e.g., blood). The sample may be obtained, for example, by pricking a finger of a user until blood is drawn from the finger into the channel (e.g., by capillary forces). Upon connection of the sample collector and the channels of the fluidic device, the sample can pass through a detection zone and/or analysis regions within the fluidic device.

In embodiments in which the sample collector is connected to the fluidic device, a volume or pressure source may be connected to a fluid flow source port 35 (e.g., an outlet) and an applied force (e.g., a vacuum or reduce pressure) may cause the sample to flow into the fluidic device. In some embodiments, the sample may flow directly into the incubation channel after entering the sample inlet port. In other embodiments, the sample may enter another structure (e.g., a channel) prior to entering the incubation channel. In some instances, the incubation channel may have one or more dimensions (e.g., length, width, height) and/or volume that allows the incubation channel to contain substantially all of the sample (e.g., at least about 80% of the volume of the sample; at least about 95% of the volume of the sample, the entire sample). For example, the incubation chamber may be configured to contain samples having a volume of at least about 0.0005 mL, at least about 0.001 mL, 0.005 mL, at least about 0.01 mL, at least about 0.02 mL, at least about 0.03 mL, at least about 0.05 mL, at least about 0.08 mL, or at least about 0.01 mL and less than or equal to about 1 mL, less than or equal to about 0.75 mL, less than or equal to about 0.5 mL, less than or equal to about 0.25 mL, or less than or equal to about 0.1 mL. All combinations of the above-referenced ranges are possible. In some instances, the volume of the incubation channel may be similar to the volume of the sample. For instance, in some embodiments, the ratio of the volume of the incubation channel to the volume of the sample may be less than or equal to about 3:1, less than or equal to about 2.5:1, less than or equal to about 2:1, less than or equal to about 1.5:1, or less than or equal to about 1:1 and at least about 0.6:1, at least about 0.7:1, at least about 0.8:1, or at least about 0.9:1. All combinations of the above-referenced ranges are possible. In some embodiments, the incubation channel may have a larger cross-section area than another channel (e.g., detection channel) in the fluidic device. In other embodiments, the incubation channel is designed to be smaller in volume than the volume of the sample, e.g., such that it cannot contain a relatively large percentage of the sample.

In some embodiments, at least a portion of the sample (or a reagent) is incubated in the incubation channel for a period of time. As described herein, the flow of the sample may be stopped, or the flow rate reduced, during the incubation step. For example, in some embodiments, a sample or reagent may be incubated (e.g., in an incubation channel and/or a portion of a detection channel described herein) for a time of at least 1 minute, at least 3 minutes, at least 5 minutes, at least 7 minutes, at least 9 minutes, at least 11 minutes, at least 13 minutes, at least 15 minutes, at least 17 minutes, at least 19 minutes, at least 20 minutes, at least 30 minutes, at least 40 minutes, at least 50 minutes, at least 60 minutes. The time may be less than or equal to 60 minutes, less than or equal to 50 minutes, less than or equal to 40 minutes, less than or equal to 30 minutes, less than or equal to 20 minutes, less than or equal to 19 minutes, less than or equal to 17 minutes, less than or equal to 15 minutes, less than or equal to 13 minutes, less than or equal to 12 minutes, less than or equal to 11 minutes, less than or equal to 10 minutes, less than or equal to 9 minutes, less than or equal to 7 minutes, less than or equal to 5 minutes, less than or equal to 3 minutes, or less than or equal to 1 minute. Combinations of the above-referenced ranges are also possible (e.g. at least 5 minutes and less than or equal to 15 minutes). Other ranges are also possible.

A sample or reagent may be incubated at any suitable temperature. In some embodiments, a sample or reagent may be incubated (e.g., in an incubation channel and/or a portion of a detection channel described herein) at a temperature (e.g., an incubation temperature) of at least 15° C., at a temperature of at least 20° C., at a temperature of at least 25° C., at least 30° C., at least 35° C., at least 40° C., at least 45° C., at least 50° C., at least 55° C., or at least 60° C. The temperature may be less than or equal to 65° C., less than or equal to 60° C., less than or equal to 55° C., less than or equal to 50° C., less than or equal to 45° C., less than or equal to 40° C., less than or equal to 35° C., less than or equal to 30° C., or less than or equal to 25° C. Combinations of the above-referenced ranges are also possible (e.g., at least 45° C. and less than or equal to 55° C.). Other ranges are also possible.

In some embodiments, the volume or pressure source may be modulated to a predetermined setting for a predetermined length of time so that at least a portion of the sample flows into the incubation channel. In some such embodiments, a detector, e.g., for determining whether or not the incubation channel has been filled with the sample, is not needed or present at the incubation channel. Instead, the filling of the incubation channel, including the predetermined volume or pressure source settings and time (e.g., vacuum level and time of application of the vacuum) may be determined and adjusted based on the type of sample and its flow properties (e.g., whole blood capillary whole blood drawn from a finger stick, venous whole blood, plasma, serum, urine, saliva, etc., including its viscosity), as well as the channel dimensions leading up to and including the incubation channel (e.g., width, height, length, and thereby resistance to fluid flow). The pressure source level and timing of application of the pressure source may be tailored for the particular application.

In certain embodiments, at least a portion, but not all, of the sample enters into the incubation channel upon the incubation step. In some cases, the sample enters into the incubation channel, but does not enter into any downstream channels such as the detection channel, detection zone, waste zone, or outlet of the device. In other embodiments, at least a portion of the sample enters into the incubation channel, but the leading edge of the sample (e.g., an air/sample interface) does not enter into, or stop at, a channel downstream of the incubation channel within a range of cross-sectional areas. For instance, the sample may be stopped, or the flow rate reduced for incubation, when the leading edge of the sample reaches a channel having a relatively large cross-sectional area so that the sample does not clog the channel during and/or after incubation. In general, there is an increased tendency for certain samples (especially at a sample/air interface) to clog in channels having a relatively small cross-sectional area due to drying, clotting, and/or coagulation of the sample, which can increase resistance to fluid flow when sample flow is resumed.

In some embodiments, this tendency to clog may be addressed by having the sample (including the leading edge of the sample such as the sample/air interface) stop, or flow rate reduced when the sample reaches, a channel having a certain cross-sectional area. The cross-sectional area of the channel may be, for example, at least 0.008 mm$^2$, at least 0.01 mm$^2$, at least 0.02 mm$^2$, at least 0.03 mm$^2$, at least 0.04 mm², at least 0.05 mm², at least 0.06 mm², at least 0.08 mm², at least 0.10 mm², at least 0.12 mm², at least 0.14 mm², at least 0.16 mm², at least 0.18 mm², at least 0.20 mm², at least 0.30 mm², at least 0.40 mm², at least 0.50 mm², at least 0.60 mm², at least 0.70 mm², at least 0.80 mm², at least 0.90 mm², or at least 1.00 mm². In some embodiments, the cross-sectional area may be less than or equal to 1.00 mm², less than or equal to 0.90 mm², less than or equal to 0.80 mm², less than or equal to 0.70 mm², less than or equal to 0.60 mm², less than or equal to 0.50 mm², less than or equal to 0.40 mm², less than or equal to 0.30 mm², less than or equal to 0.25 mm², less than or equal to 0.20 mm², less than or equal to 0.175 mm², less than or equal to 0.15 mm², less than or equal to 0.1 mm², less than or equal to 0.05 mm², less than or equal to 0.04 mm², less than or equal to 0.02 mm², less than or equal to 0.015 mm², or less than or equal to 0.010 mm². Combinations of the above-referenced ranges are also possible. Other ranges are also possible. In some embodiments, the incubation channel has a cross-sectional area in one or more of the above-referenced ranges.

In some embodiments, a detection channel of a detection zone (e.g., where binding of a sample component takes place) has a cross-sectional area that is smaller than a cross-sectional area of the incubation channel. The detection channel of a detection zone may have, for example, a cross-sectional area of at least 0.001 mm², at least 0.002 mm², 0.004 mm², 0.005 mm², 0.006 mm², 0.008 mm², at least 0.01 mm², at least 0.02 mm², at least 0.03 mm², at least 0.04 mm², at least 0.05 mm², at least 0.06 mm², at least 0.08 mm², or at least 0.10 mm². In some embodiments, the cross-sectional area may be less than or equal to 0.016 mm², less than or equal to 0.014 mm², less than or equal to 0.012 mm², less than or equal to 0.010 mm², less than or equal to 0.008 mm², less than or equal to 0.006 mm², less than or equal to 0.005 mm², or less than or equal to 0.004 mm², less than or equal to 0.003 mm², or less than or equal to 0.002 mm². Combinations of the above-referenced ranges are also possible. Other ranges are also possible.

In some embodiments, the sample may flow through the incubation channel and a portion of the sample may reach the detection channel. As described herein, in some embodiments, the detection channel may have a significantly smaller cross-sectional area than the incubation channel. Accordingly, the flow rate inside the detection channel and/or the volume of the detection channel may be significantly less than the flow rate and/or volume of the incubation channel. In some embodiments, at least a portion of the sample may enter into a detection region (e.g., detection channel and/or detection zone) whereby the presence or absence of the sample or sample component and/or one or more characteristic of the sample or sample component are detected. In some such embodiments, the portion of the sample may flow into part, but not all, of the detection region (e.g., detection channel, detection zone). In certain embodiments, a small percentage of the sample (e.g., less than or equal to about 10%, less than or equal to about 5%) may flow into the detection region to initiate such analysis. One or more signals generated from such detection may be sent to a control system. For instance, detection may involve detecting the presence of a sample via a light absorbance or a transmission measurement.

In some cases, the feedback from the detection may be used to alter one or more component of the fluidic system to modulate fluid flow. For example, detection of the sample passing across the detection zone may trigger control of whether or not a particular valve is actuated to modulate fluid flow in the incubation channel. In some such embodiments, the one or more signals generated from the detection of the sample may be compared to one or more pre-set values, and based (at least in part) on this feedback and comparison, a control system may modulate (e.g., cease or reduce) fluid flow in the incubation channel and/or other portion of the fluidic device (e.g., entire fluidic device) if the measured signals falls out of range with the pre-set values. In some instances, fluid flow of one portion of the device may be regulated separately from another portion of the device using, e.g., a valve such as a vent valve. Vent valves for the regulation of fluid flow are described in U.S. Patent Publication No. 2011/0120562, filed Nov. 24, 2010, entitled "Fluid Mixing and Delivery in Microfluidic Systems," [C1256.70005US01], which is incorporated by reference in its entirety.

In some embodiments, based on the information from the signal, the volume or pressure source may be modulated to increase or decrease the flow rate, or in other cases, the flow rate may be maintained. In one example, the sample may have a first flow rate before detection (e.g., at a detection region such as the detection zone) and the sample may have a second flow rate after detection. The second flow rate may be significantly less than the first flow rate. For instance, the second flow rate may be less than or equal to about 50% (e.g., less than or equal to about 40%, less than or equal to about 30%, less than or equal to about 20%, less than or equal to about 10%, less than or equal to about 5%, less than or equal to about 1%) of the first flow rate. In some instances, the second flow rate may be zero. The reduction in flow rate may allow sufficient incubation and/or mixing to occur before the remaining portion of the sample leaves the incubation channel and/or arrives at a certain downstream location, such as a reaction area/analysis reaion. In other embodiments, the second flow rate may be greater than or equal to the first flow rate.

Figure 2:
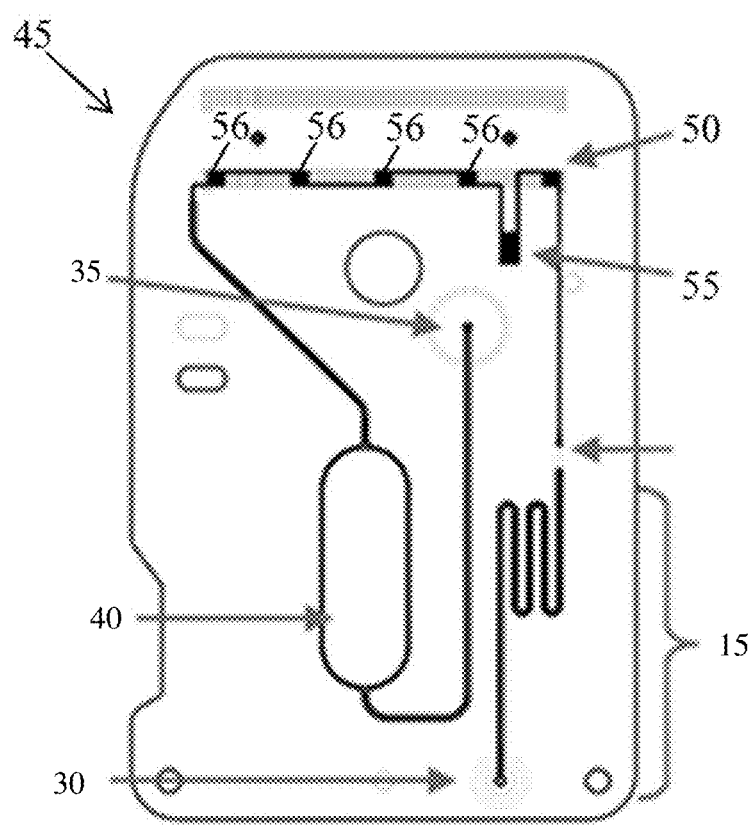
FIG. 2 shows a fluidic device according to one set of embodiments.

In some embodiments, to prevent the portion of the sample at the detection zone from reaching an analysis region and/or another downstream detection zone, the fluidic device may comprise an additional channel 55 between a detection zone 50 and a downstream feature of the fluidic device e.g. additional analysis regions 56) as shown illustratively in FIG. 2. As a result of detecting a component of a sample at analysis region 56, fluid flow may cease or be reduced so that the sample is further incubated or mixed in the mixing channel. After sufficient incubation or mixing, the sample may then continue towards the remaining analysis regions of the detection zone where a component of the sample can be detected and/or analyzed.

In some embodiments in which the flow rate is adjusted after detection of the sample or sample component in a detection region, after a certain period of time, which may be preset based on the assay or determined by subsequent detection of the sample or sample component, the flow rate may be modulated to a third flow rate which is greater than or less than the second flow rate. For instance, after a preset incubation time the flow rate may increase to a third flow rate that is greater than the second flow rate. The third flow rate may be greater than, less than, or equal to the first flow rate. In some embodiments, the fluidic device may be configured to allow for fluid flow to be slowed significantly or stopped without negatively influencing subsequent operations (e.g., fluid flow) in the fluidic device. For instance, fluid flow may be stopped and restarted in the fluidic device without clogging occurring.

In some embodiments, a method may further involve reducing the temperature of the sample, a reagent, and/or channels (e.g., incubation channel, or channels at a detection zone) to a temperature less than a temperature used during an incubation step after the incubation step occurs. For example, the temperature may be reduced during a detection step. Such a temperature reduction may, in some embodiments, improve and/or increase the flow rate of the sample through the detection zone. For example, the temperature may be reduced to less than or equal to 60° C., less than or equal to 55° C., less than or equal to 50° C., less than or equal to 45° C., less than or equal to 40° C., less than or equal to 37° C., less than or equal to 35° C., less than or equal to 30° C., or less than or equal to 25° C. In some embodiments, the temperature may be at least 15° C., at a temperature of at least 20° C., at a temperature of at least 25° C., at least 30° C., at least 35° C., at least 40° C., at least 45° C., at least 50° C., or at least 55° C. Combinations of the above-referenced ranges are also possible (e.g., at least 20° C. and less than or equal to 55° C.). First or third temperatures described herein may each independently have a value in one or more of the above-referenced ranges.

Accordingly, in some embodiments, a method may involve a sample or reagent (or a channel, such as an incubation channel) having a first temperature (e.g., a temperature in one or more ranges described herein, including the temperatures noted above for the reduced temperatures). The sample or reagent may then be incubated at (or a channel may be exposed to) a second temperature, wherein the second temperature is greater than the first temperature. The second temperature may have a value as described herein for an incubation temperature. The sample or reagent (or a channel) may then have or be exposed to a third temperature, wherein the third temperature is less than the second temperature. The third temperature may be a temperature in one or more ranges described herein, including the temperatures noted above for the reduced temperatures. In some cases, the third temperature is the same as the first temperature, although different first and third temperatures are also possible. In some cases, for example, the third temper e is greater than t temperature, but is less than the second temperature.

As noted above, after the controlled incubation and/or mixing period the remaining portion of the sample may be flowed through the detection channel, which may be separate from or part of a detection zone as described herein. In some instances, the detection channel may comprise a reagent deposited on at least a portion of at least one surface of the detection channel. The reagent may interact (e.g., bind, react) with another reagent or sample component in the sample. From the detection channel, the sample may pass through other downstream components of the fluidic device including one or more analysis regions/reaction areas. Excess sample and/or other assay components (e.g., reagents) may be collected in waste chamber 40 of the fluidic device as illustrated in FIG. 1A.

Figure 3:
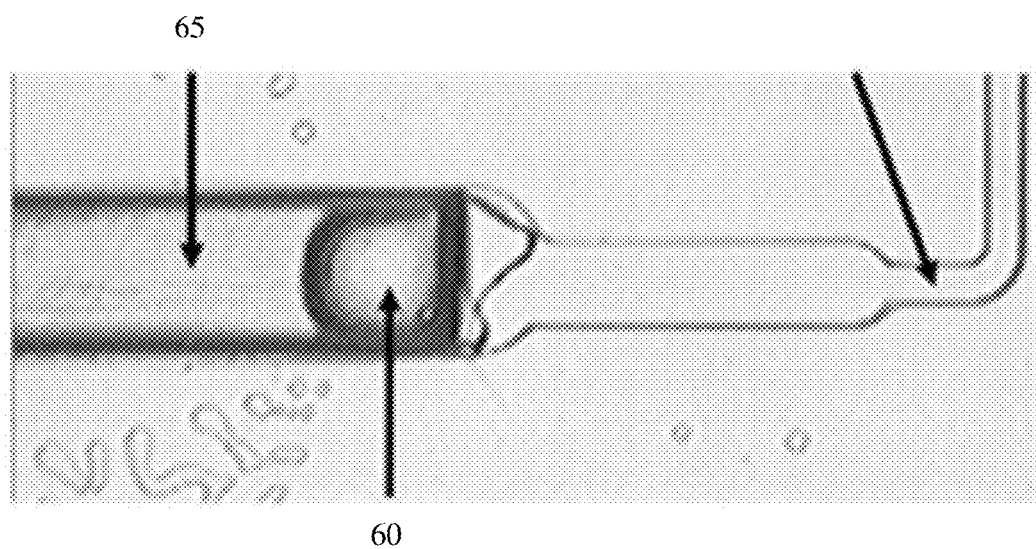
FIG. 3 is an image of a junction in a conventional fluidic device according to one set of embodiments.
Figure 4A:
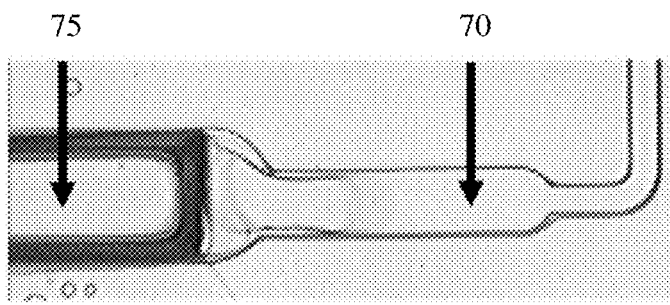
FIGS. 4A-D are images of fluid flow in a junction of a conventional fluidic device according to one set of embodiments.
Figure 4B:
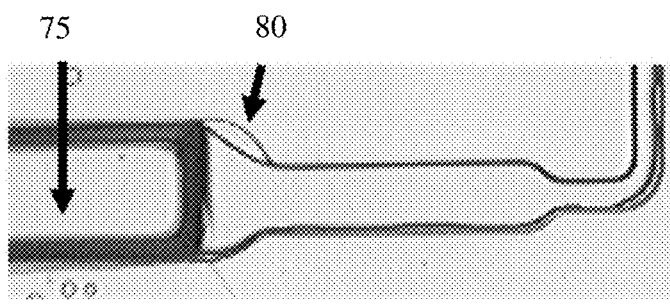
Figure 4C:
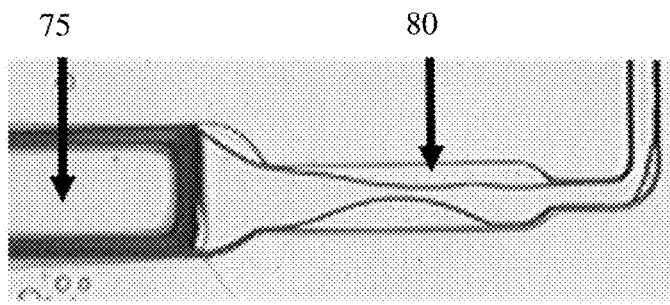
Figure 4D:
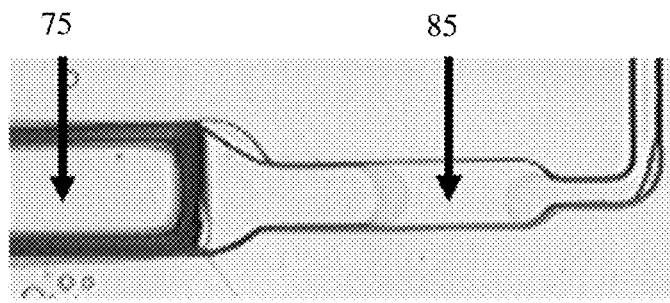

As described herein, the fluidic device may be configured to allow for controlled fluid handling without negatively affecting the operation of the fluidic device. For instance, fluid flow in the incubation channel may be ceased and restarted without clogging the channels in the fluidic device. In many conventional fluidic devices, transitions in channel geometry from large to small cross-sectional area, like the transition from the incubation channel to the detection channel in some embodiments described herein, may negatively affect operation of the fluidic device. For instance, in some embodiments in which the fluidic device is used for multi-phase fluid flow (e.g., gaseous plugs adjacent to liquid plugs) and includes a transition in the cross-sectional area of the channel, undesirable processes such as clogging, droplet formation, and/or trapping of fluid may occur. An example of clogging of a fluid at a geometrical transition is shown in FIG. 3. FIG. 3 shows an image of the junction of a channel having a large cross-sectional area adjacent to a channel having a small cross-sectional area. An air bubble 60 is trapped at the junction and acts as a clog preventing flow of a liquid 65. Air bubble 60 trapped at geometrical constriction can shed multiple air small bubbles (with a volume equal to a fraction of the trapped air bubble 60), resulting in a series of bubbles being present downstream of the constriction. Each air bubble present in the downstream channel will increase resistance to flow, and the presence of multiple air bubbles can, in some cases, reduce the flow rate to nearly no flow (e.g., they may cause the channel to clog). The change in geometry between the channel having a relatively large cross-sectional area and the channel having a relatively small cross-sectional area can be designed so that no air bubble would be trapped at the change in geometry.

FIG. 4 shows a sequence of images that illustrate droplet formation at a geometrical transition. FIG. 4A shows a liquid plug 70 downstream of a gas fluid plug 75. The liquid plug has entered the channel with the smaller cross-sectional area and the gas plug is beginning to enter the channel having the smaller cross-sectional area. As the liquid plug flow through this junction followed by the air plug 75, a small volume of liquid 80 is captured in the junction as shown in FIGS. 4B and 4C. As shown in FIG. 4D, this volume of liquid may serve as a source of droplets which form in the air flow, potentially causing analytical problems downstream. Moreover, trapped volume from multiple fluids can Mix at this junction, and combine to form droplets which might impact reactions downstream.

A fluidic device, as described herein, may be designed to avoid clogging, trapping one or more fluids, formation of air bubbles, and/or releasing a trapped fluid at inappropriate times. In some embodiments, a junction between an incubation channel and a detection channel may be configured to prevent these problems. For instance, in some embodiments, a fluidic device may include channels positioned on two sides of an article. The channels may be connected by an intervening channel, e.g., that passes through the thickness of the article used to form the channels of the fluidic device. An intervening channel refers to a channel that connects two channels lying on two different planes. The specific geometry of the channels and the positions of the channels within the fluidic devices described herein may allow clogging and/or trapping of one or more fluids to be avoided. For example, the presence of an intervening channel (e.g., that passes through the thickness of the article) may allow an incubation channel having a relatively large cross-sectional dimension to be fluidically connected to a detection channel having a relatively small cross-sectional dimension, without an abrupt change in cross-sectional dimensions of the channels that contributes to the clogging and/or trapping of fluids as shown in FIG. 3.

In some embodiments, channels (e.g., incubation channel, detection channel) having non-circular cross-sections are fabricated on the first and/or the second side of an article. The channels on the first side of the article are connected with channels on the second side of the article via intervening channels, which, in some embodiments, may have circular cross sections and can pass through the thickness of the article from the first side to the second side. In this way, each of the channels on the first side can be connected fluidically to the channels on the second side to form a single continuous channel. An advantage of such a configuration is that from a fabrication perspective, channels having non-circular cross sections can be easily fabricated on planar surfaces, and channels having circular cross sections can be easily fabricated in the form of through-holes between the two surfaces of an article.

Figure 5A:
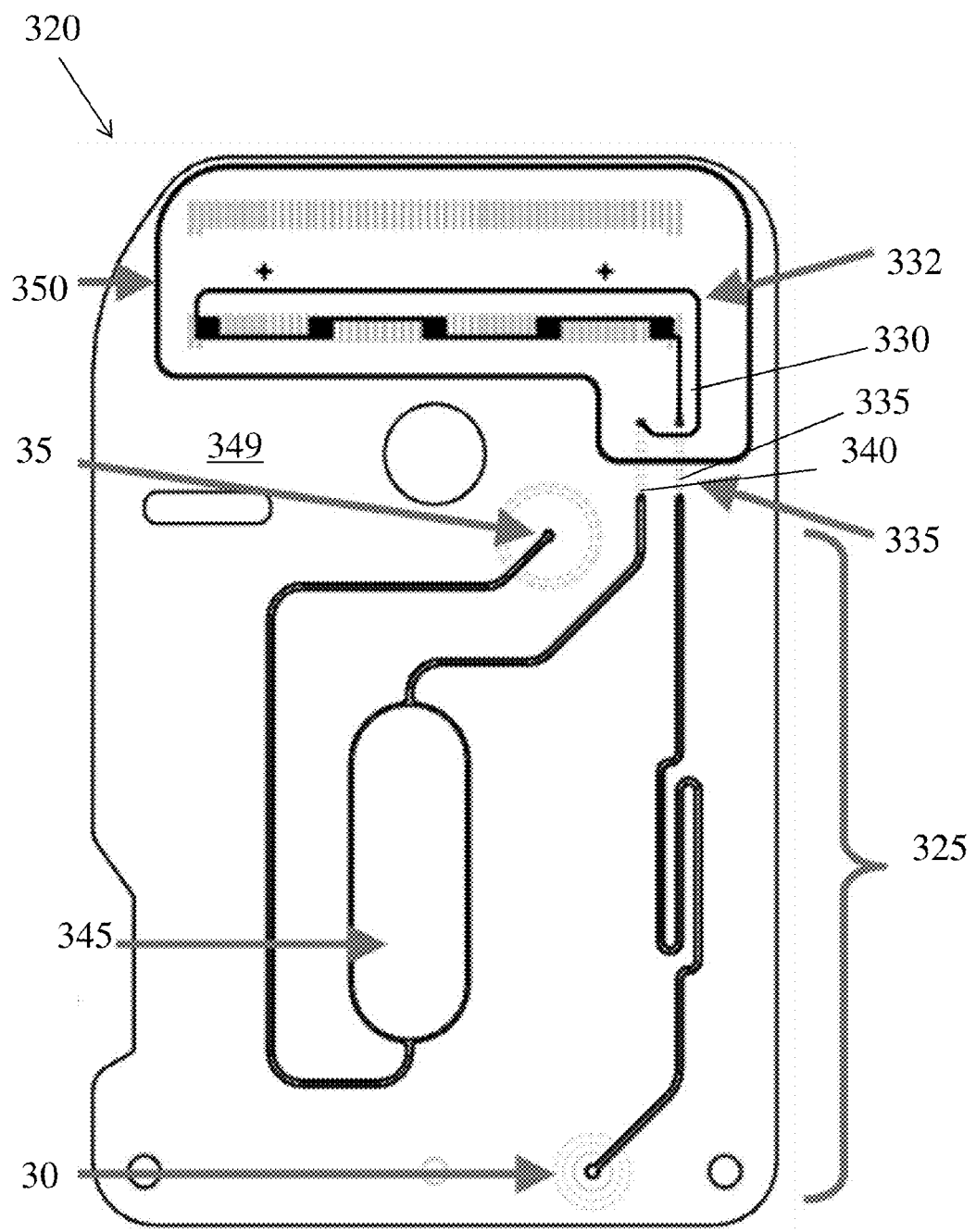
FIGS. 5A-C show (A) a fluidic device, (B) pieces used to form certain fluidic devices, and (C) a fluidic device according to certain embodiments.

Moreover, in some embodiments, the use of intervening channels may also simplify the fabrication of the fluidic device by, e.g., expanding the fabrications methods that can be utilized. For example, in embodiments in which the fluidic device is formed at least in part by injection molding, channels in a molded part are defined by a tool insert which contains the inverse features on its surface. For a given channel on a single surface of an article, it is often preferred that the features which define the channel are on a single monolithic piece (e.g., a single component or substrate). Crossing a channel across two pieces may be problematic. For instance, it may be difficult to line up features perfectly, resulting in channels which are imperfect. The interface between the two pieces may result in flash, where the molten material (e.g., plastic) used to form the article flows into any tiny gap between the pieces. Such flash may result in leaks in a finished article or otherwise impede the function of the article. An intervening channel can serve as a method to join two or more channels, each fabricated on different pieces, while avoiding problems with the interface of the pieces. FIG. 5A shows a fluidic device 320 where the relatively large channels (e.g., incubation channel 325 of the fluidic device are molded against one piece, e.g., piece 355 in FIG. 5B), yet the relatively small channels (e.g., detection channel 330 in detection zone 332), on the same surface, are molded against a separate piece (e.g., mounted within piece 350 in FIG. 5B). Thus, the device or substrate may include a first piece 349 and a second piece 350 that are formed from two different molds and attached to one another to form the channel system.

Figure 5B:
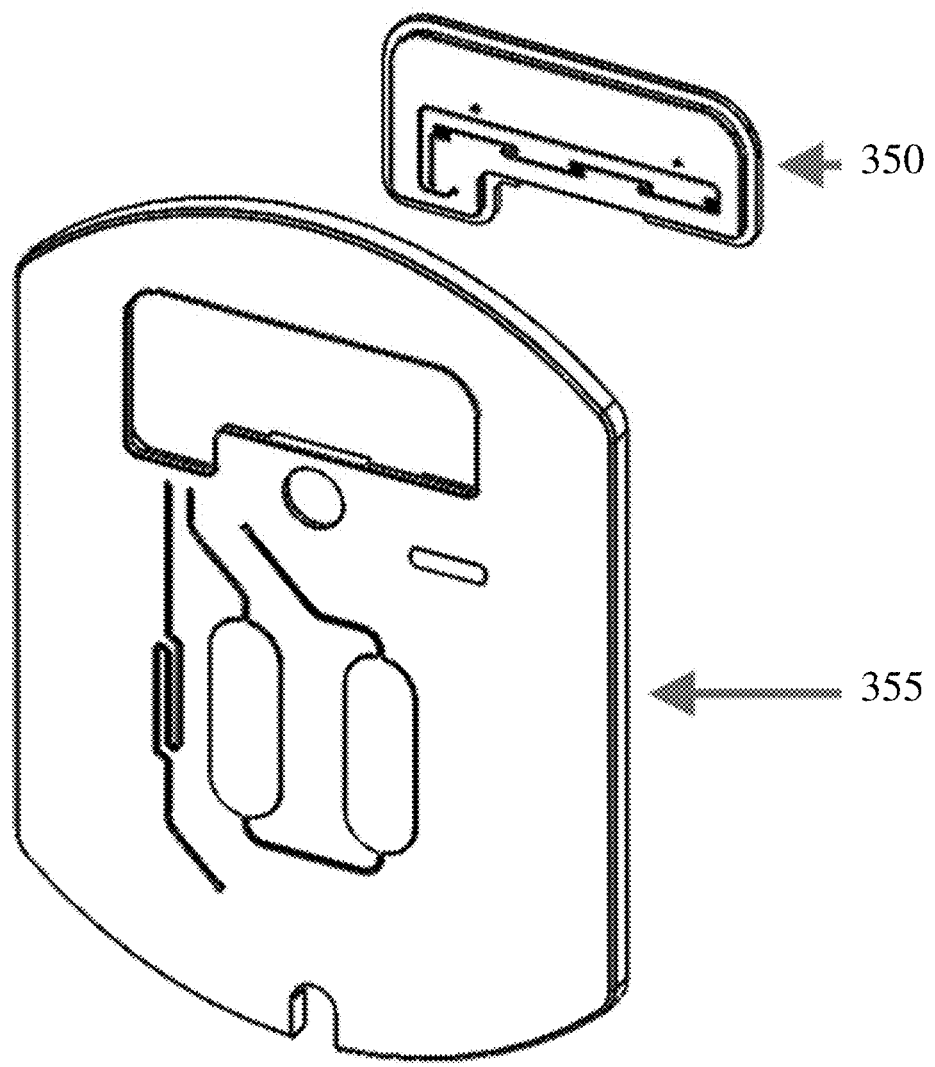

As shown illustratively in FIG. 5A, an intervening channel 335 connects the incubation channel with the detection channel. Another intervening channel 340 downstream of the analysis regions connects the small channels to the large outlet channel which leads to a waste zone 345. An advantage of this design is that different fabrication techniques can be used to make the two pieces. For example, certain fabrication techniques, such as lithography and etching, may be suitable for small features, but impractical for larger features or for features of multiple heights. Conversely, techniques such as mechanical milling may be well suited for larger features, but incapable of producing smaller features. FIG. 5B shows such two-part mold pieces that were used to produce the fluidic device shown in FIG. 5A.

In some embodiments, the incubation and detection channel are not on the same side of an article of the fluidic device. In some such embodiments, an intervening channel may form a bridge between an incubation channel (e.g., formed in a first surface of the article) and a detection channel (e.g., formed in a second surface of the article).

Figure 5C:
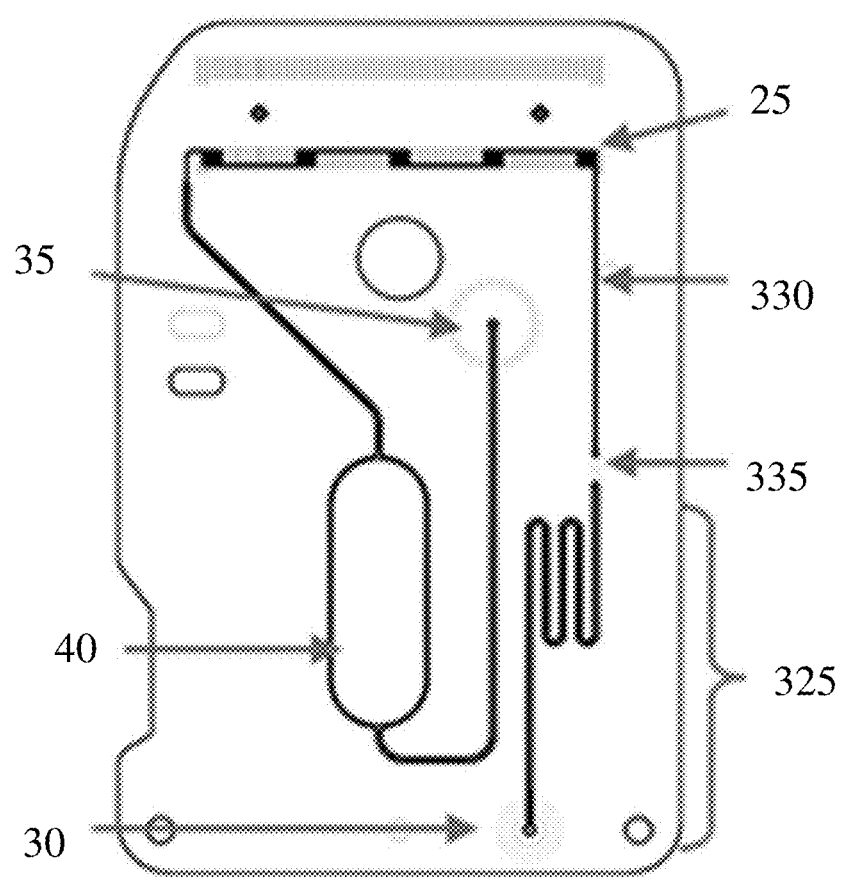

In another embodiment, both the incubation channel and the detection channel are formed on the same side of an article as shown in FIG. 5C (e.g., in a first surface of the article), and the channels are connected by an intervening channel 335 and a channel formed on the second surface of the article. The intervening channel and channel formed on the second surface of the article may act as bridging channels, e.g., channels that bridge the incubation channel and detection channel.

Figure 6:
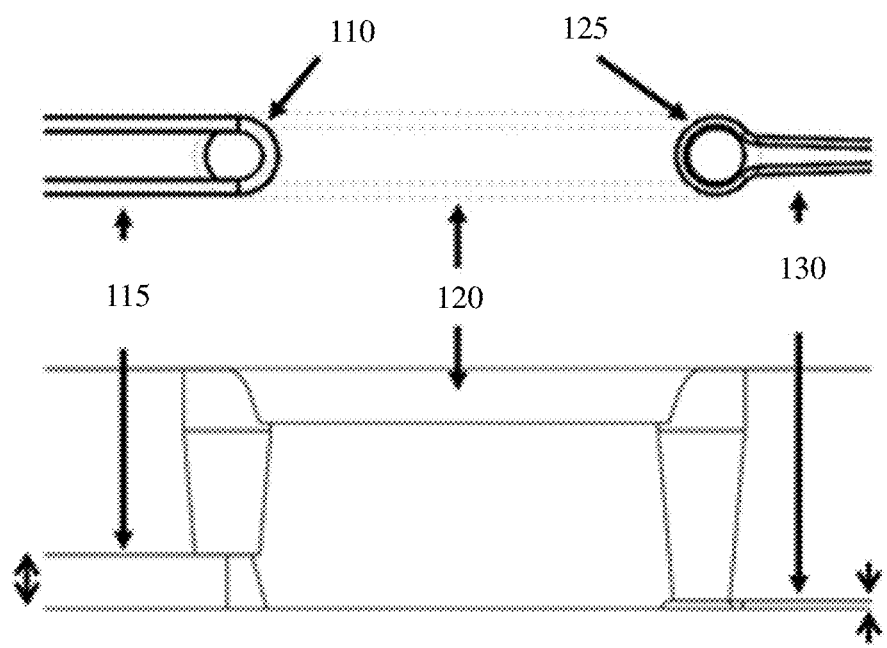
FIG. 6 shows a cross-section of a fluidic device comprising an intervening channel according to one set of embodiments.

A non-limiting example of a bridge is shown in FIG. 6 As shown in FIG. 6, the bridge may comprise a through-hole 110 (e.g., an intervening channel) that forms a non-zero angle (e.g., perpendicular to) with respect to the plane of an incubation channel 115, a bridging channel 120 on the opposite side of the article and substantially parallel to the incubation channel, and a through hole 125 (e.g., an intervening channel) from the bridging channel to the detection channel 130, which is on the same plane/side as the incubation channel. In some embodiments, one or more of the through-holes (e.g., an intervening channel) may have a substantially circular cross-section.

In some embodiments, the dimensions of the incubation channel and detection channel play a role in proper performance of the fluidic device. In some embodiments, the incubation channel may have a width of less than or equal to about 2 mm, less than or equal to about 3 mm, less than or equal to about 1 mm, less than or equal to about 750 microns, less than or equal to about 600 microns, less than or equal to about 500 microns, less than or equal to about 300 microns, or less than or equal to about 200 microns. In some instances, the incubation channel may have a width of greater than or equal to about 100 microns, greater than or equal to about 200 microns, greater than or equal to about 400 microns, greater than or equal to about 600 microns, greater than or equal to about 900 microns, greater than or equal to about 1 mm, or greater than or equal to about 1.5 mm. Combinations of the above-referenced ranges are also possible (e.g., greater than or equal to about 100 micron and less than or equal to about 2 mm).

In some embodiments, the incubation channel may have a height of less than or equal to about 2 mm, less than or equal to about 3 mm, less than or equal to about 1 mm, less than or equal to about 750 microns, less than or equal to about 600 microns, less than or equal to about 500 microns, less than or equal to about 300 microns, less than or equal to about 200 microns, or less than or equal to about 100 microns. In some instances, the incubation channel may have a height of greater than or equal to about 50 microns, greater than or equal to about 75 microns, greater than or equal to about 100 microns, greater than or equal to about 200 microns, greater than or equal to about 400 microns, greater than or equal to about 600 microns, greater than or equal to about 900 microns, greater than or equal to about 1 mm, or greater than or equal to about 1.5 mm Combinations of the above-referenced ranges are also possible (e.g., greater than or equal to about 50 micron and less than or equal to about 2 mm).

In some embodiments, the incubation channel may have a volume of at least about 0.001 mL, at least about 0.005 mL, at least about 0.01 mL, at least about 0.02 mL, at least about 0.03 mL, at least about 0.05 mL, at least about 0.08 mL, or at least about 0.01 mL. In some instances, the incubation channel has a volume less than or equal to about 1 mL, less than or equal to about 0.75 mL, less than or equal to about 0.5 mL, less than or equal to about 0.25 mL, or less than or equal to about 0.1 mL. Combinations of the above-referenced ranges are also possible.

In some embodiments, the detection channel may have a width less than or equal to about 300 microns, less than or equal to about 250 microns, less than or equal to about 200 microns, less than or equal to about 150 microns, less than or equal to about 100 microns, or less than or equal to about 75 microns. In some instances, the detection channel may have a width of greater than or equal to about 50 microns, greater than or equal to about 75 microns, greater than or equal to about 100 microns, greater than or equal to about 150 microns, greater than or equal to about 200 microns, or greater than or equal to about 250 microns. Combinations of the above-referenced ranges are also possible (e.g., greater than or equal to about 50 microns and less than or equal to about 300 microns).

In some embodiments, the detection channel may have a height of less than or equal to about 300 microns, less than or equal to about 250 microns, less than or equal to about 200 microns, less than or equal to about 150 microns, less than or equal to about 100 microns, less than or equal to about 75 microns, less than or equal to about 50 microns, or less than or equal to about 25 microns. In some instances, the detection channel may have a height of greater than or equal to about 10 microns, greater than or equal to about 15 microns, greater than or equal to about 25 microns, equal to about 50 microns, greater than or equal to about 75 microns, greater than or equal to about 100 microns, greater than or equal to about 150 microns, greater than or equal to about 200 microns, or greater than or equal to about 250 microns. Combinations of the above-referenced ranges are also possible (e.g., greater than or equal to about 10 microns and less than or equal to about 300 microns).

In some embodiments, the ratio of the height of the incubation channel to the detection channel may be at least about 1.5:1, at least about 2:1 (e.g., at least about 5:1, at least about 8:1, at least about 10:1, at least about 15:1, at least about 20:1, at least about 30:1, at least about 40:1, at least about 50:1). In some embodiments, the ratio of the height of the incubation channel to the detection channel may be less than or equal to about 1,000:1, less than or equal to about 750:1, less than or equal to about 500:1, less than or equal to about 400:1, less than or equal to about 300:1, less than or equal to about 200:1, less than or equal to about 100:1, less than or equal to about 50:1, less than or equal to about 10:1, or less than or equal to about 7:1. Combinations of the above-referenced ranges are also possible.

In some embodiments, the ratio of the width of the incubation channel to the detection channel may be at least about 1.5:1, at least about 2:1 (e.g., at least about 5:1, at least about 8:1, at least about 10:1, at least about 15:1, at least about 20:1, at least about 30:1, at least about 40:1, at least about 50:1). In some embodiments, the ratio of the width of the incubation channel to the detection channel may be less than or equal to about 1,000:1, less than or equal to about 750:1, less than or equal to about 500:1, less than or equal to about 400:1, less than or equal to about 300:1, less than or equal to about 200:1, less than or equal to about 100:1, less than or equal to about 50:1, less than or equal to about 10:1, or less than or equal to about 7:1. Combinations of the above-referenced ranges are also possible.

In certain embodiments, including an incubation channel having a height that is greater than the height of a detection channel can allow the volume of the incubation channel to be increased in a manner that would facilitate incubation and/or mixing within the incubation channel, compared to such a process in an incubation channel having the same or smaller height than that of the detection channel. It is often challenging to fabricate channels having different heights within the same substrate, especially using fabrication methods such as injection molding (e.g., using the same injection molding tool). One option for addressing this challenge is by separating the incubation channel from the detection channel using one or more intervening channels as described herein.

In some embodiments, the ratio of volume of the incubation channel to the detection channel is at least about 2:1 (e.g., at least about 5:1, at least about 8:1, at least about 10:1, at least about 15:1, at least about 20:1, at least about 30:1, at least about 40:1, at least about 50:1, at least about 100:1, or at least about 200:1). In some embodiments, the ratio of volume of the incubation channel to the detection channel is less than or equal to about 1,000:1, less than or equal to about 750:1, less than or equal to about 500:1, less than or equal to about 400:1, less than or equal to about 300:1, or less than or equal to about 200:1. Combinations of the above-referenced ranges are also possible.

As described herein, a biological and/or chemical assay may be performed in a fluidic device. In some embodiments, the assay may comprise an incubation step and/or mixing step. For instance, the assay may require the incubation and/or mixing of two or more assay components (e.g., sample and a reagent) under certain conditions (e.g., temperature, concentration, pH) for a specific period of time. In some such embodiments, the sensitivity and/or specificity of the assay may depend on achieving the requisite degree of incubation and/or mixing prior to another step in the assay process and/or arrival at another location in the fluidic device. For example, as shown illustratively in FIGS. 7-10, a sample may comprise an analyte that is bound or otherwise associated with a molecule in the sample. The association between the analyte and the molecule may interfere with the detection of the analyte. In some such cases, the analyte may be exposed to certain reagents and/or conditions to cause dissociation of the analyte and the molecule and/or prevent re-association. The exposure time may influence the amount of free analyte that is available for detection. In some embodiments, a fluidic device designed to allow for controlled incubation may have improved sensitivity and/or specificity compared to conventional fluidic devices.

A non-limiting example of an assay comprising an incubation step that may be performed in the fluidic device, as described herein, is shown in FIG. 7. In some embodiments, a sample 150 containing an analyte 155 associated with a molecule 160 may be analyzed in a fluidic device 140 comprising an incubation channel 165 in fluid communication with a reaction area/analysis region 170 comprising a binding partner 175 for the analyte. The assay may comprise incubating the sample with a reagent 180. The reagent may, for example, be capable of dissociating the analyte from the molecule. It should be appreciated, however, that the reagent may have different functions in other embodiments. For instance, in some embodiments, the reagent may be a component of an immune reaction (e.g., detector antibody), a component of a chemical reaction (e.g., reducing agent for a silver amplification reaction), a buffer, a diluent, a preservative for one or more component in the sample (e.g., anticoagulant), and/or combinations thereof.

In some instances, the reagent may be deposited on at least a portion of the surface of the incubation channel 165 as illustrated in FIG. 7A. The reagent may be deposited on the surface of the incubation channel prior to introduction of the sample into the device and/or may be stored in the incubation channel prior to first use. Introduction of sample or another liquid into the incubation channel may cause at least a portion of the reagent to be dissolved, reconstituted, and/or suspended in the sample as illustrated in FIG. 7B. In other embodiments, the sample or a liquid may be combined with the reagent during collection of the sample and/or prior to introduction of the sample or liquid into the incubation channel of the fluidic device. For instance, the reagent may be contained in the sample collector used to collect the sample and/or used to introduce the sample into the fluidic device (e.g., deposited on at least a portion of the surface of a channel within the sample collector). Regardless of when the reagent and the sample or another liquid are combined, incubation, e.g., of the sample and/or sample component and the reagent may occur in the incubation channel as shown in FIG. 7B.

As used herein, "prior to first use" of the device means a time or times before the device is first used by an intended user after commercial sale. First use may include any step(s) requiring manipulation of the device by a user. For example, first use may involve one or more steps such as puncturing a sealed inlet or removing a cover from an inlet to introduce a reagent into the device, connecting two or more channels to cause fluid communication between the channels, preparation of the device (e.g., loading of reagents into the device) before analysis of a sample, loading of a sample onto or into the device, preparation of a sample in a region of the device, performing a reaction with a sample, detection of a sample, etc. First use, in this context, does not include manufacture or other preparatory or quality control steps taken by the manufacturer of the device. Those of ordinary skill in the art are well aware of the meaning of first use in this context, and will be able easily to determine whether a device of the invention has or has not experienced first use. In one set of embodiments, devices of the invention are disposable after first use, and it is particularly evident when such devices are first used, because it is typically impractical to use the devices at all after first use.

In some embodiments, the incubation step may require the reagent to be incubated with the sample, a sample component, or a liquid for a certain period of time and/or under certain conditions (e.g., temperature). For example, as illustrated in FIG. 1C, the reagent may cause the analyte to be released from the molecule by competitively associating with the molecule. In some such embodiments, the substantial dissociation of the analyte from the molecule may require a certain amount of time. In some instances, the reagent may need to be incubated with the analyte at a specific temper or pH to increase the rate of dissociation and/or association. The incubation channel and/or feedback system may allow incubation to occur for a controlled period of time and/or temperature before a substantial portion of the sample reaches the incubation channel and/or is involved in a subsequent assay step as illustrated in FIG. 7C. After the desired incubation has occurred, the sample may flow to the reaction area, where the free analyte may bind to its binding partner.

In some embodiments, a fluidic device having an incubation channel may have a greater sensitivity and/or specificity to an analyte compared to an essentially identical fluidic device that lacks the incubation channel. For instance, FIG. 8 shows a schematic of the assay described above with respect to FIG. 7 performed in a fluidic device 190 that comprises a channel 195 and a reaction area 200 comprising a binding partner 205 for the analyte, but lacks an incubation channel. The reagent 180 may be deposited on at least a portion of a surface of the channel as shown in FIG. 8A. In some such cases, the reagent may be deposited at a location that is relatively close to the sample inlet. As in FIG. 7B, the sample may dissolve or suspend the reagent in at least a portion of the sample as illustrated in FIG. 8B. In certain embodiments, due to the lack of the incubation channel coupled with the feedback system in fluidic device 190, the sample may proceed toward and arrive at the reaction area more quickly than the fluidic device comprising an incubation channel as shown in FIG. 8C. In some such embodiments, little or no dissociation of the analyte and the molecule may have occurred by the time the sample reaches the reaction area as shown in FIG. 8D. In some embodiments, the flow rate in fluidic device 190 may not be able to be reduced to increase the duration of incubation due to issues with, e.g., clogging.

Another non-limiting example of an assay comprising an incubation step that may be performed in the fluidic device comprising an incubation channel is shown in FIG. 9. In some embodiments, a sample 215 containing an analyte 220 associated with a molecule 225 may be analyzed in a fluidic device 210 comprising a reaction area 230 comprising a binding partner 235 for the analyte downstream of the incubation channel 212. The association between the analyte and the molecule may prevent the analyte from binding with the binding partner in the reaction area. In some such embodiments, the sample may be flowed into the incubation channel, as shown in FIG. 9B, and exposed to certain conditions to cause the analyte to dissociate from the molecule. For instance, as illustrated in FIG. 9C, the sample or sample component may be incubated at a certain pH and/or temperature that cause the molecule to degrade or denature and thereby dissociate from the analyte. In some embodiments, once the requisite incubation has occurred, the at least one condition may be altered in or outside of the incubation channel. For instance, in embodiments in which the sample is incubated at a certain temperature, the heating of the sample in the incubation channel may cease after a predetermined temperature or period of time has been met. In embodiments in which at least one condition is a chemical property, the chemical property may be changed after sufficient incubation has occurred. For instance, a sample incubated at a certain pH may be mixed with an acid and/or base to alter the pH of the sample within the incubation channel and/or prior to the sample arriving at a downstream location such as the reaction area. Mixing of assay components in the incubation channel is described in more detail below. Regardless of whether the condition(s) that the sample is exposed to in the incubation channel are altered, after the incubation step, the free analyte may be flowed to the reaction area where the analyte can bind to its binding partner.

In some embodiments, the assay, described above with respect to FIG. 9, may have a reduced sensitivity and/or specificity when performed in an essentially identical fluidic device that lacks an incubation channel. For instance, FIG. 10 shows a schematic of the assay performed in a fluidic device 240 that comprises a channel 245 and a reaction area 250 comprising a binding partner 235 for the analyte, but lacks an incubation channel. In some such embodiments, the sample 215 containing the analyte 220 associated with the molecule 215 may be exposed to the certain conditions and flowed along the channel as shown in FIG. 10B. In certain embodiments, due to the movement of the sample and/or lack of an incubation channel, the exposure of the sample to the condition may be limited. For instance, the mobility of the sample may prevent sufficient heating of the sample due to the inability to locally heat a moving sample. In some embodiments in which at least one condition is a chemical property (e.g., pH, reagent concentration), the requisite exposure time may not be achieved because the sample may proceed toward and arrive at the reaction area relatively quickly compared to the fluidic device comprising incubation channel, as shown in FIG. 10C. The limited exposure of the sample to one or more condition may result in little or no dissociation of the analyte as shown in FIG. 10D. In some embodiments, prolonged exposure to certain conditions and/or or maintaining those conditions throughout the assay may negatively affect the sensitivity and/or specificity of the assay. For instance, the pH used to dissociate an analyte may negatively affect the binding of the analyte to the binding partner. In some instances, prolonged exposure of an analyte to certain pHs may lead to degradation or denaturation of the analyte.

As described herein, in some embodiments, e.g., for certain assays in which the sample is capillary whole blood drawn from a finger stick, venous whole blood, or other samples matrices, the temperature and duration of incubation may cause the leading edge of the sample to dry and/or coagulate and thereby present an obstacle to resuming the flow of the sample after incubation. In such cases, it may be desirable to position the sample in the device such that the sample's leading edge (e.g., the downstream-most sample/air interface) is positioned within a channel having a relatively larger cross-section, such as the incubation channel, during the incubation step. In some such embodiments, the relatively larger cross-sectional area (e.g., of the incubation channel) will present a lesser flow restriction upon resuming flow of the sample compared to a relatively smaller cross-sectional area. Referring to the device shown in FIG. 1A, the sample leading edge can be maintained within a larger channel during incubation by, for example, applying pre-determined vacuum or pressure levels for a pre-determined time to bring the majority of the sample into the incubation channel 15 but not reach the detection channel 20 or detection zone 25, as previously described. In the device shown in FIG. 1B, detection zone 27 within the incubation channel 15 would permit the sample to be detected when it reaches this location, and the vacuum or pressure levels can be modulated as previously described in order to maintain the sample within the incubation channel, but not reach portions of the detection channel in detection zone 25, during the incubation time.

Figures 11A, 11B, 11C, 11D, 11E:
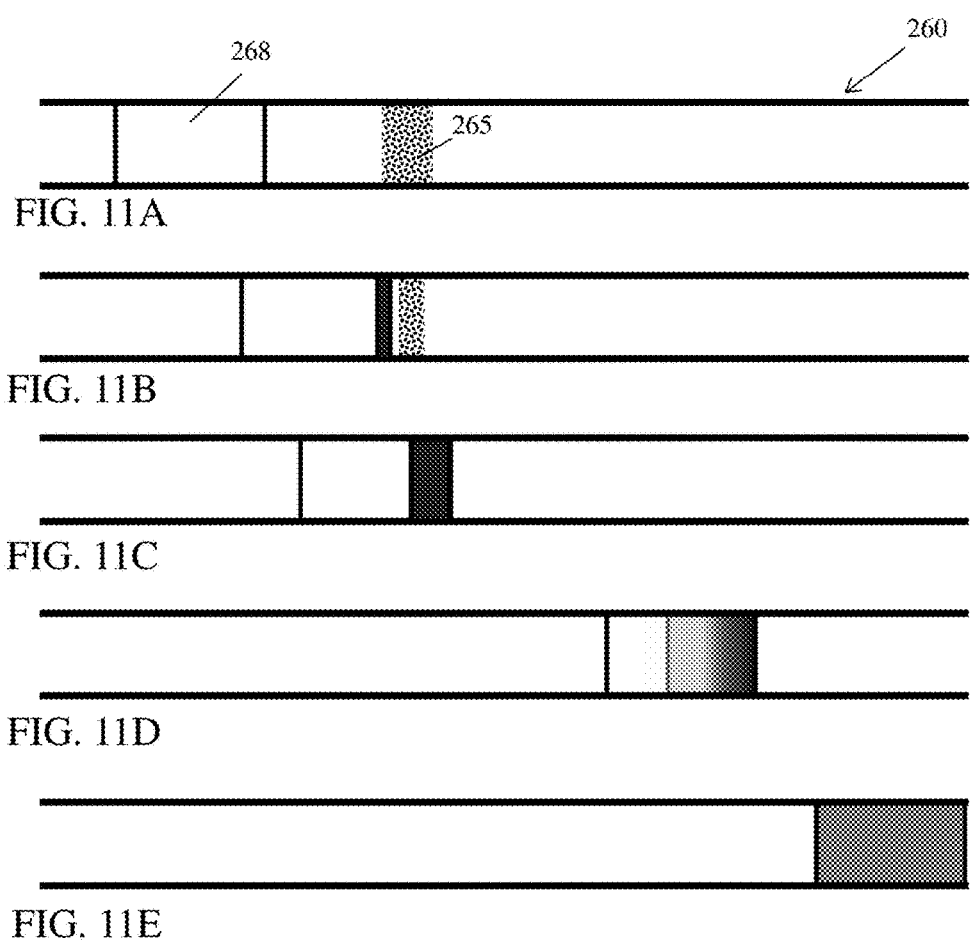
FIGS. 11A-11E show methods of mixing fluids in an incubation channel according to one set of embodiments.

In some embodiments, the incubation channel may be used to mix two or more assay components, as illustrated in FIG. 11. For instance, in some embodiments, a sample may be introduced into an incubation channel 260 having a reagent 265 deposited on at least a portion of a surface of the incubation channel as illustrated in FIG. 11A. The sample 268 may dissolve, reconstitute and/or suspend at least a portion of the reagent as it flows along the channel as illustrated in FIG. 11B. In some instances, a concentration gradient may exist within the sample after dissolving, reconstituting, or suspending the reagent as illustrated in FIG. 11C. The incubation channel may be designed to promote mixing, e.g., via diffusion as the sample flows along the channel as illustrated in FIG. 11D. In some embodiments, a substantially homogenous mixture of the sample and the reagent may exist prior to the sample plug exiting the incubation channel as illustrated in FIG. 11E.

In some embodiments, a method may involve mixing two or more fluids in the incubation channel of the fluidic device. In such embodiments, mixing may occur instead of or in addition to an incubation step described herein. Mixing may take place when at least some of the fluids are positioned in series in the incubation channel. For example, the fluids may be in the form of, for example, at least first, second and third fluid plugs, composed of first, second, and third fluids, respectively. The second fluid may be immiscible with the first and third fluids. In certain embodiments, the fluid plugs may be flowed in series in the incubation channel, e.g., in linear order. As the first fluid plug flows in the incubation channel, at least a portion of the first fluid may be removed from the first plug, thereby reducing the volume of the first fluid plug. For instance, portions of the first fluid (and/or components within the first fluid) may be deposited on the surface of the incubation channel during this flowing step. As the third fluid plug flows in the incubation channel, the third fluid may mix with portions of the deposited fluid to form a mixture of the first and third fluids in the third fluid plug. The mixing of fluids in a channel as described herein may allow for improved performance and simplification in the design and operations of fluidic devices that rely on mixing of fluids.

Another example of a method of mixing fluids in an incubation channel is shown in FIGS. 12A-12E. As shown illustratively in FIG. 12A, an incubation channel 270, including an upstream portion 272 and a downstream portion 274, may contain a first fluid plug 275 containing a first fluid 280, a second fluid plug 285 containing a second fluid 290, and a third fluid plug 295, containing a third fluid 300. As shown illustratively in this figure, the second fluid plug may be positioned between and directly adjacent to the first and third fluid plugs, although in other embodiments additional fluid plugs may be positioned between the first and third fluid plugs. In some embodiments, the second fluid may be immiscible with the first and third fluids, while the first and third fluids may optionally be miscible with one another. For example, the second fluid may be a gas (e.g., air) and the first and third fluids may be liquids. Other fluid plugs may also be present in the channel as described in more detail below.

As used herein, when a fluid or fluid plug is referred to as being "adjacent" another fluid or fluid plug, it can be directly adjacent the fluid or fluid plug, or an intervening fluid or fluid plug also may be present. A fluid or fluid plug that is "directly adjacent" or "in contact with" another fluid or fluid plug means that no intervening fluid or fluid plug is present.

Figure 12A:
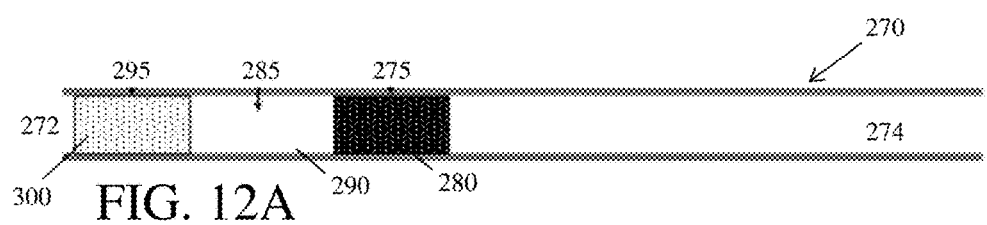
FIGS. 12A-12E show methods of mixing fluids in an incubation channel according to one set of embodiments.
Figure 12B:

As shown in FIG. 12B, the fluids may be flowed in series, e.g., from upstream to downstream in the direction of arrow 305. The incubation channel may be configured such that the flowing of the fluid plugs leads to the reduction of volume of the first fluid plug. For example, at least a portion of the first fluid (e.g., fluid portion 275) may deposit onto a surface of the incubation channel during fluid flow. Various channel configurations and methods for reducing the volume of the first fluid plug are described in more detail herein in U.S. Patent Publication No. 2014/0272935, filed Feb. 7, 2014, entitled "Mixing of Fluids in Fluidic Systems" [C1256.70011US01], which is incorporated by reference in its entirety. In certain embodiments in which the second fluid is immiscible with the first fluid, fluid portion 275 does not combine with the second fluid plug and as the second fluid plug flows in the channel. In embodiments in which the third fluid is miscible with the first fluid, the first and third fluids may combine to form a mixture 310 of at least portions of the two fluids, as shown illustratively in FIG. 12C.

Figure 12C:
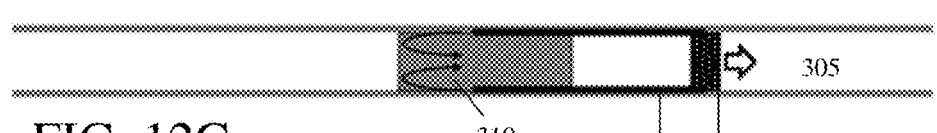

In some cases, as the first fluid plug flows, its volume may continue to reduce to a desired extent, for example, until mixture 310 includes a certain ratio of the first and third fluids, until a particular reduced volume of the first fluid plug has been reached, until a particular concentration of a component is present, or until a particular physical or chemical property is achieved. In some cases, the volume of the first fluid may be reduced by, for example, at least 50% as shown in FIG. 12C (or at least 25%, at least 75%, or at least 90%). In other cases, as shown illustratively in FIG. 12D, the entire volume of the first fluid plug may be reduced, such that only the second and third fluid plugs remain. The third fluid plug may then mix with the entire volume of the first fluid, as shown in FIG. 12E.

In some embodiments, the first and third fluids may contain a first and second component, respectively, for a chemical and/or biological reaction. In some cases, the first and second components are the same. In other embodiments, the first and second components are different. In some instances, a chemical and/or biological reaction involving the first and second components may be performed within the third fluid plug containing the mixture of the first and third fluids. For example, the first fluid may contain a silver salt and the third fluid may contain a reducing agent. The mixture of the first and third fluid may react with a reagent (e.g., gold colloids) to form detectable species (e.g., a silver film or particles that may be detected, for example, optically), as described in more detail below. Additional examples of chemical and/or biological reactions are described in more detail below. In certain embodiments, one or more fluid plugs contain a rinse solution, a diluent, a buffer, or a buffered reagent. Other types of fluids are also possible.

In some embodiment, mixing may occur between two or more assay components that are downstream (or upstream) of the sample. For instance, the incubation channel may contain a liquid plug and a reagent deposited on at least a portion of a surface of the incubation channel that were stored within the incubation channel prior to first use or prior to addition of the sample into the device. In some such embodiments, the deposited reagent may be downstream of the liquid plug. The liquid plug may dissolve, reconstitute, or suspend the deposited reagent and serve as a diluent for the deposited reagent. After the liquid plug has mixed with the deposited reagent, at least a portion of the liquid plug comprising the reagent, or the reagent itself, may be deposited on at least a portion of the surface of the incubation channel, as described above. The next liquid plug (e.g., the sample) may mix with the liquid containing the reagent that is deposited on the surface of the incubation channel.

As described herein, reagents (e.g., for a chemical and/or biological reaction) may be deposited in fluid and/or in dry form on one or more channel surfaces (e.g., incubation channel, detection channel, sample collector). In some embodiments, the reagent deposited on a surface of the sample collector or a surface of the fluidic device is present at the surface at a concentration of at least 50% (e.g., at least 60%, at least 70%, at least 80%, at least 90%, at least 95%) higher than a concentration of the reagent at another position within an interior of the sample collector or fluidic device. The deposited reagent may be associated with a fluidic device in any suitable manner. For example, reagents may be cross-linked, covalently bound, ionically bound, absorbed, adsorbed (physisorbed), or otherwise present on a surface within the fluidic device (e.g., in a channel of the device). In some embodiments, the reagent is a lyophilized reagent, a substantially dry reagent, a labelled reagent, a conditioning reagent, a pH modifier, a viscosity modifier, a blocking reagent, and/or a surfactant. In certain embodiments, the reagent is a reagent for a chemical and/or biological reaction (e.g., a binding reaction), a dye or otherwise optically detectable substance, or small particles. Non-limiting examples of reagents that may be deposited on a channel surface include anti-coagulants (e.g., heparin, dipyridamole, EDTA, citrate), surfactants, buffers, release/displacement agents (e.g., detergents, steroids like 2-bromoestradiol and danazol), proteins, small molecules, proteins (e.g. albumin), multivalent forms of small molecules (e.g., large molecule or protein labelled with more than one small molecules of interest, e.g., testosterone conjugate of bovine serum albumin with a 8:1 loading ratio), labelled version of the molecule to be analyzed in the sample (e.g., labelled forms of testosterone or other small molecules that can be measured by competitive immunoassays, see list below), labelled multivalent forms of small molecules (e.g., bovine serum albumin conjugated with multiple testosterone groups and at least one metal particle) and antibodies including non-labelled and labelled antibodies (e.g., anti-testosterone tracer monoclonal antibodies labeled with metal particles (e.g., nano-gold particles)). Small molecules that can be measured by competitive immunoassays include: testosterone, hydroxytestosterone, cortisol, dehydroepiandrosterone (DHEA), digoxin, estradiol, estrone, folate, progesterone, T3 or triiodothyronine, T4 or thyroxin, vitamins (A, B1, B12, B2, B3, B6, D, 25-OH-D, and/or E). In some embodiments, blocking reagents such as anti-species blocking agents (including HAMA blockers), bovine serum albumin (BSA), or any other scaffold molecule (a molecule or biochemical species that might be present in the solid phase to present a binding partner) can be included.

In some embodiments, a fluidic device for performing a testosterone assay is provided. Since testosterone exists in blood free and also bound to a binding protein, specifically, Sex Hormone Binding Globulin (SHGB), the fluidic device may test for to al testosterone, which includes the combination of both free and bound testosterone. The fluidic device may allow the bound testosterone in a sample to be released from the binding protein, such that all the testosterone remaining in the sample is free testosterone. This free testosterone may then be measured by a competitive assay in the device, whereby the testosterone in a sample competes with testosterone attached to a surface to bind with a labelled anti-testosterone antibody. After the competition, the sample is washed away, and the amount of labelled material attached to a surface of the device (e.g., at a detection zone) may be measured. In general, the higher the signal measured, the more labelled antibody has been captured at the surface and therefore less captured by testosterone in the sample, indicating a lower concentration of testosterone in the sample. For example, if silver amplification is used, an increase in optical density corresponding to silver formed on the gold attached to the captured anti-testosterone antibodies can be determined.

In another embodiment, a fluidic device may allow the bound testosterone in a sample to be released from the binding protein, such that all the testosterone remaining in the sample is free testosterone. This free testosterone may then be measured by a competitive assay, whereby the testosterone in a sample competes with labeled testosterone to bind with an anti-testosterone antibody attached to a surface of the device. After the competition, the sample is washed away, and the amount of labelled material attached to the surface of the device (e.g., at a detection zone) may be measured. The higher the signal measured, the more labelled testosterone has been captured at the surface and therefore less testosterone has been captured from the sample, indicating a lower concentration of testosterone in the sample.

In some embodiments, a reagent is stored in the fluidic device prior to first use and/or prior to introduction of a sample into the device. Reagents may be disposed in or at one or more sides of an article of a device. For example, a reagent may be disposed in the incubation channel on a first side of the article, while another reagent is positioned in the detection channel positioned at a second side of the article. In other embodiments, one or more reagents are disposed in at least a portion of an intervening channel. In certain embodiments, one or more channels of a fluidic device include a stored liquid reagent. Certain fluidic devices may be designed to include both liquid and dry reagents stored in a single article prior to first use and/or prior to introduction of a sample into the device.

In certain embodiments, a reagent that is present (e.g., deposited) on a surface of a channel is deposited during use of the device. In some embodiments, prior to first use of the device and/or prior to introduction of a sample into the device, the reagent is not present on a surface of the device. During use, a fluid containing the reagent is flowed, and the act of flowing the fluid (e.g., fluid plug) may cause the reagent to be deposited onto the surface as described herein.

In some embodiments in which a reagent is deposited prior to use, prior to introduction of the sample, or during use, a method may comprise depositing at least a portion of the sample on a surface of the sample collector and/or fluidic device, and mixing the deposited sample with a diluting reagent to form a mixed fluid, such that a concentration of a component of the sample in the mixed fluid is less than or equal to about 97%, less than or equal to about 95%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, less than or equal to about 10%; and/or at least about 0.1%, 1%, or 3%, of a concentration of the component of the sample prior to the depositing step. Combinations of the above-referenced ranges are also possible.

In some embodiments, the amount of mixing and/or the number of fluids plugs that are mixed together may be controlled by certain characteristics of the incubation channel. For instance, the geometry of the channel may be used to control mixing. Non-limiting examples of geometrical channel features that may influence mixing include cross-sectional shape, cross-sectional area, aspect ratio, hydraulic diameter, radius of curvature of internal corners, deviations in the channel (e.g., turns, bends), radius of curvature of deviations in the channel, and gradual and/or abrupt changes in channel geometry (e.g., changes in cross-section area). For instance, a channel cross-section with sharper corners may more readily facilitate removal of a fluid from a fluid plug (e.g., to cause the fluid or a reagent to be deposited on a channel surface) compared to a channel cross-section with blunt corners. In one example, a channel with a cross-section that includes a radius of curvature substantially smaller than the half-width and/or half-height of the channel may more readily facilitate removal of a fluid from a fluid plug compared to a channel cross-section that does not include such a radius of curvature, or a channel cross-section having a relatively larger radius of curvature. A radius of curvature substantially smaller than the half-width and/or half-height of the channel may be, for example, less than or equal to about 50%, less than or equal to about 40%, less than or equal to about 30%, less than or equal to about 20%, less than or equal to about 10%, or less than or equal to about 5% of the half-width and/or half-height of the channel. Additional examples of channel configurations and dimensions are provided in more detail below.

The length of the channel may also be used to control incubation and/or mixing. For example, longer channels may allow greater volume reduction of a fluid plug compared to a shorter channel, with all other factors being equal. In some cases, a channel that is substantially longer than the length occupied by the fluid plug may allow greater volume reduction of the fluid (e.g., the entire volume) than a channel that is not substantially longer than the length occupied by the fluid plug. In some instances, mixing and/or incubation may b controlled using more than one characteristic (e.g., cross-section shape and length.). Other methods of controlling mixing based on characteristics of the channel are also possible.

In some embodiments, the amount of mixing and/or the number of fluids plugs that are mixed together may be controlled by certain characteristics of a channel surface (e.g., surface roughness, surface texture, surface energy, surface polarity, surface charge, interfacial surface tension between the channel surface and a fluid, local variations in the characteristics of the channel surface). For instance, the surface roughness of a channel surface may be selected to facilitate or prevent removal of a fluid portion from a fluid plug. A channel surface with a higher surface roughness may more readily facilitate removal of a fluid portion from a fluid plug than a channel surface with a lower surface roughness.

In some instances, a fluidic device comprises a combination of two or more separate components (e.g., articles, layers, or fluidic devices) mounted together. Independent channel networks, which may optionally include reagents stored and/or sealed therein prior to first use, may be included on or in the different components of the fluidic device. The separate components may be mounted together or otherwise associated with one another by any suitable means, such as by the methods described herein, e.g., to form a single (composite) fluidic device. In some embodiments, two or more channel networks are positioned in different components, articles or layers of the fluidic device and are not connected fluidically prior to first use, but are connected fluidically at first use, e.g., by use of a sample connector. In some embodiments, two or more channel networks a positioned in different components, articles or layers of the fluidic device and are not connected fluidically prior to connection of a fluidic connector (and/or sample connector) to the components, articles or layers including the fluidic networks(s) of channels, but upon connection causes fluid communication between at least two channels on different components, articles or layers of the device.

Advantageously, each of the different components or layers that form a composite fluidic device may be tailored individually depending on the designed function(s) of that component or layer. For example, in one set of embodiments, one component of a composite fluidic device may be tailored for storing wet reagents. Additionally or alternatively, e.g., depending on the amount of fluids to be stored, the storage region(s) of that fluidic device may be made with larger (or smaller) cross-sectional dimensions than channels or regions of other components not used for storage of liquids. The material used to form the fluidic device may be compatible with fabrication techniques suitable for forming larger (or smaller) cross-sectional dimensions. By contrast, a second component that may be tailored for detection of an analyte, or a second component that may be tailored to include an incubation channel for incubation or mixing may, in some embodiments, include channel portions having relatively smaller (or larger) cross-sectional dimensions. Additionally or alternatively, a channel portion of the second component may have a lower (or higher) surface roughness compared to a channel portion of another component (e.g., a first component including a channel used for storage of a reagent). The cross sectional dimensions or surface roughness of the channel portions of the second component may, in certain embodiments, require a certain fabrication technique or fabrication tool different from that used to form a different component of the fluidic device. Furthermore, in some particular embodiments, the material used for the second component may be well characterized for protein attachment and detection. As such, it may be advantageous to form different channels used for different purposes on different components of a fluidic device, which can then be joined together prior to use by an intended user.

In some embodiments, a channel includes a feature on or in an article or substrate that at least partially directs the flow of a fluid. For instance, a feature that is formed in a surface or a side of an article or substantially embedded within the article may constitute a channel if it at least partially directs the fluid flow. An intervening channel refers to a channel that connects two channels lying on two different planes. In some embodiments, one or more channels are microfluidic.

Microfluidic may refer to a device, apparatus or system including at least one fluid channel having a cross-sectional dimension of less than 1 mm, and a ratio of length to largest cross-sectional dimension of at least 3:1. A microfluidic channel or fluidic channel may refer to a channel meeting these criteria. Though in some embodiments, devices described herein may be microfluidic, in certain embodiments, the systems and devices are not limited to microfluidic systems and may relate to other types of fluidic systems. Furthermore, it should be understood that all or a majority of the channels described herein may be microfluidic in certain embodiments. Non-microfluidic channels may also be used.

A cross-sectional dimension (e.g., a diameter, a height, and/or a width) of a channel described herein is measured perpendicular to the direction of fluid flow. Examples of cross-sectional dimensions are provided below.

It should be understood that a channel can have any suitable cross-sectional dimension, which may depend on, for example, where the channel is positioned in the device, how the channel is to be used (e.g., for mixing or for storage of reagents), the size of the fluidic device, the volume of reagents intended to flow in the device, etc. For instance, in some embodiments, a channel (e.g., an incubation channel, a detection channel, a channel used for storing a reagent, an intervening channel, a bridging channel, a channel of the sample collector) may have a maximum cross-sectional dimension (e.g., a width or height) of less than or equal to about 5 mm, less than or equal to about 3 mm, less than or equal to about 1 mm, less than or equal to about 750 microns, less than or equal to about 600 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, or less than or equal to about 5 microns. In some instances, a channel, or channel portion, may have a maximum cross-sectional dimension of greater than or equal to about 0.1 microns, greater than or equal to about 1 microns, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 400 microns, greater than or equal to about 600 microns, greater than or equal to about 900 microns, greater than or equal to about 1 mm, greater than or equal to about 1.5 mm, or greater than or equal to about 3 mm. Combinations of the above-referenced ranges are also possible (e.g., greater than or equal to about 1 micron and less than or equal to about 1 mm). Other values of maximum cross-sectional dimensions are also possible.

In some cases, at least one or at least two cross-sectional dimensions (e.g., a height and a width) of a channel (e.g., an incubation channel, a detection channel, a channel used for storing a reagent, an intervening channel, a bridging channel, a channel of the sample collector) may be less than or equal to about 2 mm, less than or equal to about 1 mm, less than or equal to about 750 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, or less than or equal to about 5 microns. In some instances, at least one or at least two cross-sectional dimensions of a channel may be greater than or equal to about 0.1 microns, greater than or equal to about 1 micron, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 400 microns, greater than or equal to about 600 microns, or greater than or equal to about 700 microns. Combinations of the above-referenced ranges are also possible (e.g., greater than or equal to about 10 µm and less than or equal to about 500 µm). Other values are also possible.

A channel (e.g., an incubation channel, a detection channel, a channel used for storing a reagent, an intervening channel, a bridging channel, a channel of the sample collector) may have a certain width-to-height ratio. In certain instances, the ratio of the width to height of a channel may be greater than or equal to about 1:1, greater than or equal to about 2:1, greater than or equal to about 5:1, greater than or equal to about 10:1, greater than or equal to about 15:1, or greater than or equal to about 20:1. In some instances the width-to-height ratio may be less than or equal to about 30:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

A channel (e.g., an incubation channel, a detection channel, a channel used for storing a reagent, an intervening channel, a bridging channel, a channel of the sample collector) may also have an aspect ratio (length to largest average cross-sectional dimension) of at least 2:1, more typically at least 3:1, 5:1, or 10:1. In some cases, a channel has a very large aspect ratios e.g., at least 100:1, 500:1 or 1000:1. In certain embodiments, a channel, has a length to largest width of less than or equal to 10, 7, 5, 3, or 2.

A channel may have a length and/or volume for mixing, incubation, and/or storage as described herein. In some embodiments a channel (e.g., an incubation channel, a detection channel, a channel used for storing a reagent, an intervening channel, a bridging channel, a channel of the sample collector) may have a volume of greater than or equal to about 0.001 picoliters, greater than or equal to about 0.01 picoliters, greater than or equal to about 0.1 picoliters, greater than or equal to about 1 picoliters, greater than or equal to about 10 picoliters, greater than or equal to about 100 picoliters, greater than or equal to about 0.001 microliters, greater than or equal to about 0.01 microliters, greater than or equal to about 0.1 microliters, greater than or equal to about 1 microliter, greater than or equal to about 10 microliters, greater than or equal to about 25 microliters, greater than or equal to about 50 microliters, greater than or equal to about 100 microliters, greater than or equal to about 150, or greater than or equal to about 200 microliters. In some instances, a channel, may have a volume of less than or equal to about 250 microliters, less than or equal to about 200 microliters, less than or equal to about 150 microliters, less than or equal to about 100 microliters, less than or equal to about 50 microliters, less than or equal to about 25 microliters, less than or equal to about 15 microliters, less than or equal to about 10 microliters, less than or equal to about 5 microliters, less than or equal to about 1 microliters, less than or equal to about 0.1 microliters, or less than or equal to about 0.01 microliters, less than or equal to about 0.001 microliter, less than or equal to about 100 picoliters, less than or equal to about 10 picoliters, less than or equal to about 1 picoliter, or less than or equal to about 0.1 picoliter, less than or equal to about 0.01 picoliter. Combinations of the above-referenced ranges are also possible (e.g., greater than or equal to about 0.001 picoliters and less than or equal to about 200 microliters). Other volumes are also possible.

In some embodiments, a channel (e.g., an incubation channel, a detection channel, a channel used for storing a reagent, an intervening channel, a bridging channel, a channel of the sample collector) may have a length of greater than or equal to about 1 mm, greater than or equal to about 5 mm, greater than or equal to about 10 mm, greater than or equal to about 20 mm, greater than or equal to about 40 mm, greater than or equal to about 60 mm, or greater than or equal to about 80 mm. In some instances, the length may be less than or equal to about 100 mm, less than or equal to about 90 mm, less than or equal to about 70 mm, less than or equal to about 50 mm, less than or equal to about 30 mm, or less than or equal to about 10 mm. Combinations of the above-referenced ranges are also possible (e.g., greater than or equal to about 1 mm and less than or equal to about 100 mm). Other values of length are also possible.

Some fluidic devices and articles are designed such that across-sectional dimension of an intervening channel, such as one that passes from a first surface to a second surface of an article, is within a certain range of a cross-sectional dimension of a non-intervening channel (e.g., an incubation channel, a detection channel, a bridging channel, a channel of the sample collector). In one particular embodiment, an intervening channel may have one or more cross-sectional dimensions (e.g., a smallest, largest, or average width or height) within a certain percentage of a cross-sectional dimension (e.g., a smallest, largest, or average width or height) of a channel directly connected to the intervening channel but which does not pass through the article from a first surface to a second surface.

In other cases, an intervening channel, such as one that passes from a first surface to a second surface of an article, has one or more cross-sectional dimensions within 40%, 30%, 20%, or 10% of the smallest width of a channel directly connected to the intervening channel (e.g., an incubation channel, a detection channel, a bridging channel, a channel of the sample collector). The channel that is directly connected to the intervening channel may optionally be formed in a surface of the article. Having an intervening channel with dimensions that are proportional to the dimensions of the channels in which the intervening channel is directly connected can reduce the number and volume of reagents and/or air bubbles that are trapped in the intervening channel during use of the device.

In some cases, an intervening channel has a volume less than or equal to one or more volumes of fluid reagents stored in the fluidic device prior to first use of the device. For instance, an intervening channel may have a volume that is less than or equal to 5, 3, 2, 1, 0.75, 0.5, or 0.25 times the volume of the largest volume of fluid reagent stored in a device prior to first use. In some instances, such configurations may facilitate transfer of fluids between channels so as to reduce or prevent fluids from being trapped in certain portions of the channels (e.g., at the connection between two channels).

In some cases, a channel (e.g., an intervening channel) that passes through the device from a first surface to a second surface of the article (e.g., through the thickness of the device) has a length the same as or substantially similar to the thickness of the article. The thickness of the article may depend on a variety of factors such as the material in which the article is formed, the fabrication technique, and the use of the channel (e.g., for storage of reagents or for detection). The article may have a thickness of for example, less than or equal to 3 mm, 10 mm, 8 mm, 5 mm, 3 mm, 2 mm, 1 mm or 0.5 mm, and/or at least 0.5 mm, 1 mm, 2 mm, 3 mm, 5 mm, 8, mm, or 10 mm. Accordingly, a channel that passes through the thickness of the device may have a same such length.

In some embodiments, a channel (e.g., an incubation channel, a detection channel, a channel used for storing a reagent, an intervening channel, a bridging channel, a channel of the sample collector) may include one or more corners (e.g., curved corners) having a certain radius of curvature. The curved corner may be, for example, a convex portion of a surface that mates with a cover. The convex portion of the surface may be formed during fabrication of the channel by various techniques (e.g., injection molding). In certain embodiments, a channel may include one or more corners (e.g., curved corners) having a radius of curvature of for example, less than or equal to about 100 µm, less than or equal to about 50 µm, less than or equal to about 30 µm, less than or equal to about 20 µm, less than or equal to about 10 µm, less than or equal to about 5 µm, less than or equal to about 3 µm, less than or equal to about 2 µm, less than or equal to about 1 µm, less than or equal to about 0.5 µm, or less than or equal to about 0.1 µm. In some embodiments, the radius of curvature of a curved corner of a channel may be, e.g., greater than or equal to about 0.1 µm, greater than or equal to about 0.5 µm, greater than or equal to about 1 µm, greater than or equal to about 2 µm, greater than or equal to about 3 µm, greater than or equal to about 5 µm, greater than or equal to about 10 µm, greater than or equal to about 20 µm, greater than or equal to about 30 µm, greater than or equal to about 50 µm, or greater than or equal to about 100 µm. Combinations of the above-noted ranges are also possible (e.g., a radius of curvature of greater than or equal to about 1 micron and less than or equal to about 20 microns). Other ranges are also possible. In some embodiments in which it is desirable to deposit a fluid or a reagent from a fluid plug onto a surface of a channel, a curved corner having a relatively smaller radius of curvature may increase the amount of fluid being deposited from the fluid plug flowing along a portion of the channel, compared to a fluid plug flowing in a channel having a relatively larger radius of curvature.

A channel (e.g., an incubation channel, a detection channel, a channel used for storing a reagent, an intervening channel, a bridging channel, a channel of the sample collector) having a substantially curved corner (e.g., a convex portion of a surface that mates with a cover) may have a ratio of a cross-sectional dimension (e.g., a width or a height) of the channel to the radius of curvature of the substantially curved corner (or convex portion) of at least 1:1, 2:1, 3:1, 5:1, 10:1, 20:1, 30:1, 50:1, 100:1, 200:1, or 500:1. In some embodiments, the ratio is less than or equal to 500:1, 200:1, 100:1, 50:1, 30:1, 20:1, 10:1, 5:1, 3:1, 2:1 or 1:1. Combinations of the above-referenced ranges are also possible. Other values are also possible.

It should be understood, that a channel (e.g., an incubation channel, a detection channel, a channel used for storing a reagent, an intervening channel, a bridging channel, a channel of the sample collector) may have any suitable cross-sectional shape and may be, for example, substantially-circular, oval, triangular, irregular, square, rectangular, trapezoidal, semi-circular, semi-ovular or the like.

A channel (e.g., an incubation channel, a detection channel, a channel used for storing a reagent, an intervening channel, a bridging channel, a channel of the sample collector) may have any suitable configuration. In some embodiments, a channel, may be a common channel, a branching channel, a channel on a side of a device that is separated from another channel by an intervening channel (e.g., a channel passing through the thickness of the device, as part of a two-sided device), or any other suitable configuration. In some cases, channels or channel portions may be separated from one another by a component (e.g., a vent valve or port), or may differ from one another based on a feature of the channel or portion (e.g., surface roughness, dimension, etc.). Other configurations are also possible.

A channel (e.g., an incubation channel, a detection channel, a channel used for storing a reagent, an intervening channel, a bridging channel, a channel of the sample collector) can be covered or uncovered. In embodiments where it is covered, at least one portion of the channel can have a cross-section that is substantially enclosed, or the entire channel may be substantially enclosed along its entire length with the exception of its inlet(s) and outlet(s). One or more inlet(s) and/or outlet(s) may also be enclosed and/or sealed. In certain embodiments, one or more covers is adapted and arranged such that a channel, an inlet, and/or an outlet is substantially enclosed and/or sealed prior to first use of the device by a user, but opened or unsealed at first use. In some embodiments, such a configuration may substantially prevent fluids and/or other reagents stored in the device from being removed from the device (e.g., due to evaporation) during fabrication, shipping, and/or storage of the device, as described herein.

Fluids can be flowed in a device described herein using any suitable method. In some embodiments, a fluidic device employs one or more valves (e.g., vent valves) to controllably flow and/or mix portions of fluid within the system. A vent valve can comprise, for example, a port in fluid communication with the channel in which a fluid is positioned, and may be actuated by positioning a seal over the port opening or by removing the seal from the port opening. In certain embodiments, the seal may include a valving mechanism such as a mechanical valve operatively associated with a tube in fluid communication with the port. Generally, opening the vent valve allows the port to function as a vent. When the port functions as a vent, the fluid located on one side of the vent valve flows, while the fluid located on the opposite side of the vent valve relative to the first fluid remains stationary. When the valve is closed, the port no longer functions as a vent, and the fluid located on both sides of the vent valve can flow through the system towards an outlet. Advantageously, fluid control such as a sequence of fluid flow and/or a change in flow rate can be achieved by opening and closing one or more vent valves and by applying a single source of fluid flow (e.g., a vacuum) operated at a substantially constant pressure. This can simplify the operation and use of the device by an intended user. Vent valves are described in more detail in U.S. Patent Publication No. 2011/0120562, filed Nov. 24, 2010 and entitled "Fluid Mixing and Delivery in Microfluidic Systems," which is incorporated herein by reference in its entirety for all purposes.

In some embodiments, when the fluid flow source is activated, one or more channels in the fluidic device may be pressurized (e.g., to approximately −30 kPa) which may drive the fluids within the channel toward the outlet. In some embodiments, fluids can be stored serially in a channel upstream of a vent valve positioned along the channel, and after closing the vent valve, the fluids can flow sequentially towards the channel outlet. In some cases, fluids can be stored in separate, intersecting channels, and after closing a vent valve the fluids can be flowed sequentially. The timing of delivery and the volume of fluid can be controlled, for example, by the timing of the vent valve actuation.

Advantageously, vent valves can b operated without constricting the cross-section of the microfluidic channel on which they operate, as might occur with certain valves in the prior art. Such a mode of operation can be effective in preventing leaking across the valve. Moreover, because vent valves can be used, some systems and methods described herein do not require the use of certain internal valves, which can be problematic due to, for example, their high expense, complexity in fabrication, fragility, limited compatibility with mixed gas and liquid systems, and/or unreliability in microfluidic systems.

It should be understood that while vent valves are described, other types of valving mechanisms can be used with the systems and methods described herein. Non-limiting examples of a valving mechanism which may be operatively associated with a valve include a diaphragm valve, ball valve, gate valve, butterfly valve, globe valve, needle valve, pinch valve, poppet valve, or pinch valve. The valving mechanism may be actuated by any suitable means, including a solenoid, a motor, by hand, by electronic actuation, or by hydraulic/pneumatic pressure.

In certain embodiments, one or more channels of a fluidic device include a stored liquid reagent (e.g., in the form of a fluid plug). In some cases, more than one liquid reagents (e.g., fluid plugs) are stored in a channel. The liquid reagents may be separated by a separation fluid, which may be immiscible with the liquid reagents. The fluid reagents may be stored in the device prior to first use, prior to introduction of a sample, or prior to forming a fluidic connection between two previously unconnected channels (e.g., using a fluidic connector). In other embodiments, a fluid reagent may be introduced into the device at first use. In some cases, the liquid reagents may be kept separate during storage of the fluids (e.g., while the device is sealed). During use of the device, at least portions of the liquids may be combined (e.g., mixed) using the methods described herein.

Certain fluidic devices may be designed to include both liquid and dry reagents stored in a single article prior to first use and/or prior to introduction of a sample into the device. In some cases, the liquid and dry reagents are stored in fluid communication with each other prior to first use. In other cases, the liquid and dry reagents are not in fluid communication with one another prior to first use, but at first use are placed in fluid communication with one another. For instance, one or more liquid reagents may be stored in a first common channel and one or more reagents stored in a second common channel, the first and second common channels not being connected or in fluidic communication with one another prior to first use, prior to introduction of a sample, or prior to forming a fluidic connection between the two common channels (e.g., using a fluidic connector). Additionally or alternatively, the reagents may be stored in separate vessels such that a reagent is not in fluid communication with the fluidic device prior to first use. The use of stored reagents can simplify use of the fluidic device by a user, since this minimizes the number of steps the user has to perform in order to operate the device. This simplicity can allow the fluidic devices described herein to be used by untrained users, such as those in point-of-care settings, and in particular, for devices designed to perform immunoassays.

In various embodiments involving the storage of fluid (e.g., liquid) reagents prior to first use, the fluids may be stored (and, in some embodiments, statically maintained without mixing) in a fluidic device for greater than 10 seconds, one minute, one hour, one day, one week, one month, or one year. By preventing contact between certain fluids, fluids containing components that would typically react or bind with each other can be prevented from doing so, e.g., while being maintained in a common channel. For example, while they are stored, fluids (e.g., in the form of fluid plugs) may be kept separated at least in part by immiscible separation fluids so that fluids that would normally react with each other when in contact may be stored for extended periods of time in a common channel. In some embodiments, the fluids may be stored so that they are substantially statically maintained and do not move in relation to their position in the channel. Even though fluids may shift slightly or vibrate and expand and contract while being statically maintained, certain fluidic devices described herein are adapted and arranged such that fluids in a common channel do not mix with one another during these processes.

Fluidic devices that are used for storage of one or more reagents e.g., prior to first use) may be stored at reduced temperatures, such as less than or equal to 10° C., 4° C., 0° C., or −10° C. Fluids may also be exposed to elevated temperatures such as greater than 25° C., greater than 35° C. or greater than 50° C. Fluids may be shipped from one location to the other by surface or air without allowing for mixing of reagent fluids contained in the channel. The amount of separation fluid may be chosen based on the end process with which the fluids are to be used as well as on the conditions to which it is expected that the fluidic device will be exposed. For example, if the fluidic device is expected to receive physical shock or vibration, fluids may only fill portions but not all of a channel. Furthermore, larger plugs of immiscible separation fluid may be used along with one or more channel configurations described herein. In this manner, distinct fluids within a channel system of a fluidic device may avoid mixing.

A fluidic device may include one or more characteristics that facilitate control over fluid transport and/or prevent fluids from mixing with one another during storage. For example, a device may include structural characteristics (e.g., an elongated indentation or protrusion) and/or physical or chemical characteristics (e.g., hydrophobicity vs. hydrophilicity) or other characteristics that can exert a force (e.g., a containing force) on a fluid. In some cases, a fluid may be held within a channel using surface tension (e.g., a concave or convex meniscus). For example, certain portions of a channel may be patterned with hydrophobic and hydrophilic portions to prevent movement and/or mixing of fluids during storage. In some cases, a common channel may have an absence of inner surfaces or other dividers to keep the fluids apart and fluids may be separated by a separation fluid.

In certain embodiments, the surface tension between a fluid and a channel surface may be selected as desired. In some cases, a wetting agent may be added to a fluid or fluid plug to control the surface tension. The wetting agent may be added, for example, prior to mixing, as a result of mixing, or as a result of a fluid being removed from a fluid plug. In certain cases, a wetting agent may be added to the channel surface to control surface tension, e.g., during manufacturing of the device, prior to fluid flow, and/or as a result of fluid flow. In general, any suitable wetting agent at any desired concentration may be used. Examples of suitable wetting agents include, but are not limited to, polyvinyl alcohol, non-ionic detergents (e.g., poly(ethylene oxide) derivatives like Tween 20 and Triton, fatty alcohols), anionic detergents (e.g., sodium dodecyl sulfate and related detergents with shorter or longer alkane chains such as sodium decyl sulfate, sodium dodecyl sulfate, or sodium octadecyl sulfate, or fatty acid salts), cationic detergents (e.g., quaternary ammonium cations such as cetyl trimethylammonium bromide), zwitterionic detergents (e.g., dodecyl betaine), detergents including carboxyl or amine oxide head groups and fluorinated or non-fluorinated carbon chain(s), perfluorodetergents (e.g., Capstone FS-10, perfluoroheptanoic acid, or perfluorooctanoic acid), low surface tension liquids (e.g., alcohols such as isopropanol or 1-butanol), and combinations thereof. In certain embodiments, a non-wetting agent (e.g., ionic compounds) may be added to increase the surface tension.

In embodiments in which a wetting agent is added to a fluid or fluid plug, the percentage (by weight/volume) of the wetting agent in the fluid or fluid plug may be greater than or equal to about 0.001%, greater than or equal to about 0.01%, greater than or equal to about 0.025%, greater than or equal to about 0.05%, greater than or equal to about 0.1%, areater than or equal to about 0.1%, greater than or equal to about 0.5%, greater than or equal to about 1%, greater than or equal to about 5%, greater than or equal to about 10%, greater than or equal to about 20%, greater than or equal to about 30%, greater than or equal to about 40%, or greater than or equal to about 40%. In some instances, the percentage of wetting aaent in the fluid or fluid plug may be less than or equal to about 75%, less than or equal to about 50%, less than or equal to about 40%, less than or equal to about 30%, less than or equal to about 20%, less than or equal to about 10%, less than or equal to about 5%, less than or equal to about 1%, less than or equal to about 0.5%, less than or equal to about 0.01%, or less than or equal to about 0.01%. Combinations of the above-referenced ranges are also possible (e.g., greater than or equal to about 0.01% or less than or equal to about 50%). Other ranges of wetting agent percentaaes are also possible.

Figure 12D:
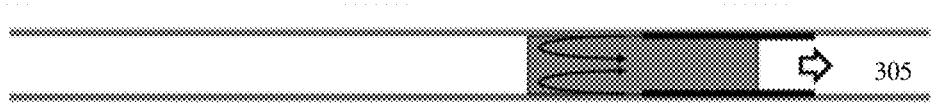
Figure 12E:
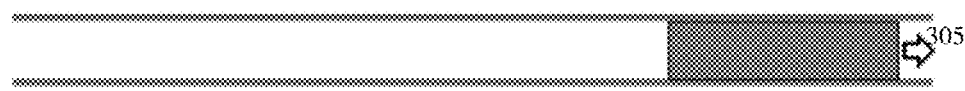

In certain cases, as shown in illustratively FIG. 12D the entire volume of a fluid (e.g., a first fluid, a second fluid) may be incorporated into one or more fluid plugs downstream such that the fluid plug is no longer present in the channel. In some cases, the volume of the fluid in the fluid plug may be reduced by a certain percentage (e.g., compared to the initial volume of the fluid plug). For instance, in some embodiments, the volume of a fluid plug may be reduced by greater than or equal to about 50%, greater than or equal to about 60%, greater than or equal to about 70%, greater than or equal to about 80%, greater than or equal to about 90%, or greater than or equal to about 95%. In some instances, the volume of a fluid in a fluid plug may be reduced by less than or equal to about 100%, less than or equal to about 90%, less than or equal to about 80%, less than or equal to about 70%, or less than or equal to about 60%. Combinations of the above-referenced ranges are also possible (e.g., greater than or equal to about 50% and less than or equal to about 100%). In some cases, 100% of the volume of the fluid is removed from a fluid plug, such that the fluid plug no longer remains in the system. In such embodiments, the fluid removed from the fluid plug may be entirely deposited or dispersed along or within the channel. In other embodiments, 0% of the fluid is removed from a fluid plug during fluid flow. Other values of volume reduction percentage are also possible. As described herein, in some embodiments the volume of more than one fluid plugs is reduced by the amounts noted above.

Detection of a sample in a fluidic device may have a variety of forms. In some cases, detection occurs continuously. In other embodiments, detection occurs periodically; and yet other embodiments, detection occurs sporadically. In some cases, detection occurs upon a specific event or condition taking place.

As described herein, detection can take place at any suitable position with respect to a fluidic device. In some cases, one or more detectors are stationery with respect to a fluidic device during use and/or during detection. For example, a stationery detector may be positioned adjacent a certain region of the fluidic device, such as a detection zone/detection channel, where one or more events (e.g., a chemical or biological reaction, introduction of a fluid into the zone/channel) may take place. The detector may detect, for example, the passing of fluids across the detection zone and/or analysis region. Additionally or alternatively, the detector may detect the binding or association of other components at that region (e.g., the binding of a component to surface of the analysis region). In some embodiments, stationery detector(s) may monitor multiple analysis regions within a detection zone simultaneously. For example, a detector such as a camera may be used to image an entire fluidic device, or large portion of the device, and only certain areas of the device scrutinized. Components such as optical fibers may be used to transmit light from multiple analysis regions to a single detector. In other embodiments, multiple detectors may each be aligned with an analysis region in a detection zone, as described in more detail in U.S. Pat. No. 8,501,416, issued Aug. 6, 2013 and entitled "Fluidic Structures Including Meandering and Wide Channels" [H0498.70244US01], which is incorporated herein by reference in its entirety.

A fluidic device, or portions thereof (e.g., a substrate, an article, a layer, a component), can be fabricated of any material suitable for forming a channel or other component. Non-limiting examples of materials include polymers (e.g., polypropylene, polyethylene, polystyrene, poly(styrene-co-acrylonitrile), poly(styrene-co-butadiene), poly(acrylonitrile, butadiene, styrene), poly(styrene-co-maleic anhydride), poly(styrene-co-acrylate), poly(styrene-co-methyl methacrylate), poly(methyl methacrylate), polycarbonate, poly(dimethylsiloxane), PVC, PTFE, PET, cyclo-olefin copolymer, or blends of two or more such polymers, or metals including nickel, copper, stainless steel, bulk metallic glass, or other metals or alloys, or ceramics including glass, quartz, silica, alumina, zirconia, tungsten carbide, silicon carbide, or non-metallic materials such as graphite, silicon, or others.

In certain embodiments in which a copolymer is used to form a component of a device described herein (e.g., a substrate, an article, a layer), the copolymer may include a first polymer component that is substantially non-reactive (e.g., a styrene-containing group, an acrylonitrile group, a butadiene group) and a second polymer component. In some embodiments, the second polymer component may be reactive (e.g., include reactive functional groups) for further functionalization (e.g., with a biomolecule (e.g. protein) or other entity that may be involved in, or associated with, an analysis to be performed). In other embodiments, the second polymer component may be non-reactive (e.g., does not include reactive functional groups). Non-limiting examples of second polymer components (e.g., that may be reactive) include anhydride-containing groups, such as maleic anhydride, ethyl maleic anhydride; maleimide-containing groups; amine-containing groups; aldehyde-containing groups; and acrylate-containing groups. Additional non-limiting examples of second polymer components (e.g., that are non-reactive) include acrylonitrile groups, butadiene groups, and methyl methacrylate groups. Such materials may be used to form a component of a device including, for example, an incubation channel, a detection channel, a channel used for storing a reagent, an intervening channel, a bridging channel, and/or a channel of the sample collector.

In embodiments in which a copolymer, such as one noted above, is used to form a component of a device described herein (e.g., a substrate, an article, a layer), the wt % of a first polymer component (e.g., styrene) in the copolymer may be, for example, at least 50 wt %, at least 60 wt %, at least 70 wt %, at least 80 wt %, at least 85 wt %, at least 87 wt %, at least 90 wt %, at least 92 wt %, at least 94 wt %, at least 96 wt %, or at least 98 wt %. The wt % of a first polymer component in the copolymer may be, in some embodiments, less than 100 wt %, less than or equal to 99 wt %, less than or equal to 95 wt %, less than or equal to 90 wt %, less than or equal to 80 wt %, less than or equal to 70 wt %, less than or equal to 60 wt %, or less than or equal to 50 wt %. Combinations of the above-referenced ranges are possible (e.g., at least 90 wt % and less than or equal to 99 wt %). Other ranges are also possible.

In embodiments in which a copolymer, such as one noted above, is used to form a component of a device described herein (e.g., a substrate, an article, a layer), the wt % of a second polymer component in the copolymer may be, for example, at least 2 wt %, at least 5 wt %, at least 8 wt %, at least 10 wt %, at least 12 wt %, at least 15 wt %, at least 20 wt %, at least 25 wt %, at least 28 wt %, at least 30 wt %, at least 35 wt %, at least 40 wt %, or at least 50 wt %. The wt % of a second polymer component in the copolymer may be, in some embodiments, less than or equal to 50 wt %, less than or equal to 40 wt %, less than or equal to 30 wt %, less than or equal to 25 wt %, less than or equal to 20 wt %, less than or equal to 15 wt %, less than or equal to 10 wt %, less than or equal to 8 wt %, or less than or equal to 5 wt %. Combinations of the above-referenced ranges are possible (e.g., at least 2 wt % and less than or equal to 30 wt %). Other ranges are also possible.

In certain embodiments in which a blend of two polymers or copolymers is used to form a component of a device described herein (e.g., a substrate, an article, a layer), the proportion of the first polymer or copolymer in the blend may be, for example, at least 50 wt %, at least 60 wt %, at least 70 wt %, at least 80 wt %, at least 90 wt %, at least 92 wt %, at least 94 wt %, at least 96 wt %, or at least 98 wt %. The wt % of a first polymer component in the copolymer may be, in some embodiments, less than 100 wt %, less than or equal to 99 wt %, less than or equal to 95 wt %, less than or equal to 90 wt %, less than or equal to 80 wt %, less than or equal to 70 wt %, less than or equal to 60 wt %, or less than or equal to 50 wt %. Combinations of the above-referenced ranges are possible (e.g., at least 90 wt % and less than or equal to 99 wt %). Other ratios are also possible. Blends of more than two polymers or copolymers are also possible.

The material forming the fluidic device and any associated components (e.g., a cover, a substrate, an article, a layer) may be hard or flexible. Those of ordinary skill in the art can readily select suitable material(s) based upon e.g., its rigidity, its inertness to (e.g., freedom from degradation by) a fluid to be passed throuah it its ability to be fitnctionalized (e.g., with a biomolecule (e.g. protein) or other entity that may be involved in, or associated with, an analysis to be performed), its robustness at a temperature at which a particular device is to be used, its transparency/opacity to electromagnetic waves (e.g., light in the ultraviolet and visible regions, terahertz waves, microwaves, and so on), its water vapor permeability, and/or the method used to fabricate features in the material. For insta molded or extruded articles, the material used may include a thermoplastic (e.g., polypropylene, polyethylene, polystyrene, poly(styrene-co-acrylonitrile), poly(styrene-co-butadiene), poly(acrylonitrile, butadiene, styrene), poly(styrene-co-maleic anhydride), poly(styrene-co-acrylate), poly(styrene-co-methyl methacrylate), poly(tnethyl methacrylate), polycarbonate, PVC, PTFE, cyclo-olefin polymers or copolymers, or blends of two or more such polymers), an elastomer (e.g., polyisoprene, isobutene-isoprene, nitrile, neoprene, ethylene-propylene, hypalon, poly(dimethylsiloxane), silicone), a thermoset (e.g, epoxy, unsaturated polyesters, phenolics), or combinations thereof. The article may be formed by injection molding in certain eMbodiments. In some embodiments, fluidic devices including two or more components, layers, or substrates may be formed in different materials to tailor the components to the major function(s) of the each of the components, e.g., based upon the factors described herein.

In some embodiments, a material used to forma fluidic device, or portions thereof (e.g., a substrate, an article, a layer, a component) may be chosen, at least in part, for its water vapor permeability. For instance, all or portions of a section or component of a device (e.g., a substrate, an article, a layer) may have a water vapor permeability of, for example, less than or equal to about 10.0 g·mm/m²·d, less than or equal to about 7.0 g·mm/m²·d, less than or equal to about 5.0 g·mm/m²·d, less than or equal to about 4.0 g·mm/m²·d, less than or equal to about 3.0 g·mm/m²·d, less than or equal to about 2.0 g·mm/m²·d, less than or equal to about 1.0 g·mm/m²·d, less than or equal to about 0.5 g·mm/m²·d, less than or equal to about 0.3 g·mm/m²·d, less than or equal to about 0.1 g·mm/m²·d, less than or equal to about 0.05 g·mm/m²·d, less than or equal to about 0.03 g·mm/m²·d, less than or equal to about 0.02 g·mm/m²·d, less than or equal to about 0.01 g·mm/m²·d, less than or equal to about 0.005 g·mm/m²·d, less than or equal to about 0.001 g·mm/m²·d, or less than or equal to about 0.0005 g·mm/m² d. In some embodiments, the water vapor permeability may be at least 0.001 g·mm/m²·d, at least 0.01 g·mm/m²·d, at least 0.02 g·mm/m²·d, at least 0.05 g·mm/m²·d, at least 0.1 g·mm/m²·d, at least 0.3 g·mm/m²·d, at least 0.5 g·mm/m²·d, at least 1.0 g·mm/m²·d, at least 2.0 g·mm/m²·d, at least 3.0 g·mm/m²·d, at least 4.0 g·mm/m²·d, at least 5.0 g·mm/m²·d, or at least 10.0 g·mm/m²·d. In some cases, the water vapor permeability may be, for example, between about 0.001 g·mm/m²·d and 0.01 g·mm/m²·d, between about 0.01 g·mm/m²·d and about 2.0 g·mm/m²~d, between about 0.01 g·mm/m²·d and about 1.0 g·mm/m²·d, between about 0.01 g·mm/m²·d and about 0.4 g·mm/m²·d, between about 0.01 g·mm/m²·d and about 0.04 g·mm/m²·d, or between about 0.01 g·mm/m²·d and about 0.1 g·mm/m²·d. Combinations of the above-referenced ranges are also possible. Other ranges are also possible. The water vapor permeability may be measured at, for example, 40° C. at 90% relative humidity (RH). It should be appreciated that different portions of a device (e.g., substrates, articles, layers, components) may have different combinations of the above-references ranges for water vapor permeability. In some embodiments, a material having a water vapor permeability in one or more of the above-referenced ranges may be used to form a component of a device including, for example, an incubation channel, a detection channel, a channel used for storing a reagent, an intervening channel, a bridging channel, and/or a channel of the sample collector.

In some embodiments, a material used to form a fluidic device, or portions thereof (e.g., a substrate, an article, a layer, a component) may be chosen, at least in part, for its optical transmission. For instance, all or portions of a section or component of a device (e.g., a substrate, an article, a layer) may have an optical transmission of at least 90% between 400 and 800 nm wavelengths of light (e.g., light in the visible range). Optical transmission may be measured through a material having a thickness of, for example, at least about 2 mm (or in other embodiments, at least about 1 mm or at least about 0.1 mm). In some instances, the optical transmission may be at least 80%, at least 85%, at least 88%, at least 92%, at least 94%, or at least 96% between 400 and 800 nm wavelengths of light. In certain embodiments, the optical transmission may be less than 100%, less than or equal to 98%, less than or equal to 96%, less than or equal to 94%, less than or equal to 92%, less than or equal to 90%, less than or equal to 85%, less than or equal to 80%, less than or equal to 50%, less than or equal to 30%, or less than or equal to 10% between 400 and 800 nm wavelengths of light. Combinations of the above-referenced ranges are possible. Other values are also possible. It should be appreciated that different portions of a device (e.g., substrates, articles, layers, components) may have different combinations of the above-references ranges for optical transmission. In some embodiments, a material having an optical transmission in one or more of the above-referenced ranges may be used to form a component of a device including, for example, an incubation channel, a detection channel, a channel used for storing a reagent, an intervening channel, a bridging channel, and/or a channel of the sample collector.

In some embodiments, a fluidic device, or portions thereof (e.g., a substrate, an article, a layer, a component) may be formed in a material that makes it more suitable for processing under certain conditions. For example, a material may be chosen in part based on its melting temperature to allow it to be compatible with certain fabrication tools and/or methods (e.g., for forming channels of certain dimensions) such as those described herein. In some embodiments, a fluidic device, or portions thereof (e.g., a substrate, an article, a layer, a component) may be formed in a material having a melting temperature of at least about 80° C., at least about 100° C., at least about 130° C., at least about 160° C., or at least about 200° C. In certain embodiments, the material may have a melting temperature of less than or equal to about 200° C., less than or equal to about 160° C., less than or equal to about 130° C., less than or equal to about 100° C., or less than or equal to about 80° C. Other melting temperatures are also possible. It should be appreciated that different portions of a device (e.g., substrates, articles, layers, components) may have different combinations of the above-references ranges for melting temperature. In some embodiments, a material having a melting temperature in one or more of the above-referenced ranges may be used to form a component of a device including, for example, an incubation channel, a detection channel, a channel used for storing a reagent, an intervening channel, a bridging channel, and/or a channel of the sample collector.

In some embodiments, a fluidic device, or portions thereof (e.g., a substrate, an article, a layer, a component) may be formed in a material having a certain glass transition temperature ($T_g$). For instance, in some embodiments, the glass transition temperature of a material may be greater than or equal to about 75° C., greater than or equal to about 80° C., greater than or equal to about 85° C., greater than or equal to about 90° C., greater than or equal to about 95° C., greater than or equal to about 100° C., greater than or equal to about 105° C., greater than or equal to about 110° C., greater than or equal to about 115° C., greater than or equal to about 120° C., greater than or equal to about 125° C., greater than or equal to about 130° C., greater than or equal to about 135° C., greater than or equal to about 140° C., greater than or equal to about 150° C., greater than or equal to about 160° C., greater than or equal to about 170° C. In some instances, the glass transition temperature of a material may be less than or equal to about 170° C., less than or equal to about 160° C., less than or equal to about 150° C., less than or equal to about 140° C., less than or equal to about 130° C., less than or equal to about 120° C., less than or equal to about 110° C., less than or equal to about 100° C., less than or equal to about 90° C., less than or equal to about 80° C., or equal to about 70° C. Combinations of the above-referenced ranges are also possible (e.g., greater than or equal to about 80° C. and less than or equal to about 140° C.). Other values of glass transition temperature of the first component are also possible. The glass transition temperature of a material may be determined using differential scanning calorimetry (DSC), thermomechanical analysis (TMA), dynamic mechanical analysis (DMA), or may be obtained from a manufacturer's specifications.

In some instances, a fluidic device is comprised of a combination of two or more materials, such as the ones listed above. For instance, channels of the fluidic device may be formed in polystyrene or other polymers (e.g., by injection molding) and a biocompatible tape may be used to seal the channels. The biocompatible tape or flexible material may include a material known to improve vapor barrier properties (e.g., metal foil, polymers or other materials known to have high vapor barriers), and may optionally allow access to inlets and outlets by puncturing or unpeeling the tape. A variety of methods can be used to seal a microfluidic channel or portions of a channel, or to join multiple layers of a device, including but not limited to, the use of adhesives, use adhesive tapes, gluing, solvent bonding, plasma-activated thermal bonding, UV-activated thermal bonding, welding, brazing, lamination of materials, or by mechanical methods (e.g., clamping, snapping mechanisms, etc.).

The choice of the bonding technique can be influenced by the temperature at which the device will be exposed during storage and operation. Adhesives and glues may flow and produce interference with the flow of sample and/or reagents on devices, when exposed to elevated temperatures, especially during the operation of the device when pressure difference are applied between the microfluidic channels and the ambient conditions. Application of vacuum in the channels may result in flow of adhesive (or glue) from the interface between two surfaces towards the microfluidic channels, and interfere with the flow. Application in the channels of a pressure greater than ambient pressure may result in delamination of the cover in the vicinity of the channels and erratic flow performances. Accordingly, one or more of these factors may be considered when choosing appropriate materials and/or methods for forming the fluidic device. For example, in some embodiments involving heating of the device, microfluidic channels may be covered with an adhesive-free lid/cover using solvent bonding.

In some embodiments, a first material used to form a first portion of a fluidic device (e.g., a substrate, an article, a layer) may include a channel (e.g., an incubation channel, a detection channel, a channel used for storing a reagent, an intervening channel, a bridging channel, and/or a channel of a sample collector) having one or more corners (e.g., curved corners) having a particular radius of curvature, such as a radius of curvature within one or more of the ranges noted above. In certain embodiments, the first material may be a copolymer described herein (and in particular, may include a first polymer component and a second polymer component as described above), and the channel may have a radius of curvature within one or more of the ranges noted above. In some instances involving a material having first and second polymer components, the second polymer component includes a reactive group for further functionalization of the first material. The second polymer component may be functionalized with, for example, a biomolecule (e.g. protein) or other entity that may be involved in, or associated with, an analysis to be performed. In certain embodiments, the first material may have an optical transmission as described herein, e.g., 90% between 400 nm and 800 nm wavelengths of light. In some instances, the first portion of the fluidic device (e.g., a substrate, an article, a layer) is formed by a molding process (e.g., injection molding). The first portion of the fluidic device may mate with a cover (e.g., a first cover layer), which may be used to enclose a channel of the first portion of the fluidic device. Other configurations are also possible.

In some embodiments, a second material used to form a second portion of a fluidic device (e.g., a substrate, an article, a layer) may have a water vapor permeability of less than about 0.05 g·mm/mm²·d. The second portion of the fluidic device may include a channel (e.g., an incubation channel, a detection channel, a channel used for storing a reagent, an intervening channel, a bridging channel, and/or a channel of a sample collector) having one or more corners (e.g., curved corners) having a particular radius of curvature, such as a radius of curvature within one or more of the ranges noted above. The second portion of the fluidic device may mate with a cover (e.g., a second cover layer), which may be used to enclose a channel of the second portion of the fluidic device. Other configurations are also possible.

In some embodiments, the first material may have a water vapor permeability higher than the water vapor permeability of the second material.

In some embodiments, the first material may have a glass transition temperature higher than the glass transition temperature of the second material. In other embodiments, the first material may have a glass transition temperature low than the glass transition temperature of the second material.

In one particular set of embodiments, the first material is used to form a first layer of a fluidic device, and the second material is used to form a second layer of the fluidic device. The first and second layers may be integrally connected to one another in some embodiments. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, or separating components fastened together via adhesives or tools. Integrally connected components may be irreversibly attached to one another during the course of normal use e.g., by use of an adhesive or by other bonding methods. In other embodiments, two or more layers may be reversibly attached to one another.

The methods and systems described herein may involve variety of different types of analyses, and can be used to determine a variety of different samples. In some cases, an analysis involves a chemical and/or biological reaction. In some embodiments, a chemical and/or biological reaction involves binding. Different types of binding may take place in fluidic devices described herein. Binding may involve the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones, and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

In some embodiments, a chemical and/or biological reaction involves a reducing agent (e.g., hydroquinone, chlorohydroquinone, pyrogallol, metol, 4-aminophenol and phenidone, Fe(+2), Ti(+3), and V(+2)). In some cases, a chemical and/or biological reaction involves a metal precursor (e.g., a solution of a metal salt, such as a silver salt or gold salt).

In some cases, a heterogeneous reaction (or assay) may take place in a fluidic device; for example, a binding partner may be associated with a surface of a channel, and the complementary binding partner may be present in the fluid phase. Other solid-phase assays that involve affinity reaction between proteins or other biomolecules (e.g., DNA, RNA, carbohydrates), or non-naturally occurring molecules (e.g., aptamers, or peptoids), can also be performed. In some embodiments, a binding partner may include a biomolecule such as an antibody, a small molecule attached to an antibody, bovine serum albumin or other protein, and/or an antigen such as a cell surface protein and peptide, the binding partner may be attached, in some embodiments, to a surface of a channel, e.g., by reaction with a second polymer component described herein. Non-limiting examples of typical reactions that can be performed in a fluidic device include chemical reactions, enzymatic reactions, immuno-based reactions (e.g., antigen-antibody), and cell-based reactions.

A biomolecule or other entity can be associated with a surface of the fluidic device (e.g., a surface of a channel) in any suitable manner. For example, a biomolecule or other entity may be cross-linked, covalently bound, ionically bound, absorbed, adsorbed (physisorbed), or otherwise present on a surface and/or within the fluidic device (e.g., in a channel of the device). In some embodiments, the biomolecule or other entity is a lyophilized molecule, a substantially dry molecule, a labelled molecule, a conditioning molecule, a pH modifier, a viscosity modifier, and/or a surfactant. In certain embodiments, the biomolecule or other en is a reagent for a chemical and/or biological reaction (e.g., a binding reaction), or a linker for such a reagent.

Non-limiting examples of analytes that can be determined (e.g., detected) using fluidic devices described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; autoantibodies; human and animal hormones, e.g., thyroid stimulating hormone (TSH), thyroxine (T4), vitamin D, vitamin B12, luteinizing hormone (LH), follicle-stimulating hormones (FSH), testosterone, progesterone, human chorionic gonadotropin, estradiol; other proteins or peptides, e.g. troponin I, troponin T, c-reactive protein, myoglobin, brain natriuretic protein, prostate specific antigen (PSA), free-PSA, intact PSA, complexed-PSA, pro-PSA, EPCA-2, PCADM-1, ABCA5, free-hK2, total hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell surface material. Chemicals that may be detected include explosives such as TNT, nerve agents, and environmentally hazardous compounds such as polychlorinated biphenyls (PCBs), dioxins, hydrocarbons, and MTBE. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte.

In some embodiments, one or more reagents that can be used to determine an analyte of a sample (e.g., a binding partner of the analyte to be determined) is stored and/or sealed in a channel or chamber of a fluidic device, e.g., prior to first use, in order to perform a specific test or assay.

In cases where an antigen is being analyzed, a corresponding antibody or aptamer can be the binding partner associated with a surface of a microfluidic channel. If an antibody is the analyte, then an appropriate antigen or aptamer may be the binding partner associated with the surface. When a disease condition is being determined, it may be preferred to put the antigen on the surface and to test for an antibody that has been produced in the subject. Such antibodies may include, for example, antibodies to HIV.

In some embodiments, a fluidic device is adapted and arranged to perform an analysis involving accumulating an opaque material on a region of a channel, exposing the region to light, and determining the transmission of light through the opaque material. An opaque material may include a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than, for example, 90, 80, 70, 60, 50, 40, 30, 20, 10, or 1 percent of the light illuminating the opaque material. Examples of opaque materials include molecular layers of metal (e.g., elemental metal), ceramic layers, dyes, polymeric layers, and layers of an opaque substance (e.g., a dye). The opaque material may, in some cases, be a metal that can be electrolessly deposited. These metals may include, for example, silver, gold, copper, nickel, cobalt, palladium, and platinum. Precursors of these metals may be stored and/or flowed in the devices described herein.

An opaque material that forms in a channel may include a series of discontinuous independent particles that together form an opaque layer, but in one embodiment, is a continuous material that takes on a generally planar shape. The opaque material may have a dimension (e.g., a width or length) of, for example, greater than or equal to 1 micron, greater than or equal to 5 microns, greater than 10 microns, greater than or equal to 25 microns, or greater than or equal to 50 microns. In some cases, the opaque material extends across the width of the channel (e.g., an analysis region) containing the opaque material. The opaque layer may have a thickness of, for example, less than or equal to 10 microns, less than or equal to 5 microns, less than or equal to 1 micron, less than or equal to 100 nanometers or less than or equal to 10 nanometers. Even at these small thicknesses, a detectable change in transmittance can be obtained. The opaque layer may provide an increase in assay sensitivity when compared to techniques that do not form an opaque layer.

In one set of embodiments, a fluidic device described herein is used for performing an immunoassay (e.g., for human IgG or PSA) and, optionally, uses silver enhancement for signal amplification. In such an immunoassay, after delivery of a sample (e.g., containing human IgG) to a reaction site or analysis region, binding between two components (e.g., between the human IgG and anti-human IgG) can take place. One or more reagents, which may be optionally stored in a channel of the device prior to use, can then flow over this binding pair complex. Optionally, one of the stored reagents may include a solution of metal colloid (e.g., a gold conjugated antibody) that specifically binds to the antigen to be detected (e.g., human IgG). In other embodiments, the metal colloid can be bound with the sample prior to arriving at the reaction site or analysis region. This metal colloid can provide a catalytic surface for the deposition of an opaque material, such as a layer of metal (e.g., silver), on a surface of the analysis region. The layer of metal can be formed by using a two component system: a metal precursor (e.g., a solution of silver salts) and a reducing agent (e.g., hydroquinone, chlorohydroquinone, pyrogallol, metol, 4-aminophenol and phenidone, Fe(+2), Ti(+3), and V(+2)), which can optionally be stored in different channels prior to use.

Mixing and/or incubation of the two reagents can be performed using the methods described herein. In certain embodiments, as a positive or negative pressure differential is applied to the system, the silver salt and reducing solutions can be combined and mixed (e.g., due to diffusion) in a channel (e.g., an incubation channel), and then flow over the analysis region. If antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. An opaque layer that is formed in the channel can be detected optically, for example, by measuring a reduction in light transmittance through a portion of the analysis region (e.g., a serpentine channel region) compared to a portion of an area that does not include the antibody or antigen.

Alternatively, a signal can be obtained by measuring the variation of light transmittance as a function of time, as the film is being formed in an analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process), or magnetic signals (e.g., magnetic beads) can be used to allow detection of a signal by a detector.

Various types of fluids can be used with the fluidic devices described herein. As described herein, fluids may be introduced into the fluidic device at first use, and/or stored within the fluidic device prior to first use. Fluids include liquids such as solvents, solutions, and suspensions. Fluids also include gases and mixtures of gases. The fluids may contain any suitable species such as a component for a chemical and/or biological reaction, a buffer, and/or a detecting agent. When multiple fluids are contained in a fluidic device, the fluids may be separated by another fluid that is preferably substantially immiscible in each of the first two fluids. For example, if a channel contains two different aqueous solutions, a separation plug of a third fluid may be substantially immiscible in both of the aqueous solutions. When aqueous solutions are to be kept separate, substantially immiscible fluids that can be used as separators may include gases such as air or nitrogen, or hydrophobic fluids that are substantially immiscible with the aqueous fluids. Fluids may also be chosen based at least in part on the fluid's reactivity with adjacent fluids, or based on other factors described herein. For example, an inert gas such as nitrogen may be used in some embodiments and may help preserve and/or stabilize any adjacent fluids. An example of a substantially immiscible liquid for separating aqueous solutions is perfluorodecalin.

The choice of a separator fluid may be made based on other factors as well, including any effect that the separator fluid may have on the surface tension of the adjacent fluid plugs. In some embodiments, it may be preferred to maximize the surface tension within any fluid plug to promote retention of the fluid plug as a single continuous unit under varying environmental conditions such as vibration, shock, and temperature variations. Other factors relevant to mixing between fluids and fluid plugs can also be considered as described herein.

Separator fluids may also be inert to a reaction site (e.g., an analysis region) to which the fluids will be supplied. For example, if a reaction site includes a biological binding partner, a separator fluid such as air or nitrogen may have little or no effect on the binding partner. The use of a gas (e.g., air) as a separator fluid may also provide room for expansion within a channel of a fluidic device should liquids contained in the device expand or contract due to changes such as temperature (including freezing) or pressure variations.

In some embodiments, a fluidic device may be used in connection with an analyzer that may include one or more detectors (e.g., optical system that may include detector(s) and/or light source(s)), temperature control systems (e.g., heater(s)/cooler(s)), pressure-control system (e.g., configured to pressurize the at least one channel in the cassette to move the sample through the at least one channel). For example, an analyzer as described in more detail in U.S. Patent Publication No. 2011/0256551, filed Apr. 15, 2011, entitled "Systems and Devices for Analysis of Samples," may be used.

Any suitable heater can be used to heat a fluid in a fluidic device. In some embodiments, the heater is a part of an analyzer as described herein, although other configurations are also possible. In some cases, a heater includes a resistive heater (e.g., a 12 volt 10 watt resistive heater) sandwiched between a conductive bracket (e.g., a sheet metal bracket)

and a conductive plate (e.g., an anodized aluminum plate). The resistive heater may be designed with a through hole at the center of the component; this through hole can allow for a thermistor to be mounted to the anodized aluminum plate. The conductive plate may have a thickness of for example, about 4 mm at the area where the heater is located. The flat surface of the conductive plate above where the heater is located is the area where the assay cassette can rest (e.g., when the cassata is inserted into the analyzer). For instance, when a solenoid is activated it can apply a force on the assay cassette that is inserted in the analyzer, causing it to become into intimate/physical contact with the flat surface of the conductive plate. The conductive plate conducts and transfers heat from the heater to the assay cassette. The heat then transfers through the lid/cover (e.g., COC lid) of the assay cassette (e.g., a top or bottom of the cassette). The lid or cover may have, for example, a thickness of about 0.004" (or 100 micrometers). The heat applied to the lid/cover can heat up a sample contained inside a channel (e.g., microfluidic channel, incubation channel) of the assay cassette.

Accordingly, in some embodiments, a heater (e.g., used to heat a sample or reagent) includes a conductive plate that is positioned in direct (or indirect) contact with a surface of a fluidic device. The heater may be used to heat all or portions of the device. For instance, the heater may be positioned over, or adjacent to, an incubation channel, but not over/adjacent other components or areas of the device (e.g., a detection zone).

In some embodiments, the heater (e.g., resistive heater) may include a conductor contained within a material (e.g., an insulating material such as silicone rubber). As current passes through the conductive material, heat is generated. The thermistor mounted to the conductive plate may be used to measure temperature of the plate. The resistance of the thermistor is dependent on the temperature it is exposed to. The analyzer may use a PID loop to regulate the temperature of this system.

A variety of determination (e.g., measuring, quantifying, detecting, and qualifying) techniques may be used, e.g., to analyze a sample component or other component or condition associated with a fluidic described herein. Determination techniques may include optically-based techniques such as light transmission, light absorbance, light scattering, light reflection, and visual techniques. Determination techniques may also include luminescence techniques such as photoluminescence (e.g., fluorescence), chemiluminescence, bioluminescence, and/or electrochemiluminescence. In other embodiments, determination techniques may measure conductivity or resistance. As such, an analyzer may be configured to include such and other suitable detection systems.

Different optical detection techniques provide a number of options for determining reaction (e.g., assay results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. In some embodiments, a system may be operated with a minimum of optical devices (e.g., a simplified optical detector). For instance, the determining device may be free of a photomultiplier, may be free of a wavelength selector such as a grating, prism or filter, may be free of a device to direct or collimate light such as a collimator, or may be free of magnifying optics (e.g., lenses). Elimination or reduction of these features can result in a less expensive, more robust device.

Additional examples of detection systems are described in more detail below in U.S. Patent Publication No. 2011/0256551, filed Apr. 15, 2011 and entitled "Systems and Devices for Analysis of Samples," which is incorporated herein by reference in its entirety for all purposes.

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method" [H0498.70211WO00]; International Patent Publication No. WO2005/072858 (International Patent Application Serial No. PCT/US2005/003514), filed Jan. 26, 2005 and entitled "Fluid Delivery System and Method" [H0498.70219WO00]; International Patent Publication No. WO2006/113727 (International Patent Application Serial No. PCT/US06/14583), filed Apr. 19, 2006 and entitled "Fluidic Structures including Meandering and Wide Channels" [H0498.70244WO00]; U.S. Pat. No. 8,202,492, issued Jun. 19, 2012 (filed May 1, 2008) and entitled "Fluidic Connectors and Microfluidic Systems" [C1256.70000US01]; U.S. Patent Publication No. 2009/0075390, filed Aug. 22, 2008, entitled "Liquid Containment for Integrated Assays" [C1256.70001US01]; U.S. Pat. No. 8,222,049, issued Jul. 17, 2012 (filed Apr. 25, 2008), entitled "Flow Control in Microfluidic Systems" [C1256.70002US01]; U.S. Pat. No. 8,221,700, issued Jul. 17, 2012 (filed Feb. 2, 2010), entitled "Structures for Controlling Light Interaction with Microfluidic Devices," [C1256.70003US01]; U.S. Patent Publication No. 2010/0158756, filed Dec. 17, 2009, titled "Reagent Storage in Microfluidic Systems and Related Articles and Methods," [C1256.70004US01]; U.S. Patent Publication No. 2011/0120562, filed Nov. 24, 2010, entitled "Fluid Mixing and Delivery in Microfluidic Systems," [C1256.70005US01]; U.S. Patent Publication No. 2011/0253224, filed Apr. 15, 2011, entitled "Feedback Control in Microfluidic Systems," [C1256.70006US01]; U.S. Patent Publication No. 2011/0256551, filed Apr. 15, 2011, entitled "Systems and Devices for Analysis of Samples," [C1256.70010US01]; U.S. Patent Publication No. 2014/0272935, filed Feb. 7, 2014, entitled "Mixing of Fluids in Fluidic Systems," [C1256.70011US01], each of which is incorporated herein by reference in its entirety for all purposes.

EXAMPLES

Example 1

This example describes a testosterone assay performed in a fluidic device comprising an incubation channel.

Testosterone exists in blood free and also bound to a binding protein, specifically, Sex Hormone Binding Globulin (SHGB). A test for total testosterone should accurately measure the combination of both free and bound testosterone. A common assay format for testosterone involves a pre-analytical step where all the bound testosterone in a sample is released from the binding protein, such that all the testosterone remaining in the sample is free testosterone. This free testosterone is then measured by a competitive assay, whereby the testosterone in a sample competes with testosterone attached to a solid support to bind with a labelled anti-testosterone antibody. After the competition, the sample is washed away, and the amount of labelled material attached to the surface is measured via any suitable method such as fluorescence, chemiluminescence, optical transmission, etc. The higher the signal measured, the more labelled antibody has been captured by the solid support and therefore less captured by testosterone in the sample, indicating a lower concentration of testosterone in the sample.

A testosterone assay was performed in a microfluidic device having the same configuration shown in FIG. 5A. The testosterone assay was implemented using an analyzer as described in more detail in U.S. Patent Publication No. 2011/0256551, filed Apr. 15, 2011, entitled "Systems and Devices for Analysis of Samples," [C1256.70010US01] and the silver amplified nano-gold immunoassay technology, which includes use of a sample collector. The incubation channel of the device had a trapezoidal cross section with a maximum width of 500 um and a minimum width of 312 um, a depth of 350 um, and a length of 86.6 mm. Total volume was 12.31 uL. The detection channel had a maximum width of 120 um and a depth of 50 um. An intervening channel with a trapezoidal cross section (maximum width of 550 um and minimum width of 362 um) and depth of 350 um separated the incubation channel from the detection channel. The intervening channel was connected to the incubation and detection channels with tapered holes with average diameters of approximately 500 um, and a depth of about 0.86 mm.

The width, depth, and length of the incubation channel were sized to contain a sample volume of at least 12 uL (but less than or equal to about 24 uL). The ratio of channel depth to channel width (0.7) was designed to be close to but less than 1. As the ratio of depth to width increases, the parts become more difficult to manufacture by injection molding. As the ratio of depth to width becomes very small, the channels may be more prone to collapse. For example, the channel cover may flex into the full depth of the channel A trapezoidal cross section was selected because the shape provides a draft angle making it easier to eject the part from a mold.

Approximately 12 uL of finger-stick whole blood was collected into the sample collector via capillary action. The sample collector contained lyophilized reagents, e.g., deposited on the inner surface of the channel of the sample collector. The lyophilized reagents were reconstituted by the blood. The lyophilized reagents in the sample collector included anti-coagulants, such heparin, dipyridamole, and EDTA, and anti-testosterone tracer monoclonal antibodies labeled with nano-gold particles. In addition, the lyophilized reagents also included 2-bromoestradiol, a commonly used releasing agent for testosterone, to assist with the release of testosterone in the patient sample. The lyophilized reagents further included a buffer to establish a desirable pH in the sample for the release (e.g., pH 6.5), detergent (Capstone FS-50) to promote flow in the microchannels, anti-species blocking agents (including HAMA blockers, and bovine serum albumin (BSA).

After filling the sample collector, the user connected the sample collector to the microfluidic device. The sample collector formed a bridge between the downstream microchannels in a first cassette which make up the incubation channel, detection channel/zone, and waste feature, and the upstream microchannels in a second cassette which stored liquid reagents necessary for an assay. Plugs of reagents including amplification reagents (e.g., silver nitrate, a reducing agent) were stored in a channel of the second cassette and separated by an immiscible fluid. The user inserted the microfluidic device into the analyzer, and then entered the patient information into the analyzer via a touchscreen, and finally initiated the test. All assay steps were performed automatically with no user intervention as follows.

To introduce the sample, the analyzer applied a vacuum to the microfluidic device, pulling the sample mixture from the sample collector into the incubation channel in the microfluidic device. Downstream of the incubation channel was a detection channel of a detection zone of the microfluidic device. Once the sample mixture entered into a part (but not all) of this zone/channel (which had a maximum width of 120 um and a depth of 50 um), and the presence of the sample was detected optically via a reduction in light transmission by the analyzer, the analyzer stopped the sample flow. This was accomplished by releasing the vacuum that was applied to the microfluidic device.

Sample incubation occurred while the fluid flow was stopped for five minutes. During this time, testosterone bound to SHBG in the sample was released, aided by pH, releasing agent, and temperature. The temperature in the region of the analyzer adjacent to the incubation channel was controlled at 37° C. The testosterone in the sample mixture bound to the gold-labeled anti-testosterone antibodies to form labeled antigen-antibody complexes.

After five minutes, the fluid flow was resumed by re-application of the vacuum. The experiment was run multiple times. In approximately 10% of the runs, the sample flow could not be re-initiated after the incubation step due to clogging of the blood at the air/sample interface in the detection channel. In the runs where clogging was not observed, the sample flowed through multiple analysis regions of the detection zone within the microfluidic device, including a test region, a negative control region, and a positive control region. In the test region, the labelled anti-testosterone antibodies bound to testosterone attached to the surface of the channel surfaces. The more testosterone initially in the patient sample, the fewer anti-testosterone antibodies were available to bind to the testosterone attached to the channel surfaces.

The unbound material was removed by flowing wash plugs that were stored upstream in the microfluidic device (e.g., upstream of the sample collector) through the sample collector and through the incubation channel, and detection channel of the detection zone. A sequence of automatic washing steps removed sample components and reagents which were not specifically bound to testosterone in the analysis regions of the detection zone. Amplification and detection of the signal was performed by flowing a silver amplification reagent following the wash plugs through the detection zone. The amplification agent reacted with the available nano-gold particles. The reaction resulted in the deposition of a visible silver metallic film within the analysis region, which blocked the transmission of light. The optical density of this film was inversely related to of the concentration of testosterone in the sample.

The testosterone concentration was calculated based on the optical readings and calibration information. The test results were displayed and stored on the analyzer. All reagents and the sample were contained by the waste zone within the microfluidic device. Upon completion of the assay, the user discarded the microfluidic device in a biohazard container.

Figure 13:
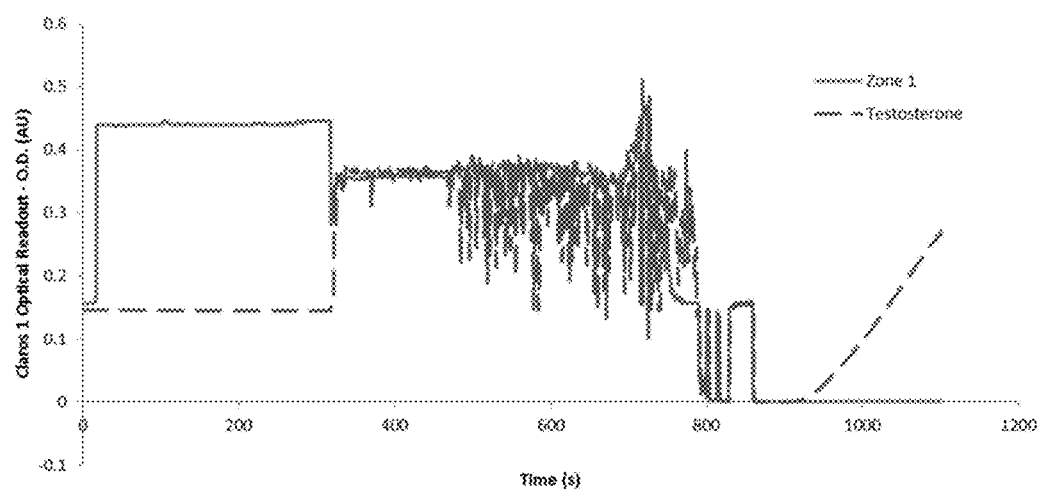
FIG. 13 shows a plot of optical readout versus time for a detector in the fluidic device according to one set of embodiments.

FIG. 13 shows the time series of optical readouts in two analysis regions of the microfluidic whole blood testosterone assay. The solid line corresponds to the optical readout (OD) in the first analysis region. The dashed line represents the optical readout in a later zone dedicated to measuring testosterone when the testosterone was bound to the channel surface in that zone for a competitive assay. As can be seen, once sample was detected in first analysis region, flow was stopped for 300 seconds. The sample did not flow onward into the testosterone analysis region during this time. After five minutes, the vacuum was re-applied and the sample flowed through all the zones. At the end of the assay, silver amplification reagents flowed through the remaining analysis regions. In the testosterone analysis region, an increase in optical density corresponding to silver formed on the gold attached to the captured anti-testosterone antibodies was seen. A steeper slope corresponds to a lower concentration of testosterone in the sample.

Figure 14A:
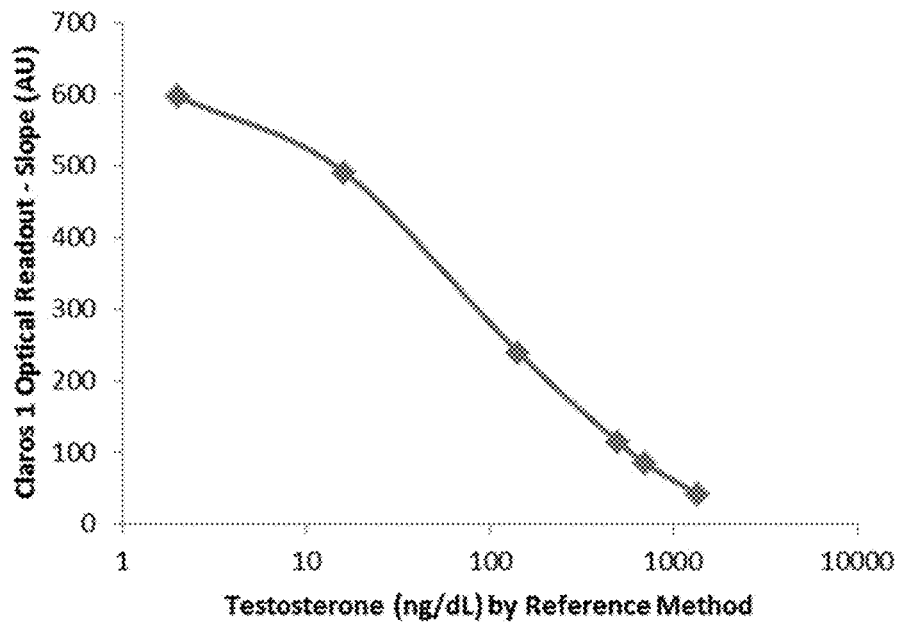
FIGS. 14A-B show plots of testosterone dose response according to certain embodiments.
Figure 14B:
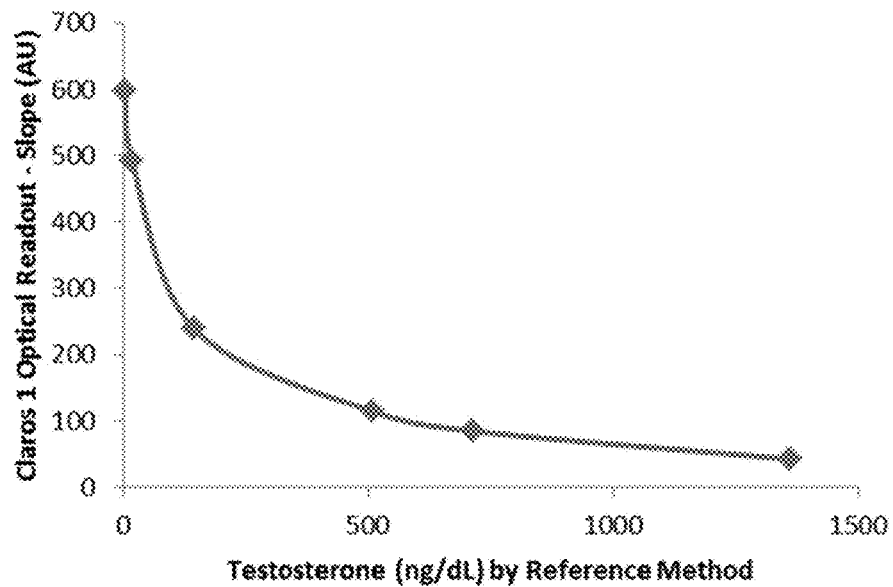

FIGS. 14A-B show the dose response for the testosterone assay performed in the microfluidic device.

Example 2

This example describes a testosterone assay performed in a fluidic device comprising an incubation channel.

A testosterone assay was performed in a microfluidic device having the same configuration shown in FIG. 5A and as described in Example 1, except approximately 12 uL of EDTA-anticoagulated venous whole blood was collected into the sample collector via capillary action.

The assay steps were performed automatically with no user intervention as follows.

To introduce the sample, the analyzer applied a vacuum to the microfluidic device, pulling the sample mixture from the sample collector into the incubation channel in the microfluidic device. Downstream of the incubation channel was a detection channel of the microfluidic device. The vacuum was applied at a level and for a period of time determined to bring the majority of the sample within the incubation channel (which had a trapezoidal cross section with a maximum width of 500 um and a minimum width of 312 um, a depth of 350 um, and a length of 86.6 mm) The vacuum level and time of application of the vacuum was determined by taking into account the type of sample and its flow properties (e.g., viscosity of the sample), and the channel dimensions leading up to and including the incubation channel (e.g., width, height, length, and thereby volume). After this time elapsed, the analyzer released the vacuum and stopped the sample flow so that the sample did not flow beyond the incubation channel (e.g., did not flow into the detection channel or detection zone).

Sample incubation occurred while the fluid flow was stopped for five minutes. During this time, testosterone bound to SHBG in the sample was released, aided by pH, releasing agent, and temperature. The temperature in the region of the analyzer adjacent to the incubation channel was controlled at 37° C. The testosterone in the sample mixture bound to the gold-labeled anti-testosterone antibodies to form labeled antigen-antibody complexes.

After five minutes, the fluid flow was resumed by re-application of the vacuum. The experiment was run multiple times. In each run, no clogging of the blood (e.g., at the air/sample interface) was observed in the incubation channel. The sample then flowed into the detection channel and through multiple analysis regions of the detection zone within the microfluidic device, including a test region, a negative control region, and a positive control region. In the test region, the labelled anti-testosterone antibodies bound to testosterone attached to the surface of the channel surfaces. The more testosterone initially in the patient sample, the fewer anti-testosterone antibodies were available to hind to the testosterone attached to the channel surfaces.

The unbound material was removed by flowing wash plugs that were stored upstream in the microfluidic device (e.g., upstream of the sample collector) through the sample collector and through the incubation channel, and detection channel of the detection zone. A sequence of automatic washing steps removed sample components and reagents which were not specifically bound to testosterone in the analysis regions of the detection zone. Amplification and detection of the signal was performed by flowing a silver amplification reagent following the wash plugs through the detection zone. The amplification agent reacted with the available nano-gold particles. The reaction resulted in the deposition of a visible silver metallic film within the analysis region, which blocked the transmission of light. The optical density of this film was inversely re to of the concentration of testosterone in the sample.

The testosterone concentration was calculated based on the optical readings and calibration information. The test results were displayed and stored on the analyzer. All reagents and the sample were contained by the waste zone within the microfluidic device. Upon completion of the assay, the user discarded the microfluidic device in a biohazard container.

Figure 15:
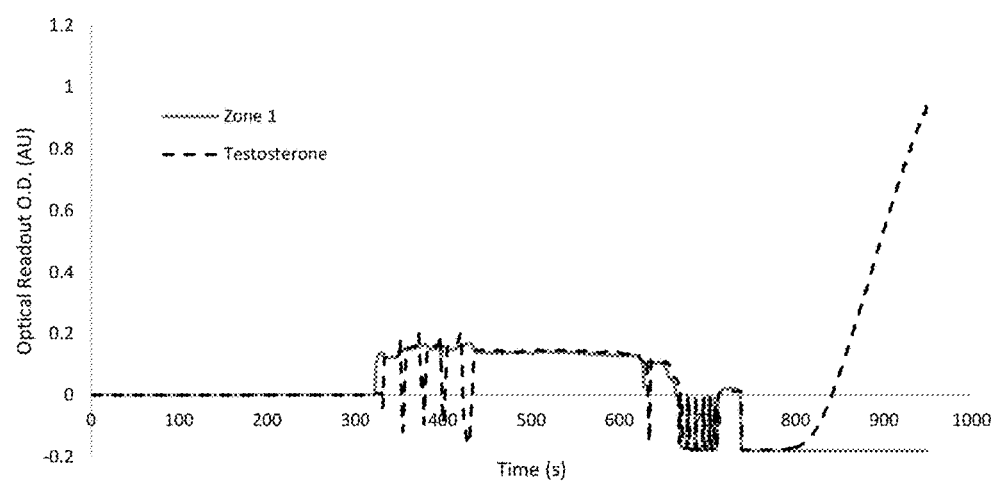
FIG. 15 shows the time series of optical readouts in two analysis regions of a fluidic device used for performing a whole blood testosterone assay of Example 2.

FIG. 15 shows the time series of optical readouts in two analysis regions of a fluidic device used for performing a whole blood testosterone assay. The solid line (labelled zone 1 in FIG. 15) corresponds to the optical readout (OD) in the first analysis region of a detection zone, where no binding of a sample component took place. The dashed line (labelled testosterone in FIG. 15) represents the optical readout in a later zone dedicated to measuring testosterone when the testosterone was bound to the channel surface in that zone for a competitive assay. As can be seen, the sample did not reach the first detection zone until after the 300 s incubation period, during which time the sample flowed into the incubation channel and flow was stopped. After five minutes, the vacuum was re-applied and the sample flowed through all the zones. At the end of the assay, silver amplification reagents flowed through the remaining analysis regions. In the testosterone analysis region, an increase in optical density corresponding to silver formed on the gold attached to the captured anti-testosterone antibodies was seen. A steeper slope corresponds to a lower concentration of testosterone in the sample.

Figure 16A:
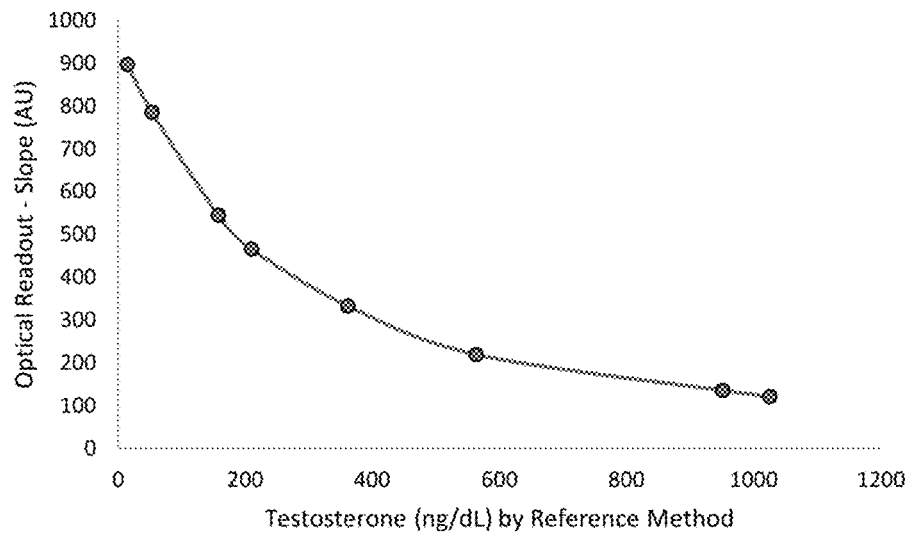
FIGS. 16A and 16B show the dose response for the testosterone assay performed in a microfluidic device of Example 2.
Figure 16B:
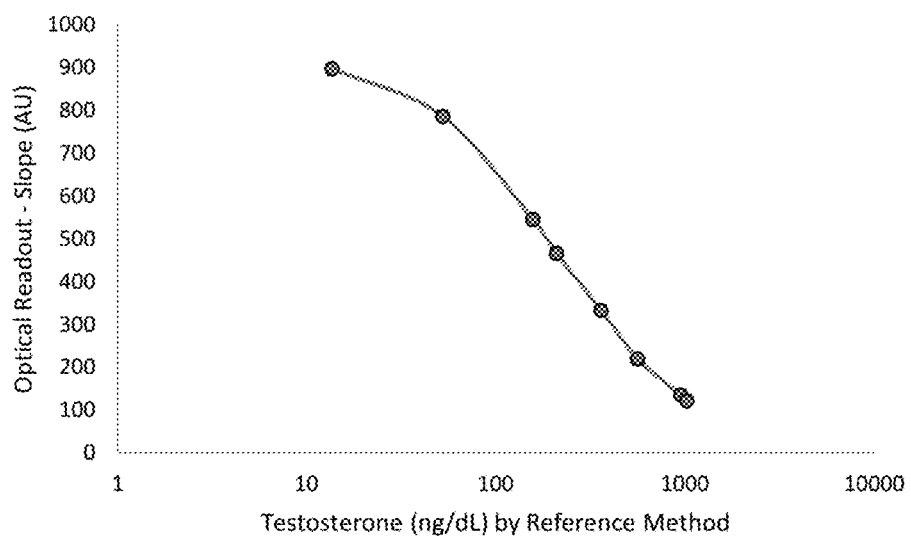

FIGS. 16A and 16B show the dose response for the testosterone assay performed in the microfluidic device.

Example 3

This example describes a testosterone assay performed in a fluidic device comprising an incubation channel.

Testosterone exists in blood free and also bound to a binding protein, specifically, Sex Hormone Binding Globulin (SHGB). A test for total testosterone should accurately measure the combination of both free and bound testosterone. A common assay format for testosterone involves a pre-analytical step where all the bound testosterone in a sample is released from the binding protein, such that all the testosterone remaining in the sample is free testosterone. This free testosterone is then measured by a competitive assay, whereby the testosterone in a sample competes with labeled testosterone to bind with an anti-testosterone antibody attached onto a solid support. After the competition, the sample is washed away, and the amount of labelled material attached to the surface is measured via any suitable method such as fluorescence, chemiluminescence, optical transmission, etc. The higher the signal measured, the more labelled testosterone has been captured by the solid support and therefore less testosterone has been captured from the sample, indicating a lower concentration of testosterone in the sample.

A testosterone assay was performed in a microfluidic device having the same configuration shown in FIG. 5A and as described in Example 1, except approximately 10 mL of EDTA-anticoagulated whole blood from a female donor with low endogenous testosterone was divided into aliquots of approximately 1 mL and was spiked with additional testosterone to levels of approximately 250 and 1500 ng/dL. These spiked aliquots were then mixed with a solution containing a reagent mixture for the assay. The reagents in the mixture included anti-coagulants, such heparin, dipyridamole, and EDTA, and testosterone-BSA conjugate (with an approximately 8:1 molar ratio of steroid to carrier protein) labeled with nano-gold particles. In addition, the reagents also included 2-bromoestradiol, a commonly used releasing agent for testosterone, to assist with the release of testosterone in the patient sample. The reagents further included a buffer to establish a desirable pH in the sample for the release (i.e., pH 6.5), detergent (e.g., Capstone FS-50 or Pluronic P123 to promote the flow in the microchannels, anti-species blocking agents (including HAMA blockers), and bovine serum albumin (BSA). Approximately 12 uL of the EDTA-anticoagulated venous whole blood mixed with the above reagents was collected into the sample collector via capillary action.

After filling the sample collector, the user connected the sample collector to the microfluidic device. The sample collector formed a bridge between the downstream microchannels in a first cassette which make up the incubation channel, detection channel/zone, and waste feature, and the upstream microchannels in a second cassette which stored liquid reagents necessary for an assay. Plugs of reagents including amplification reagents (e.g., silver nitrate, a reducing agent) and wash fluids were stored in a channel of the second cassette and separated by an immiscible fluid. The user inserted the microfluidic device into the analyzer, and then entered the patient information into the analyzer via a touchscreen, and finally initiated the test. All assay steps were performed automatically with no user intervention as follows.

To introduce the sample, the analyzer applied a vacuum to the microfluidic device, pulling the sample mixture from the sample collector into the incubation channel in the microfluidic device. Downstream of the incubation channel was a detection channel of a detection zone of the microfluidic device. The vacuum was applied at a level and for a period of time determined to bring the majority of the sample within the incubation channel. After this time elapsed, the analyzer released the vacuum and stopped the sample flow.

Sample incubation occurred while the fluid flow was stopped for five minutes. During this time, testosterone bound to SHBG in the sample was released, aided by pH, releasing agent, and temperature. The temperature in the region of the analyzer adjacent to the incubation channel was controlled at 37° C.

After five minutes, the fluid flow was resumed by re-application of the vacuum. The experiment was run multiple times. In each run, no clogging of the blood (e.g., at the air/sample interface) was observed in the incubation channel. The sample then flowed into the detection channel and through multiple analysis regions of the detection zone within the microfluidic device, including a test region, a negative control region, and a positive control region. In the test region, the sample testosterone and the labelled testosterone-BSA conjugate competed to bind to anti-testosterone antibodies attached to the surface of the channel surfaces. The more testosterone initially in the patient sample, the fewer labeled testosterone-BSA conjugates were could bind to the anti-testosterone antibodies attached to the channel surfaces.

The unbound material was removed by flowing wash plugs that were stored upstream in the microfluidic device (e.g., upstream of the sample collector) through the sample collector and through the incubation channel, and detection channel of the detection zone. A sequence of automatic washing steps removed sample components and reagents which were not specifically bound in the analysis regions of the detection zone. Amplification and detection of the signal was performed by flowing a silver amplification reagent following the wash plugs through the detection zone. The amplification agent reacted with the available nano-gold particles. The reaction resulted in the deposition of a visible silver metallic film within the analysis region, which blocked the transmission of light. The optical density of this film was inversely related to of the concentration of testosterone in the sample.

The testosterone concentration was calculated based on the optical readings and calibration information. The test results were displayed and stored on the analyzer. All reagents and the sample were contained by the waste zone within the microfluidic device. Upon completion of the assay, the user discarded the microfluidic device in a biohazard container.

Figure 17:
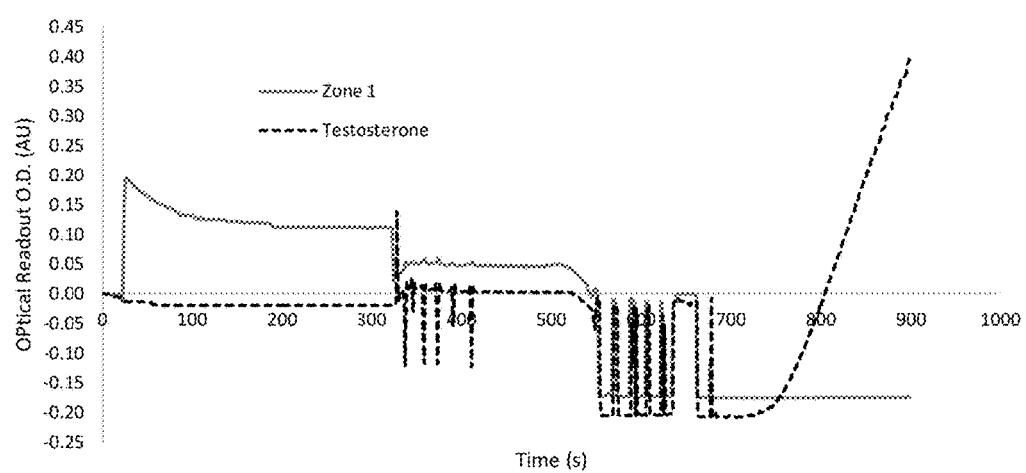
FIG. 17 shows the time series of optical readouts in two analysis regions of a fluidic device used for performing a whole blood testosterone assay of Example 3.

FIG. 17 shows the time series of optical readouts in two analysis regions of the microfluidic whole blood testosterone assay. The solid line (labelled zone 1 in FIG. 17) corresponds to the optical readout (OD) in the first analysis region of a detection zone, where no binding of a sample component took place. The dashed line (labelled Testosterone in FIG. 17) represents the optical readout in a later zone dedicated to measuring testosterone when the testosterone was bound to the channel surface in that zone for a competitive assay. As can be seen, once sample was detected in the first analysis region, flow was stopped for 300 seconds. The sample did not flow onward into the testosterone analysis region during this time. After five minutes, the vacuum was re-applied and the sample flowed through all the zones. At the end of the assay, silver amplification reagents flowed through the remaining analysis regions. In the testosterone analysis region, an increase in optical density corresponding to silver formed on the gold attached to the captured anti-testosterone antibodies was seen. A steeper slope corresponds to a lower concentration of testosterone in the sample.

Figure 18A:
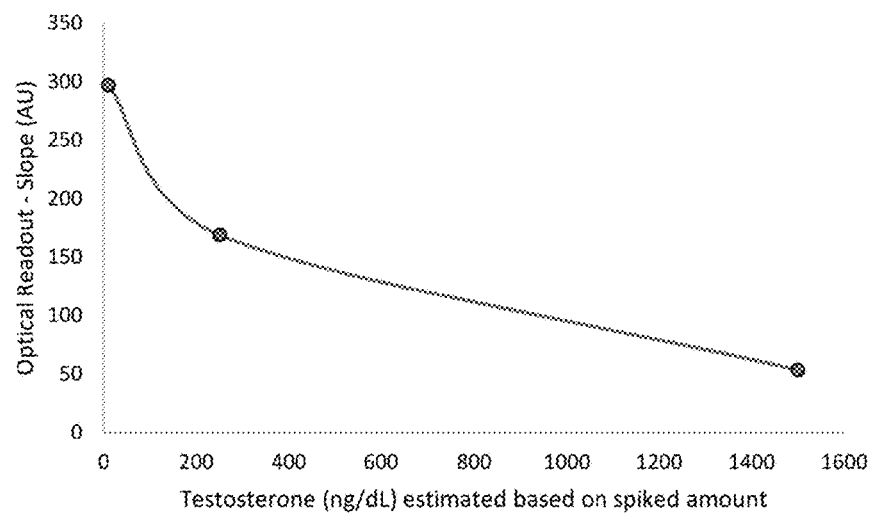
FIGS. 18A and 18B show the dose response for the testosterone assay performed in the microfluidic device of Example 3.
Figure 18B:
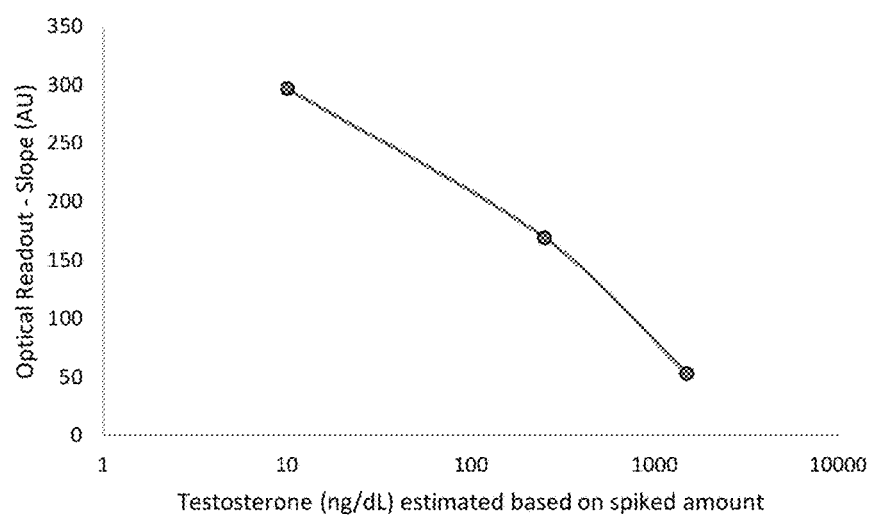

FIGS. 18A-18B show the dose response for the testosterone assay performed in the microfluidic device.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:
1. A method, comprising:
in a fluidic system comprising a sample collector and an article, performing the steps of:
introducing a sample comprising a sample component into the sample collector;

connecting the sample collector to a sample inlet port of the article, wherein the article comprises first and second sides, wherein the first side comprises an incubation channel, and wherein the first side and/or second side comprises a detection channel in fluid communication with the incubation channel, and wherein the sample inlet port is in fluid communication with the incubation channel;

flowing, at a first flow rate, at least a portion of the sample from the sample collector to the incubation channel;

reducing the flow rate of the sample to a second flow rate, wherein the second flow rate is less than the first flow rate and/or is zero to allow incubation of the sample in the incubation channel;

modulating the flow rate of the sample to a third flow rate which is greater than the second flow rate; and flowing the sample through the detection channel;

wherein a ratio of heights and/or widths of the incubation channel to the detection channel is at least about 5:1, and wherein prior to the step of reducing the flow rate of the sample, at least a portion of the sample is flowed into the detection channel.

2. A method, comprising:

in a fluidic system comprising a sample collector and an article, performing the steps of:

introducing a sample comprising a sample component into the sample collector;

connecting the sample collector to a sample inlet port of the article, wherein the article comprises first and second sides, wherein the first side comprises an incubation channel, and wherein the first side and/or second side comprises a detection zone comprising a detection channel in fluid communication with the incubation channel, and wherein the sample inlet port is in fluid communication with the incubation channel;

flowing, at a first flow rate, at least a portion of the sample from the sample collector to the incubation channel;

flowing at least a portion of the sample into a part, but not all, of the detection zone;

reducing the flow rate of the sample to a second flow rate, wherein the second flow rate is less than the first flow rate and/or is zero;

modulating the flow rate of the sample to a third flow rate which is greater than the second flow rate; and flowing the sample through the detection channel.

3. A method as in claim 2, wherein the incubation channel has a cross-sectional area that is greater than a cross-sectional area of the detection channel.

4. A method as in claim 2, wherein the incubation channel has a cross-sectional area that is at least 0.008 mm$^2$, and the detection channel has a cross-sectional area that is less than 0.008 mm$^2$.

5. A method as in claim 2, wherein prior to the step of reducing the flow rate, none of the sample is flowed into the detection channel.

6. A method as in claim 2, wherein prior to the step of reducing the flow rate of the sample, at least a portion of the sample is flowed into the detection channel.

7. A method as in claim 2, comprising flowing at least a portion of the sample into a part, but not all, of the detection channel, detecting at least a portion of the sample at the detection channel, and then reducing the flow rate of the sample to the second flow rate.

8. A method as in claim 2, wherein the incubation channel has a width of at least about 100 microns and less than or equal to about 2 mm, a height of at least about 50 microns and less than or equal to about 2 mm, and a volume of at least 5 μL.

9. A method as in claim 2, wherein the detection channel has a width of at least about 50 microns and less than or equal to about 300 microns, and a height of at least about 10 microns and less than or equal to about 300 microns.

10. A method as in claim 2, wherein the detection channel comprises a reagent deposited on a surface of the detection channel.

11. A method as in claim 10, wherein the reagent is stored.

12. A method as in claim 10, comprising contacting the sample with the reagent, wherein the contacting step occurs after the step of flowing at least a portion of the sample from the sample collector to the incubation channel.

13. A method as in claim 2, wherein a first intervening channel passes through a thickness of the article and is positioned between the incubation channel and the detection channel.

14. A method as in claim 2, wherein a surface of the article comprises a reagent deposited thereon, and wherein the reagent is deposited on the surface by flowing a liquid containing the reagent across the surface and depositing the reagent during the step of flowing, at the first flow rate, at least a portion of the sample from the sample collector to the incubation channel.

15. A method as in claim 14, comprising mixing the sample component with the reagent in the sample in the incubation channel.

16. A method as in claim 14, comprising removing at least a portion of the reagent from the surface such that the reagent is dissolved or suspended in the sample.

17. A method as in claim 14, comprising removing at least a portion of the reagent from the surface such that the reagent is dissolved or suspended in the sample, and wherein the step of removing at least a portion of the reagent from the surface takes place in the incubation channel.

18. A method as claim 2, comprising performing the step of flowing, at the first flow rate, at least a portion of the sample from the sample collector to the incubation channel, followed by flowing at least a portion of the sample into a part, but not all, of the detection zone, followed by the step of reducing the flow rate of the sample to the second flow rate, followed by the step of modulating the flow rate of the sample to the third flow rate, followed by the step of flowing the sample through the detection channel.

19. A method as in claim 2, wherein a portion of the sample, but less than or equal to 10% of the sample, is flowed into part of, but not all, of the detection zone prior to the step of reducing the flow rate of the sample.

20. A method as in claim 2, wherein prior to the step of reducing the flow rate of the sample, at least a portion of the sample is detected at the detection zone.

21. A method as in claim 2, wherein a portion of the incubation channel is a part of the detection zone.

22. A method as in claim 21, wherein at least a portion of the sample is detected at the incubation channel.

* * * * *